(12) United States Patent
Miyashita et al.

(10) Patent No.: US 11,522,137 B2
(45) Date of Patent: Dec. 6, 2022

(54) ORGANIC LIGHT EMITTING ELEMENT, DISPLAY DEVICE, IMAGE INFORMATION PROCESSING DEVICE, LIGHTING DEVICE, IMAGE FORMING DEVICE, EXPOSURE DEVICE, AND ORGANIC PHOTOELECTRIC CONVERSION ELEMENT

(71) Applicant: CANON KABUSHIKI KAISHA, Tokyo (JP)

(72) Inventors: Hirokazu Miyashita, Ebina (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 22 days.

(21) Appl. No.: 16/569,430

(22) Filed: Sep. 12, 2019

(65) Prior Publication Data
US 2020/0006667 A1 Jan. 2, 2020

Related U.S. Application Data

(63) Continuation of application No. 15/205,552, filed on Jul. 8, 2016, now abandoned.

(30) Foreign Application Priority Data

Jul. 9, 2015 (JP) ................. 2015-138156

(51) Int. Cl.
*H01L 51/00* (2006.01)
*C07D 277/22* (2006.01)
(Continued)

(52) U.S. Cl.
CPC ........ *H01L 51/0069* (2013.01); *C07D 263/32* (2013.01); *C07D 263/56* (2013.01);
(Continued)

(58) Field of Classification Search
USPC ....... 428/690, 691, 917, 411.4, 336; 427/58, 427/66; 313/500–512; 257/40, 88–104,
(Continued)

(56) References Cited

U.S. PATENT DOCUMENTS

2006/0192496 A1* 8/2006 Yamada ................ G09G 3/325
315/169.3
2012/0256172 A1* 10/2012 Ito ........................ C07D 307/91
257/40
(Continued)

FOREIGN PATENT DOCUMENTS

| JP | 2003332551 A | 11/2003 |
| JP | 2009081297 A | 4/2009 |

(Continued)

*Primary Examiner* — Sean M DeGuire
(74) *Attorney, Agent, or Firm* — Canon U.S.A., Inc. IP Division

(57) ABSTRACT

The present disclosure provides an organic light emitting element which has a pair of electrodes and an organic compound layer disposed therebetween and in which the organic compound layer contains an organic compound represented by the following general formula [1],

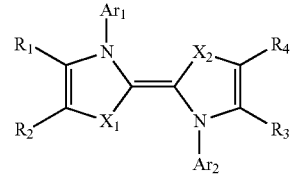

[1]

wherein in the formula [1], $Ar_1$ and $Ar_2$ each independently represent an aromatic hydrocarbon group or a heteroaromatic ring group, $R_1$ to $R_4$ are each independently selected (Continued)

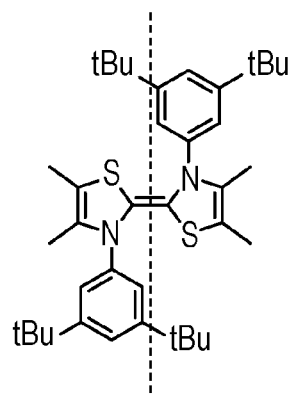

EXAMPLE COMPOUND A5
SYMMETRY

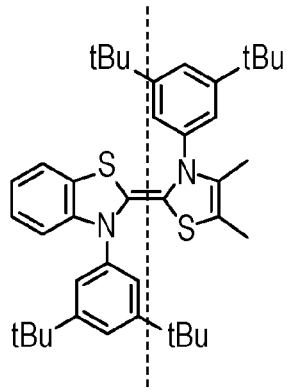

EXAMPLE COMPOUND D1
ASYMMETRY from a hydrogen atom or a substituent, $R_1$ and $R_2$ and $R_3$ and $R_4$ each may form a benzene ring, wherein the benzene ring may have at least one substituent.

23 Claims, 4 Drawing Sheets

(51) Int. Cl.

| | |
|---|---|
| *C07D 263/32* | (2006.01) |
| *C07D 277/64* | (2006.01) |
| *C07D 263/56* | (2006.01) |
| *H01L 51/50* | (2006.01) |
| *H01L 27/32* | (2006.01) |
| *H01L 27/12* | (2006.01) |
| *H01L 27/30* | (2006.01) |

(52) U.S. Cl.
CPC ......... *C07D 277/22* (2013.01); *C07D 277/64* (2013.01); *H01L 51/0071* (2013.01); *H01L 27/1225* (2013.01); *H01L 27/307* (2013.01); *H01L 27/3234* (2013.01); *H01L 27/3262* (2013.01); *H01L 51/5092* (2013.01)

(58) Field of Classification Search
USPC ........ 257/E51, E51.052; 252/301.16–301.35
See application file for complete search history.

(56) References Cited

U.S. PATENT DOCUMENTS

| | | | |
|---|---|---|---|
| 2012/0262087 A1* | 10/2012 | Watanabe | H05B 45/3725 |
| | | | 315/291 |
| 2015/0060804 A1* | 3/2015 | Kanitz | H01L 51/0051 |
| | | | 257/40 |

FOREIGN PATENT DOCUMENTS

| | | |
|---|---|---|
| JP | 2009267912 A | 11/2009 |
| JP | 2015115331 A | 6/2015 |

\* cited by examiner

EXAMPLE COMPOUND A5
SYMMETRY

EXAMPLE COMPOUND D1
ASYMMETRY

ORGANIC LIGHT EMITTING ELEMENT, DISPLAY DEVICE, IMAGE INFORMATION PROCESSING DEVICE, LIGHTING DEVICE, IMAGE FORMING DEVICE, EXPOSURE DEVICE, AND ORGANIC PHOTOELECTRIC CONVERSION ELEMENT

CROSS REFERENCE TO RELATED APPLICATIONS

The present application is a continuation of U.S. patent application Ser. No. 15/205,552 filed on Jul. 8, 2016, which claims priority from Japanese Patent Application No. 2015-138156, filed Jul. 9, 2015, both of which are hereby incorporated by reference herein in their entirety.

BACKGROUND

Field of the Disclosure

The present disclosure relates to an organic light emitting element, a display device, an image information processing device, a lighting device, an image forming device, an exposure device, and an organic photoelectric conversion element.

Description of the Related Art

An organic light emitting element is an electronic element having an anode, a cathode, and an organic compound layer disposed between the two electrodes. In the organic light emitting element, since positive holes (holes) and electrons injected from the respective electrodes are recombined in the organic compound layer, excitons are generated, and light is emitted when the excitons are returned to the ground state. Recent development of organic light emitting elements has been remarkably carried out, and a thin and lightweight light emitting device having a low drive voltage, various light emission wavelengths, and a high responsivity can be realized.

However, the light emission efficiency and the serviceable life of the organic light emitting element can be still further improved, and in particular, a decrease in drive voltage of the light emitting element has been desired.

In the organic light emitting element, in order to decrease the drive voltage, the improvement in electron injection property is preferable. As a compound having a high electron injection property, heretofore, a compound, such as LiF, including an alkali metal or an alkaline earth metal has been used.

In "Acidities of C2 Hydrogen Atoms in Thiazolium Cations and Reactivities of Their Conjugate Bases", Journal of American Chemical Society 113, 985 to 990, (1991) (hereinafter, referred to as "Non-Patent Literature 1") by F. G. Bordwell, a synthesis method of compounds represented by 1-A and 1-B has been disclosed. However, all those compounds are unstable, that is, for example, 1-A is easily oxidized in the air, and the structure of 1-B is easily transformed at room temperature. Those compounds have not been described as a compound to be used for an organic electric-field element.

In "Investigation the Reaction of Benzazolium Salt with Base" Chemical & Pharmaceutical Bulletin 17(7), 1,462 to 1,466, (1969) (hereinafter, referred to as "Non-Patent Literature 2") by Akira Takamizawa, although a synthesis method of a compound as represented by 1-C has been described, the material is unstable and is easily oxidized as is the compound represented by 1-A. This compound has not been described as a material to be used for an organic electric-field element.

In "Diazadithiafulvalenes as electron donor reagents", Journal of Chemical Society, Perkin Transactions 1: Organic and Bio-Organic Chemistry 24, 3,637 to 3,643, (1999) (hereinafter, referred to as "Non-Patent Literature 3") by Toshio Koizumi, although a synthesis method of a compound as represented by 1-D has been described, this compound has not been described as a material to be used for an organic electric-field element.

In "A Stable Thiazol-2-ylidene and Its Dimer", Liebigs Annalen/Recueil 2, 365 to 374, (1977) (hereinafter, referred to as "Non-Patent Literature 4") by Anthony J. Arduego, although a synthesis method of a compound as represented by 1-E has been described, this compound has not been described as a material to be used for an organic electric-field element.

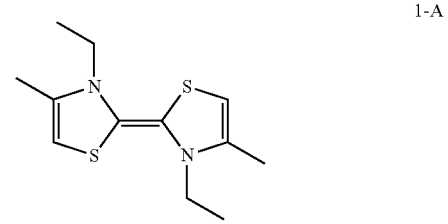

1-A

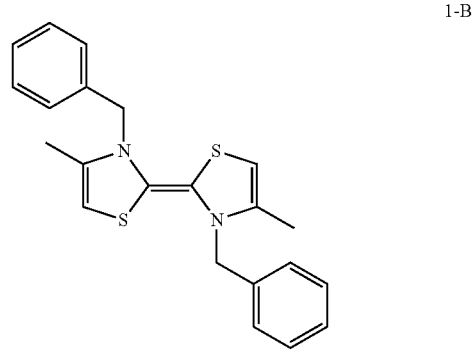

1-B

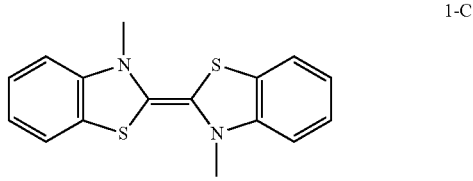

1-C

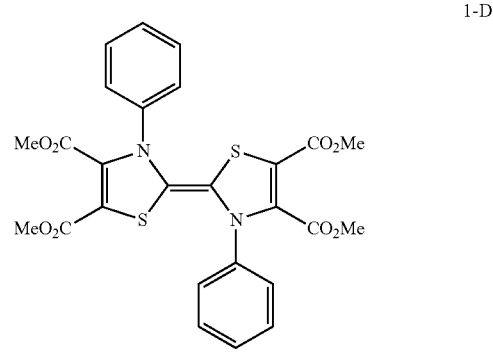

1-D

-continued

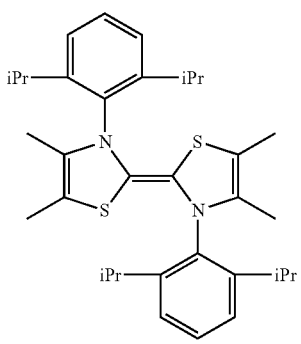

1-E

Although the organic compounds disclosed in Non-Patent Literatures 1 and 2 have a high electron injection property, the reactivity thereof with moisture is high, and hence, those compounds have a low stability in the air. Although being stable in the air, the organic compounds disclosed in Non-Patent Literatures 3 and 4 have not been described as a material to be used for an organic electric-field element.

SUMMARY

The present disclosure provides an organic light emitting element containing an organic compound which has a high stability against oxidation in the air and which is not likely to be structure-transformed in the air.

Accordingly, the present disclosure provides an organic light emitting element which has a pair of electrodes and an organic compound layer disposed therebetween and in which the organic compound layer contains an organic compound represented by the following general formula [1].

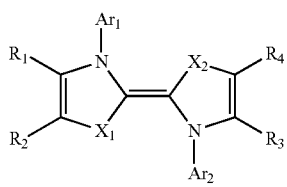

[1]

In the formula [1], $Ar_1$ and $Ar_2$ each represent an aromatic hydrocarbon group having 6 to 24 carbon atoms with or without at least one substituent or a heteroaromatic ring group having 3 to 23 carbon atoms.

$R_1$ to $R_4$ are each independently selected from the group consisting of a hydrogen atom, a halogen atom, a cyano group, an alkyl group having 1 to 8 carbon atoms, a phenyl group with or without at least one substituent, and a pyridyl group with or without at least one substituent. $R_1$ and $R_2$ may be bonded to each other to form a benzene ring, and $R_3$ and $R_4$ may also be bonded to each other to form a benzene ring. The benzene ring described above may have as a substituent, at least one selected from the group consisting of a halogen atom, a cyano group, an alkyl group having 1 to 8 carbon atoms, a phenyl group with or without at least one substituent, and a pyridyl group with or without at least one substituent.

$X_1$ and $X_2$ represent a sulfur atom or an oxygen atom, and $X_1$ and $X_2$ represent the same atom.

Further features of the present disclosure will become apparent from the following description of exemplary embodiments with reference to the attached drawings.

DESCRIPTION OF THE EMBODIMENTS

Figure 1A:
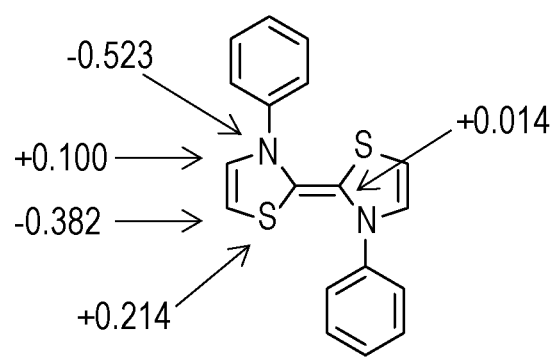
FIGS. 1A and 1B are views each showing the electron density based on the molecular orbital calculation of one example of a fulvalene compound according to the present disclosure.

The present disclosure relates to an organic light emitting element having a pair of electrodes and an organic compound layer disposed therebetween. The organic compound layer contains an organic compound represented by the general formula [1]. Since an aromatic hydrocarbon group or a heteroaromatic ring group is provided as $Ar_1$ and $Ar_2$, the organic compound represented by the general formula [1] has a low reactivity with oxygen and moisture in the air and can be stably present. In addition, by the use of the compound described above, an organic light emitting element having a high stability can be provided.

In this embodiment, the organic compound represented by the general formula [1] is called a fulvalene compound according to the present disclosure in some cases.

The organic compound according to the present disclosure is represented by the following general formula [1] or [2].

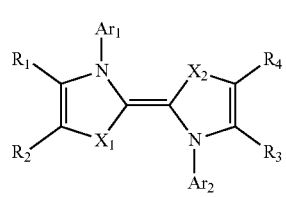

[1]

In the formula [1], $Ar_1$ and $Ar_2$ each represent an aromatic hydrocarbon group having 6 to 24 carbon atoms or a heteroaromatic ring group having 3 to 23 carbon atoms. $Ar_1$ and $Ar_2$ each may have as a substituent, at least one selected from the group consisting of a halogen atom, a cyano group, an alkyl group having 1 to 4 carbon atoms, a phenyl group, a tolyl group, a xylyl group, a mesityl group, and a cumenyl group.

$R_1$ to $R_4$ are each independently selected from the group consisting of a hydrogen atom, a halogen atom, a cyano group, an alkyl group having 1 to 8 carbon atoms, a phenyl group with or without at least one substituent, and a pyridyl group with or without at least one substituent.

$X_1$ and $X_2$ represent a sulfur atom or an oxygen atom, and $X_1$ and $X_2$ represent the same atom. That is, when $X_1$ and $X_2$ each represent a sulfur atom, a dithiadiazafulvalene compound is formed, and when $X_1$ and $X_2$ each represent an oxygen atom, a dioxadiazafulvalene compound is formed.

$R_1$ and $R_2$ may be bonded to each other to form a benzene ring, and $R_3$ and $R_4$ may also be bonded to each other to form a benzene ring. The benzene ring thus formed may have at least one substituent. The substituent that the benzene ring may have is the same as the substituent that $R_1$ to $R_4$ may have When $R_1$ and $R_2$ are bonded to each other to form a benzene ring, and $R_3$ and $R_4$ are bonded to each other to form a benzene ring, for example, an organic compound represented by the following general formula [2] is formed.

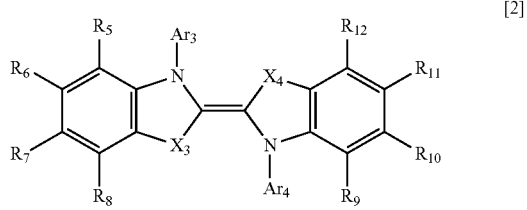

[2]

In the formula [2], $R_5$ to $R_{12}$ are each independently selected from a hydrogen atom or a substituent. The substituent is the same as the substituent that $R_1$ to $R_4$ may select.

In addition, $R_1$ and $R_2$ or $R_3$ and $R_4$ in the general formula [1] may be bonded to each other to form a benzene ring. In the case described above, the compound thus formed is called benzodithiadiazafulvalene or benzodioxadiazafulvalene. From a synthesis easiness point of view, when the ring is formed, $R_1$ and $R_2$ and $R_3$ and $R_4$ both preferably form the rings.

As the aromatic hydrocarbon group having 6 to 24 carbon atoms, for example, a phenyl group, a naphthyl group, a phenanthryl group, a fluorenyl group, a fluoranthenyl group, a triphenylenyl group, an anthracenyl group, or a pyrenyl group may be mentioned.

As the heteroaromatic ring group having 3 to 23 carbon atoms, for example, a pyridyl group, a pyrazinyl group, a pyrimidinyl group, a quinolyl group, an isoquinolyl group, a naphthyridinyl group, a quinoxalyl group, an indolyl group, a phenanthrolinyl group, a dibenzothienyl group, or a dibenzofuranyl group may be mentioned.

Among the aromatic hydrocarbon groups having 6 to 24 carbon atoms, in view of the sublimation property, a phenyl group and a naphthyl group, each of which has a relatively small molecular weight, are preferable.

Among the heteroaromatic ring groups having 3 to 23 carbon atoms, in view of the sublimation property and electronic influences, a pyridyl group, a pyrazinyl group, and a pyrimidinyl group, each of which has a relatively small molecular weight and also has an electron withdrawing property, are preferable.

The above $Ar_1$ to $Ar_4$ each may have a substituent. The substituent is any one selected from the group consisting of a cyano group, an alkyl group having 1 to 4 carbon atoms, an aromatic hydrocarbon group, such as a phenyl group, a tolyl group, a xylyl group, a mesityl group, or a cumenyl group, and a halogen atom, such as a fluorine atom, a chlorine atom, a bromine atom, or an iodine atom.

When the halogen atom is the substituent, a fluorine atom is preferable.

As the alkyl group having 1 to 4 carbon atoms, for example, a methyl group, an ethyl group, an n-propyl group, an iso-propyl group, an n-butyl group, an iso-butyl group, a sec-butyl group, or a tert-butyl group may be mentioned, and a methyl group or a tert-butyl group is preferable.

As the halogen atom represented by one of $R_1$ to $R_4$, for example, a fluorine atom, a chlorine atom, a bromine atom, or an iodine atom may be mentioned, and a fluorine atom is preferable.

As the alkyl group having 1 to 8 carbon atoms represented by one of $R_1$ to $R_4$, for example, a methyl group, an ethyl group, an n-propyl group, an iso-propyl group, an n-butyl group, an iso-butyl group, a sec-butyl group, a tert-butyl group, an n-pentyl group, an n-hexyl group, a cyclohexyl group, or an n-octyl group may be mentioned, and a methyl group or a tert-butyl group is preferable.

The phenyl group and the pyridyl group each represented by one of $R_1$ to $R_4$ each may have a substituent. This substituent is any one of a cyano group, a fluorine atom, a methyl group, and a tert-butyl group.

Properties of Organic Compound According to Present Disclosure

The organic compound according to the present disclosure has a base skeleton selected from the group consisting of dithiadiazafulvalene, dioxadiazafulvalene, dibenzodithiadiazafulvalene, dibenzodioxadiazafulvalene, benzodithiadiazafulvalene, and benzodioxadiazafulvalene. Since having an aromatic hydrocarbon group or a heteroaromatic ring group bonded to the nitrogen atom of the base skeleton, the organic compound according to the present disclosure has a high stability in the air. Although the base skeleton is liable to be oxidized and has a low stability, since the nitrogen atom functioning as a reaction active portion is covered with one of the above groups, the stability is improved.

In addition, those base skeletons are each a skeleton having a high electron injection property.

Since the organic compound according to the present disclosure has the two characteristics described above, the reactivity thereof with oxygen and moisture in the air is low, and hence, the atmospheric stability and the electron injection property can be simultaneously obtained.

As a compound having a high electron injection property, although an organic compound containing a metal may be mentioned, as a compound used for an organic electric-field element, an organic compound containing no metal is preferable. The advantage obtained by the use of the organic compound for an organic electric-field element is a low solubility to water. A compound, such as a known lithium fluoride or lithium quinolinol, containing an alkali metal has a high solubility to water. When the compound described above is used for an organic electric-field element, although an injection property from the electrode to the above compound can be obtained, this compound is easily ionized by moisture from the outside, and the degradation in stability of the element may be partially caused thereby.

Accordingly, by the use of an organic compound containing no metal, a highly stable element may be formed.

An electron injection material preferably has a shallow HOMO level and is closed to the energy level of the electrode. In this case, the "shallow HOMO level" indicates that the absolute value thereof is small, that is, the energy level thereof is closer to the vacuum level. In addition, the "shallow HOMO level" means approximately the same as a low first oxidation potential obtained by cyclic voltammetry (CV) measurement.

In a material having a shallow HOMO level as described above, the energy barrier of electrons injected from a cathode to an electron conduction level can be reduced. In order to function as the electron injection material, the first oxidation potential is preferably low to a certain extent, that is, in particular, the first oxidation potential is preferably 0 V or less (vs. Fc/Fc$^+$) and more preferably −0.8 V or less (vs. Fc/Fc$^+$). In addition, "vs. Fc/Fc$^+$" indicates that the potential is based on the oxidation-reduction potential of ferrocene.

In the organic light emitting element, when the HOMO level of the compound of the electron injection layer is shallower, in other words, when the first oxidation potential of the compound is lower, the electron injection property from the cathode to the electron injection layer is higher.

On the other hand, when the first oxidation potential of the organic compound is higher than the reduction potential of oxygen, the organic compound is stable against oxygen. That is, the first oxidation potential is preferably higher than the reduction potential of oxygen. Incidentally, the reduction potential ($O_2/O_2^-$) of oxygen is −1.22 V (vs. Fc/Fc$^+$) in a dimethylformamide (DMF) solvent. This has been disclosed in "Electoreduction of oxygen in aprotic media", Journal of Electroanalytical Chemistry 192, 69 to 74, (1995) by D. Vasudevan.

Hence, the first oxidation potential of the organic compound is preferably −1.20 to 0.00 V (vs. Fc/Fc$^+$) and more preferably −1.20 to −0.80 V (vs. Fc/Fc$^+$) in a DMF solvent. When the first oxidation potential is in the range described above, the stability against oxygen and excellent electron injection performance can be simultaneously obtained.

The oxidation potential can be measured by CV. In particular, the oxidation potential can be obtained from the oxidation current peak of CV.

The CV measurement was performed on example compounds A5 and AA9, each of which is one example of the organic compound according to the present disclosure. The CV measurement was performed in an N,N-dimethylformamide solution of 0.1 M tetrabutylammonium perchlorate. The measurement was performed under the conditions in which Ag/Ag$^+$ was used as a reference electrode, Pt was used as a counter electrode, glassy carbon was used as a working electrode, an oxidation-reduction potential Fc/Fc$^+$ of ferrocene was used as the reference potential, and the sweeping rate of the voltage was set to 0.5 V/s. When the measurement was performed using electrochemical analyzer Model1660C, manufactured by ALS, as a measurement apparatus, the first oxidation potentials estimated from the oxidation potential peaks of the example compounds A5 and AA9 were −1.05 V and −1.00 V, respectively. Since those potentials are within the range of −1.20 to 0.00 V, the organic compounds each can simultaneously satisfy the stability against oxygen and the electron injection performance.

In addition, since having a low oxidation potential, the example compounds A5 and AA9 each have a high donor property, and when a material having a high acceptor property is mixed therewith, a charge-transfer complex can be formed. When this charge-transfer complex is used for the organic compound layer in contact with the electrode of the organic light emitting element, carrier injection from the electrode can be easily performed.

On the other hand, after comparative compounds 3, 4, and 5 were left in the air, when the oxidation potentials thereof were measured, an oxidation potential peak at approximately −1.00 V was not observed, and hence it was found that the intrinsic properties of the above compounds were lost by oxidation. The comparative compound 3 is described in Non-Patent Literature 1 and is a compound in which a methyl group of 1-A of this specification is substituted by a hydrogen atom. The comparative compound 4 is described in Non-Patent Literature 1 and has the same structure as that of 1-B of this specification. The comparative compound 5 is described in Non-Patent Literature 2 and has the same structure as that of 1-C of this specification.

In addition, Non-Patent Literature 1 has disclosed that the compound 1-A is oxidized in the air and that the structure of the compound 1-B is rearranged by heat, and Non-Patent Literature 2 has disclosed that the compound 1-C is oxidized in the air. Accordingly, it is found that those compounds are unstable compounds in the air. Hence, those compounds are materials which are not suitably used for the organic light emitting element.

In order to confirm the reactivity of the organic compound according to the present disclosure with moisture in the air, the stability of each of those compounds against water was investigated. After powders of lithium fluoride and cesium fluoride, each of which contains an alkali metal, and a powder of the organic compound according to the present disclosure were left at room temperature and a high humidity of 95% for 1 hour, the results obtained thereby were then compared to each other. The confirmation was performed by visual inspection, and the results are shown in Table 1.

TABLE 1

| | Molecular Structure | Reactivity |
|---|---|---|
| Example Compound A5 | (structure with tBu groups, thiazole rings) | Not changed |
| Example Compound AA9 | (structure with tBu groups, benzothiazole rings) | Not changed |
| Comparative Compound 1 | LiF | Slightly deliquesced |
| Comparative Compound 2 | CsF | Deliquesced |

TABLE 1-continued

| | Molecular Structure | Reactivity |
|---|---|---|
| Comparative Compound 3 | 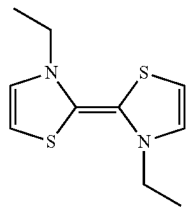 | Partially deliquesced and turned to black |
| Comparative Compound 4 | 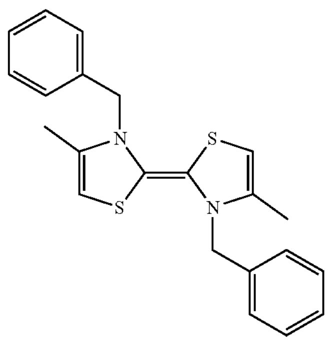 [SMILES: CC1=CS/C(=C2/SC=C(C)N2Cc2ccccc2)N1Cc1ccccc1] | Partially deliquesced and turned to black |
| Comparative Compound 5 | 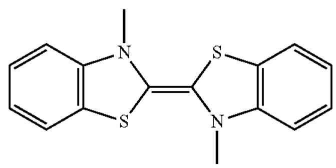 [SMILES: CN1/C(=C2\Sc3ccccc3N2C)Sc2ccccc21] | Partially deliquesced and turned to brown |

As shown in Table 1, the comparative compounds 1 to 5 deliquesced or oxidized.

On the other hand, the fulvalene compound according to the present disclosure was not changed, that is, for example, neither deliquescence nor oxidation occurred, and the stability thereof was confirmed.

The organic compound according to the present disclosure has a sufficient electron injection property as the electron injection material and is a compound which is not likely to be oxidized in the air.

The reason the stability of the fulvalene compound according to the present disclosure is improved is considered as follows.

The fulvalene compound according to the present disclosure is a compound in which the stability is improved by providing a bulky substituent for an unstable portion of a diazafulvalene skeleton.

First, the electron densities of portions of a dithiadiazafulvalene skeleton and a dibenzodithiadiazafulvalene skeleton were estimated using the molecular orbital calculation. The calculation procedure is as described below. For the calculation of the structures of molecules in the electron ground state and in the electronically excited state, Gaussian 09, which is a commercially available electron state calculation software, was used. In this case, as a quantum chemistry calculation method, the density functional theory was employed, and B3LYP was used as the functional. As the base function, 6-31G* was used.

Figure 1B:
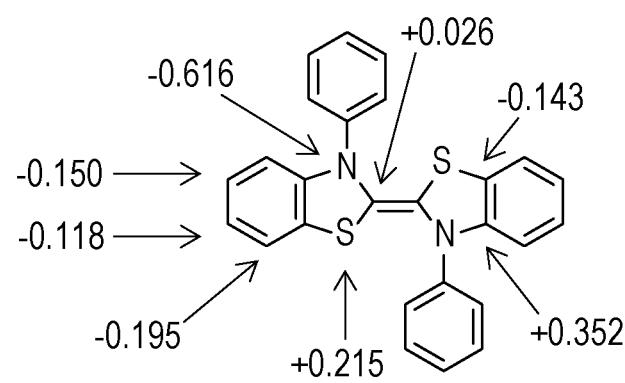

As shown in FIGS. 1A and 1B, the negative charge of the nitrogen atom which was considered to have a high activity was increased. Incidentally, the symmetric portions of the chemical structure had the same value.

From the results described above, it is believed that the nitrogen atoms, each of which has the highest negative charge, of the dithiadiazafulvalene skeleton and the dibenzodithiadiazafulvalene skeleton are responsible for the increase in instability.

The reason the comparative compounds 3, 4, and 5 are unstable in the air is believed that when an ethyl group, a benzyl group, or a methyl group is only provided for the nitrogen atom having a high negative charge, the excluded volume effect is not sufficient, and hence, reactions with moisture and/or oxygen in the air occur.

On the other hand, since having an aromatic hydrocarbon group or a heteroaromatic ring group, the fulvalene compound according to the present disclosure is a stable compound in the air.

In addition, it is found that the carbon atom adjacent to the sulfur atom of the dithiadiazafulvalene skeleton has a relatively large negative charge. Hence, in order to further improve the stability, it is preferable that a substituent having a large excluded volume as described above is provided for this substitution position, or a condensed ring is formed together with this carbon atom. In this case, the formation of the condensed ring indicates the formation of a larger heteroaromatic ring, such as an imidazolium ring or a benzimidazolium ring. That is, when the dithiadiazafulvalene skeleton and the dibenzodithiadiazafulvalene skeleton are compared to each other, since a carbon atom having a relatively large negative charge is not present, the dibenzodithiadiazafulvalene skeleton is more preferable.

Those described above can also be applied to the case of a dioxadiazafulvalene skeleton and a dibenzodioxadiazafulvalene skeleton.

In addition, as a method for further improving the stability of the organic compound according to the present disclosure, a method may be considered in which the bulk volume of a substituent provided for the nitrogen atom having a high activity is increased as much as possible so as to increase the excluded volume. As a method to increase the excluded volume, for example, the increase in number of carbon atoms of $Ar_1$ to $Ar_4$ and the introduction of bulky substituents to $Ar_1$ to $Ar_4$ may be mentioned.

However, when the number of carbon atoms of $Ar_1$ to $Ar_4$ is increased, although the excluded volume is increased, since the intermolecular stacking is increased, the sublimation property may be degraded in some cases. Hence, the excluded volume effect is preferably enhanced by providing substituents for $Ar_1$ to $Ar_4$. That is, in view of the excluded volume and the sublimation property, $Ar_1$ to $Ar_4$ are each preferably an aromatic hydrocarbon group having a relatively small molecular weight, such as 6 to less than 12 carbon atoms, or a heteroaromatic ring group having 6 to less than 12 carbon atoms and each preferably have at least one substituent.

As another method to improve the stability, a method in which an electron-withdrawing substituent is introduced may be mentioned. As the electron-withdrawing substituent, for example, a halogen atom, such as a fluorine atom, a cyano group, or a heteroaromatic ring group having an electron-withdrawing nitrogen atom may be mentioned. When at least one of those substituents is provided for at least one of $Ar_1$ to $Ar_4$ and $R_1$ to $R_4$, the oxidation potential of the organic compound becomes higher, and the difference thereof from the reduction potential of oxygen is increased; hence, it is preferable since the oxidation stability is improved. In addition, in the case in which at least one of $Ar_1$ to $Ar_4$ itself is a heteroaromatic ring group having an electron-withdrawing nitrogen atom, it is also preferable since the effect similar to that described above can be obtained.

As described above, by the use of a fulvalene compound having a low oxidation potential as the electron injection layer, a stable element having a high stability against water as compared to that obtained by using an alkali metal salt or an alkali metal can be provided.

By analysis of the organic compound layer of the organic light emitting element using time-of-flight secondary mass spectrometry (TOF-SIMS) or the like, whether the organic light emitting element contains the organic compound according to the present disclosure or not can be confirmed. The above analytical method is simply described by way of example, and a method in which after the organic compound is extracted from the organic light emitting element, analysis is performed using infrared rays (IR), ultraviolet rays (UV), nuclear magnetic resonance (NMR), or the like may also be performed.

Examples of Fulvalene Compound According to Present Disclosure

Hereinafter, concrete structural formulas of a dithiadiazafulvalene compound, a dioxadiazafulvalene compound, a dibenzodithiadiazafulvalene compound, a dibenzodioxadiazafulvalene compound, a benzodithiadiazafulvalene compound, and a benzodioxadiazafulvalene compound will be shown by way of example. However, the present disclosure is not limited to those concrete examples. In this case, "iPro" represents an iso-propyl group, and "tBu" represents a tert-butyl group.

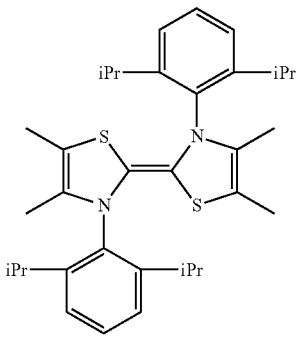

A1

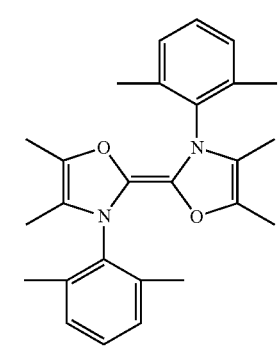

A2

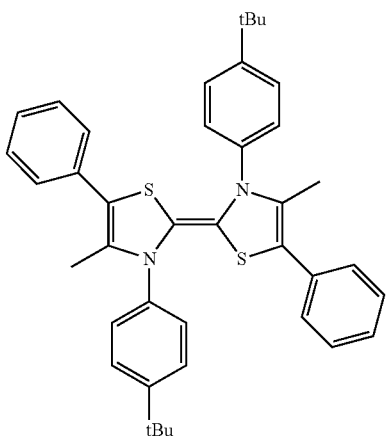

A3

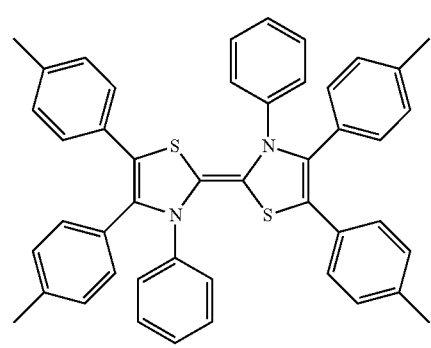

A4

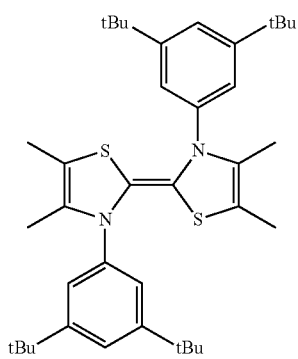

A5

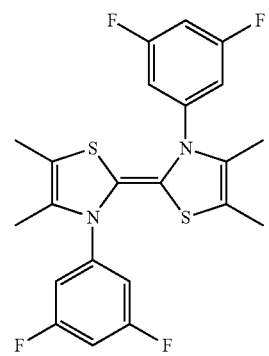

A6

A7
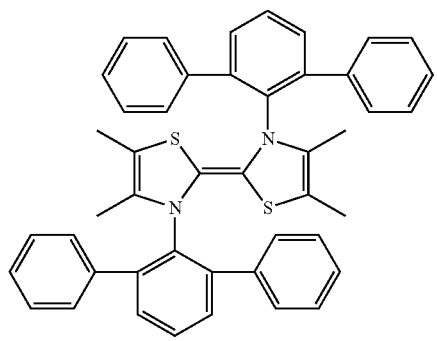
A8
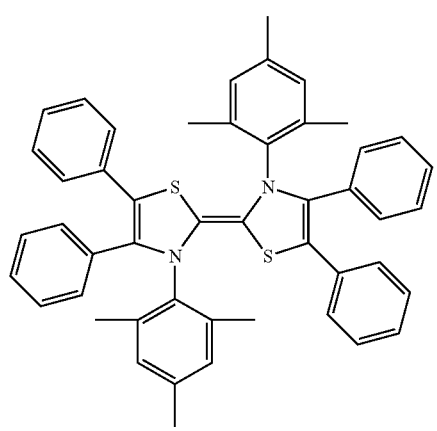
A9
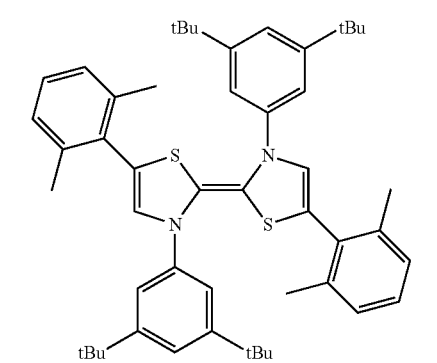
A10
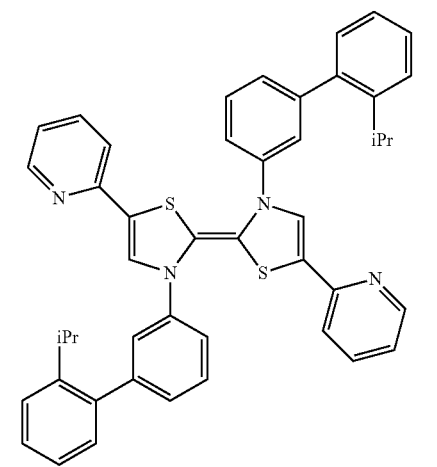
A11
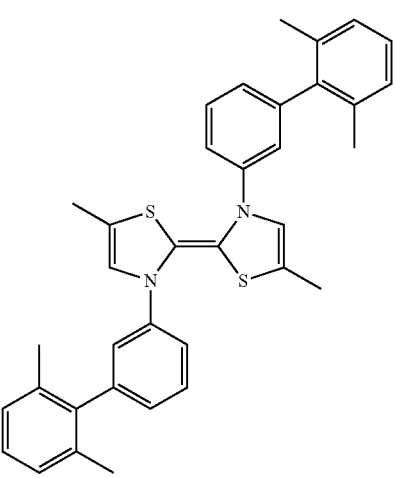
A12
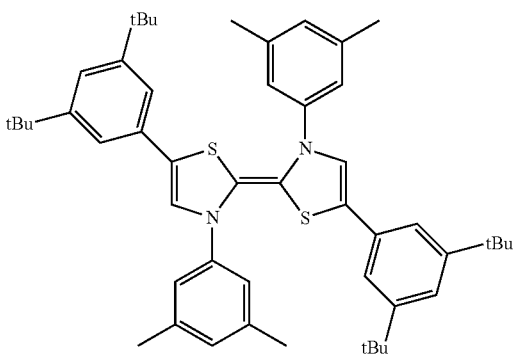
A13
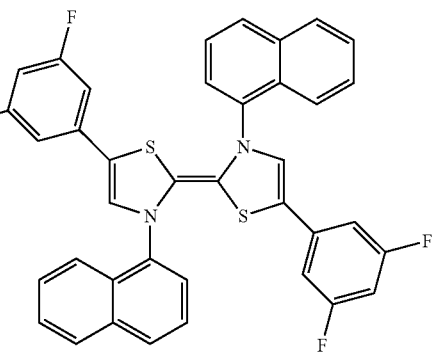

-continued
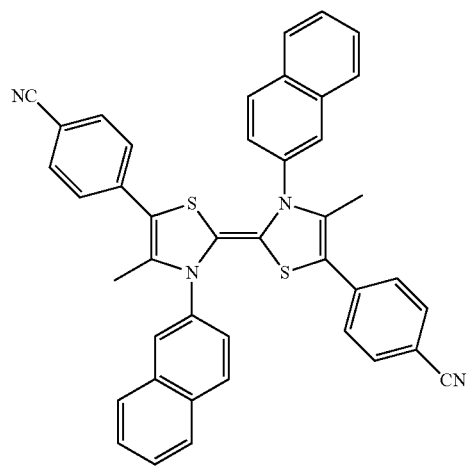
A14
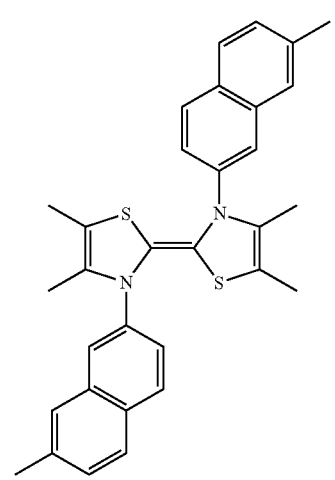
A15
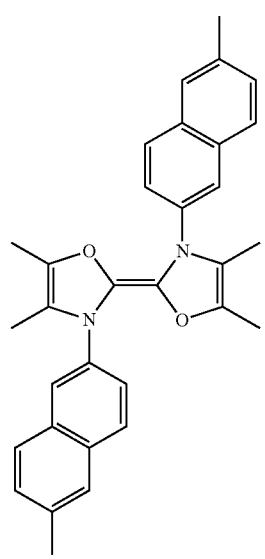
A16
-continued
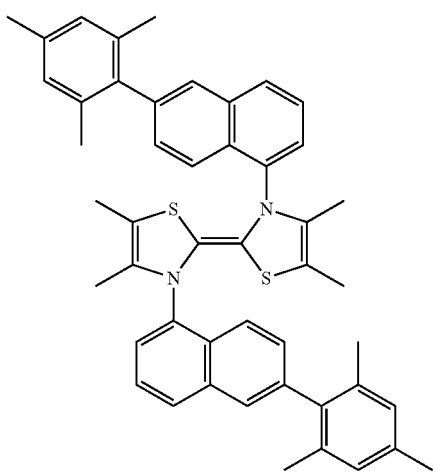
A17
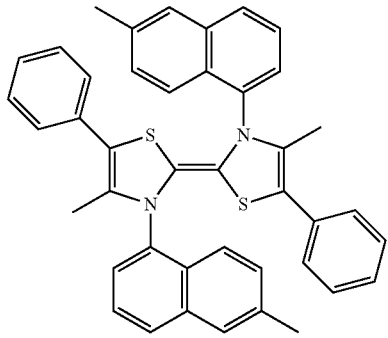
A18
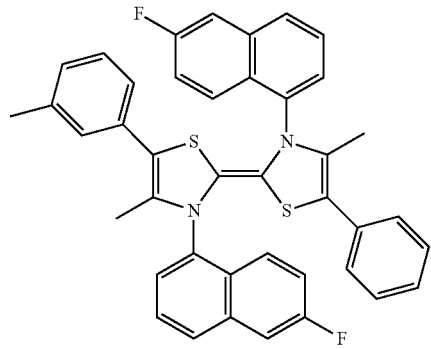
A19
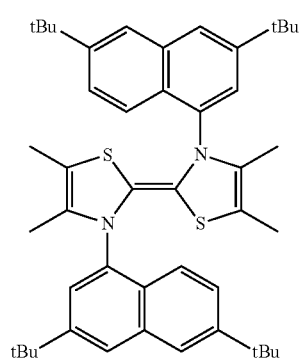
A20

B1
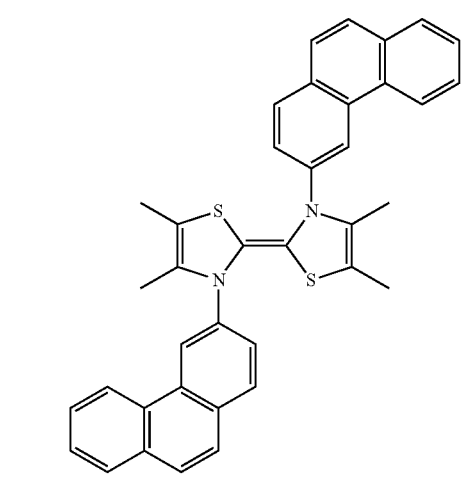
B2
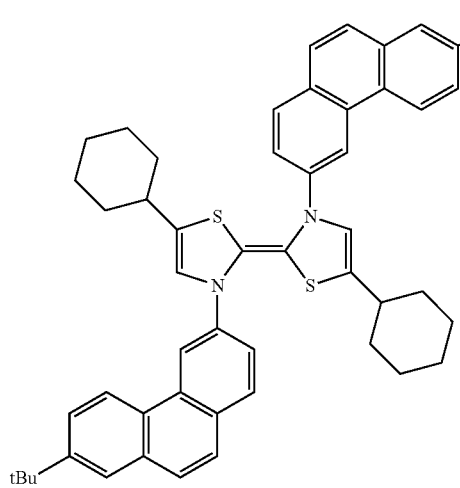
B3
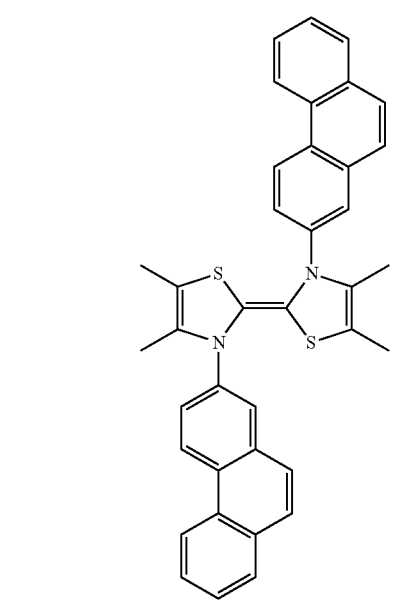
B4
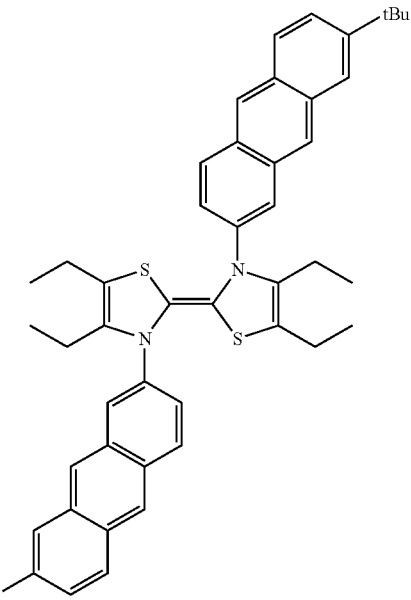
B5
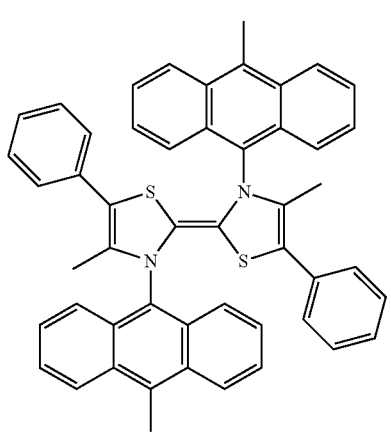
B6
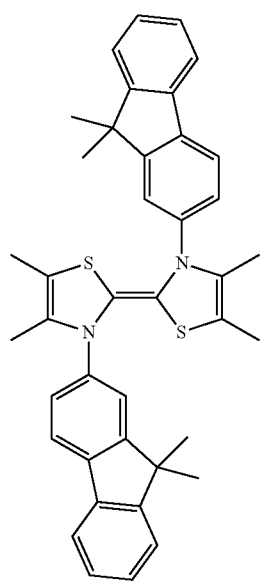

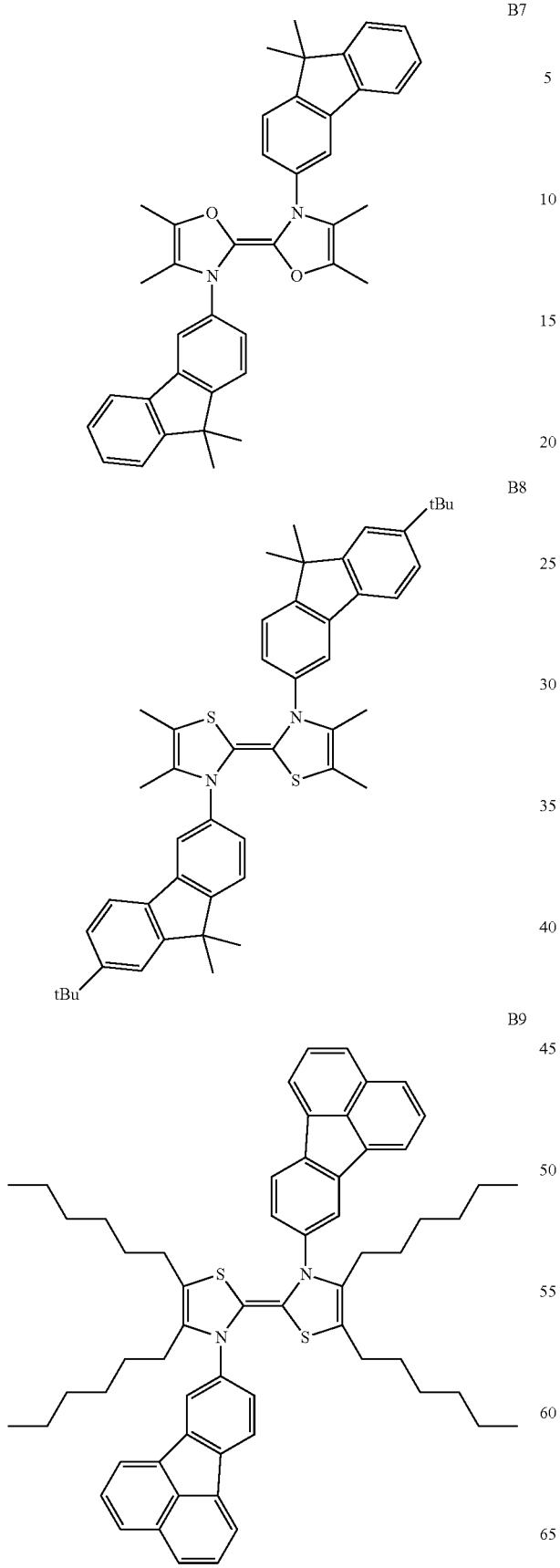
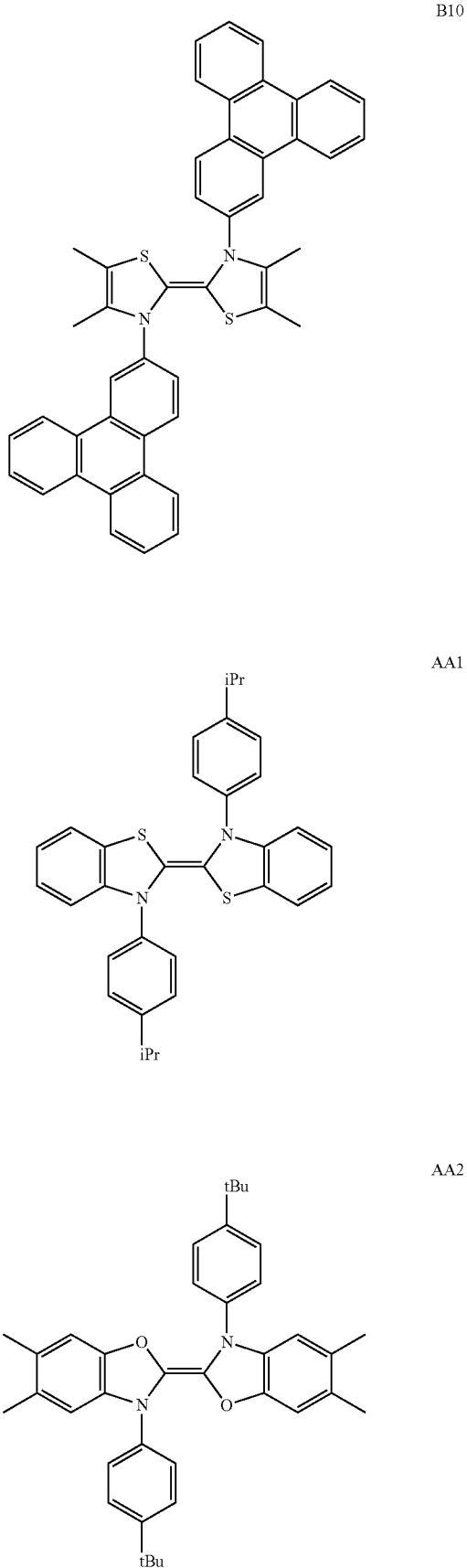

AA3 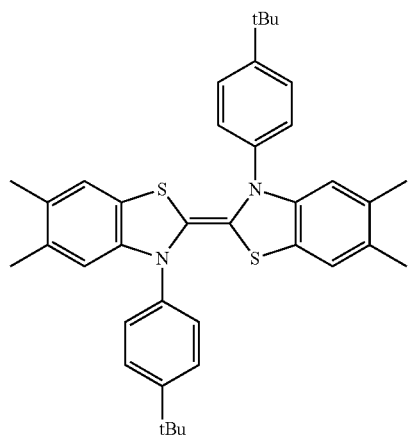
AA4 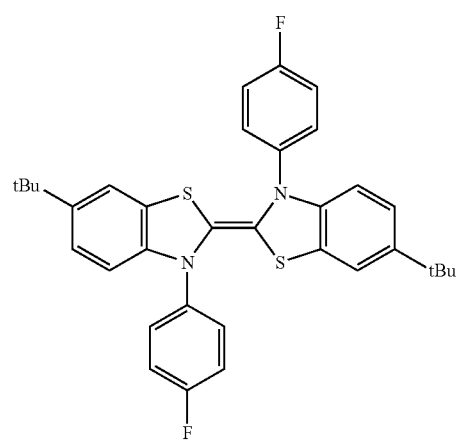
AA5 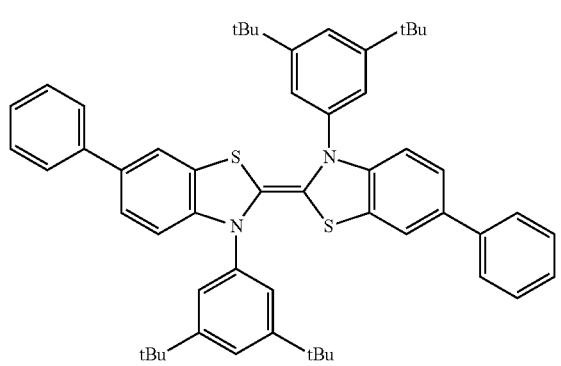
AA6 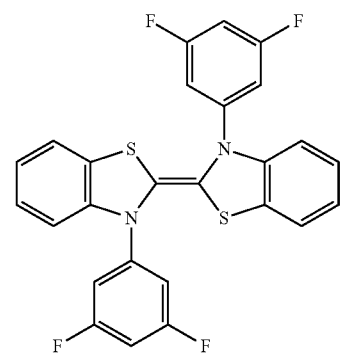
AA7 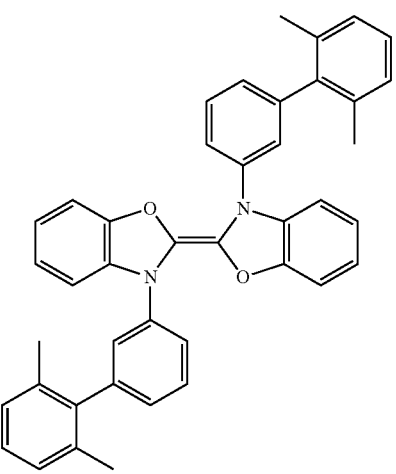
AA8 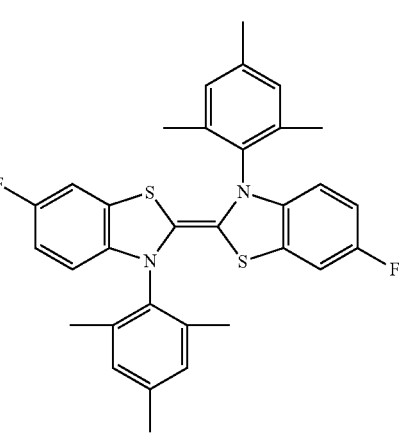
AA9 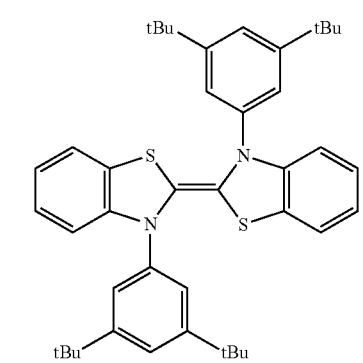
AA10 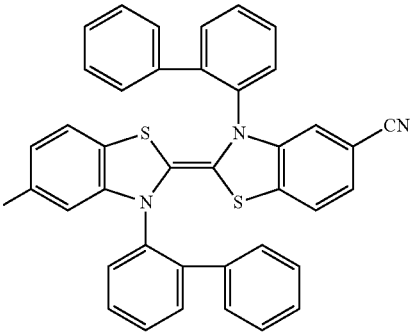

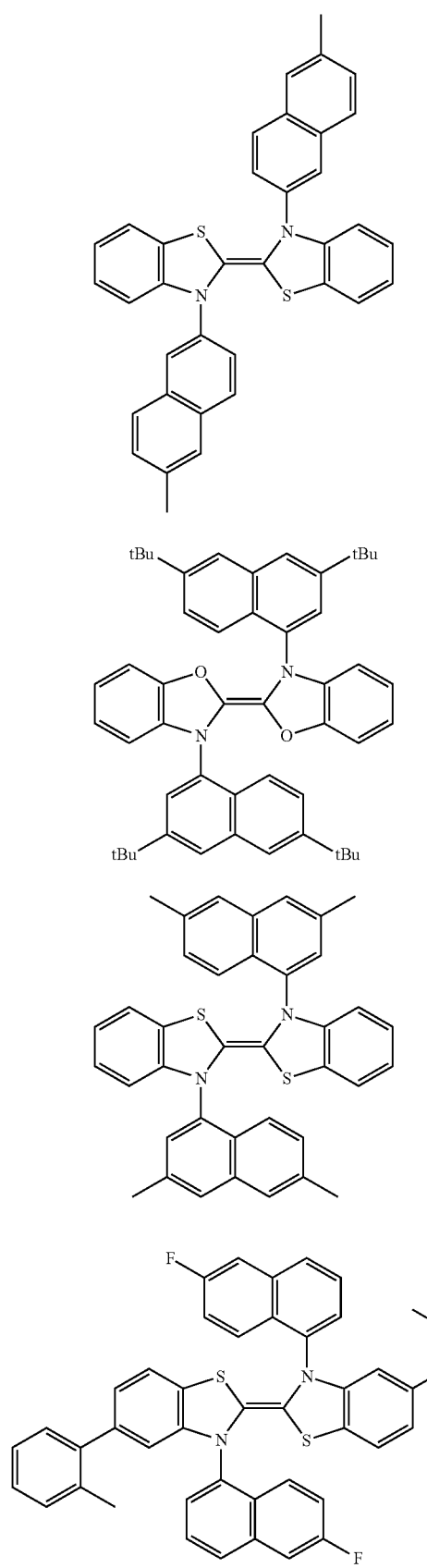
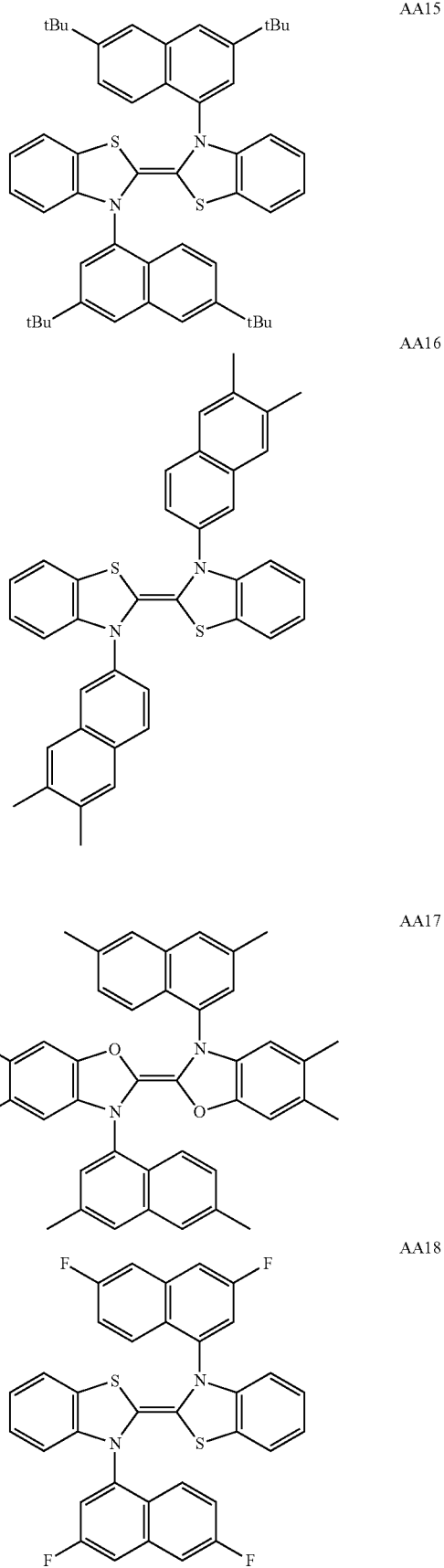

AA19
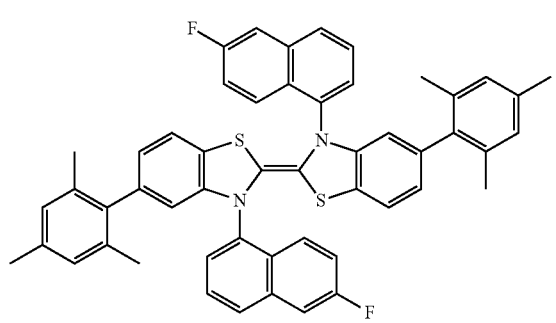
AA20
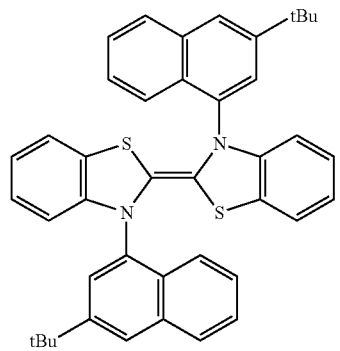
BB1
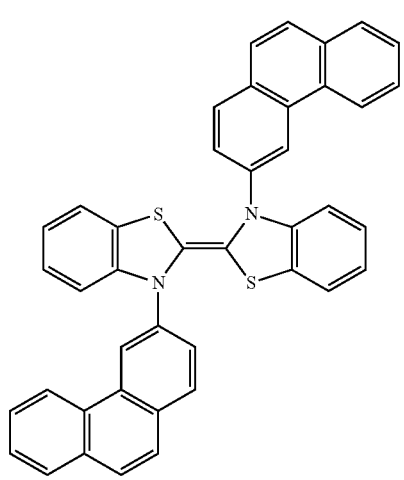
BB2
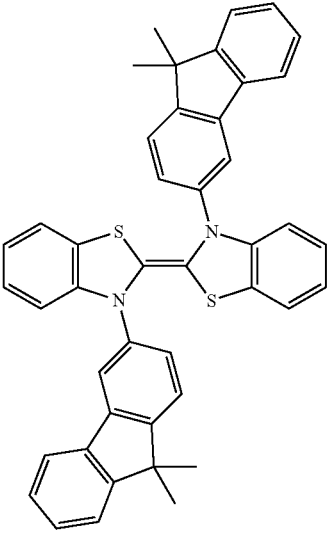
BB3
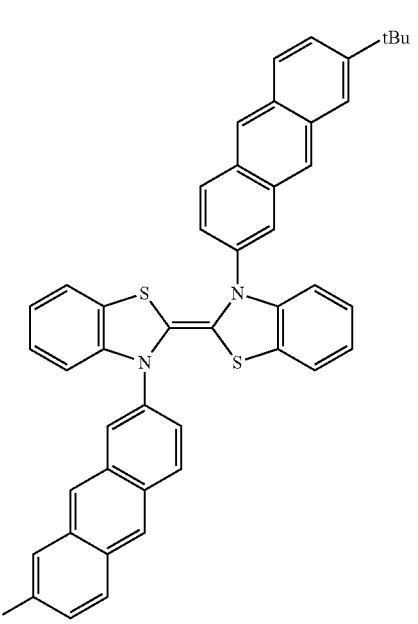
BB4
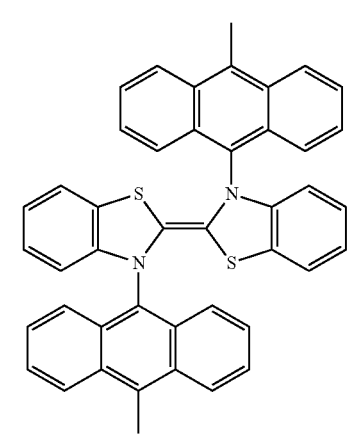
BB5

BB6 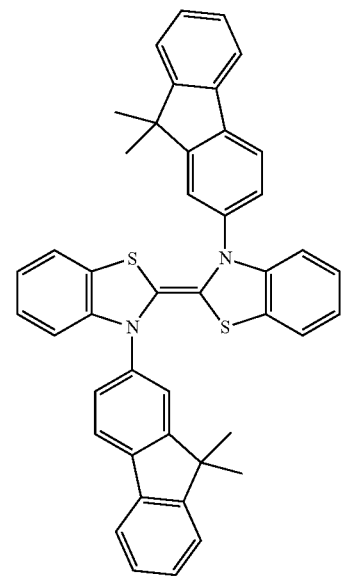
BB9 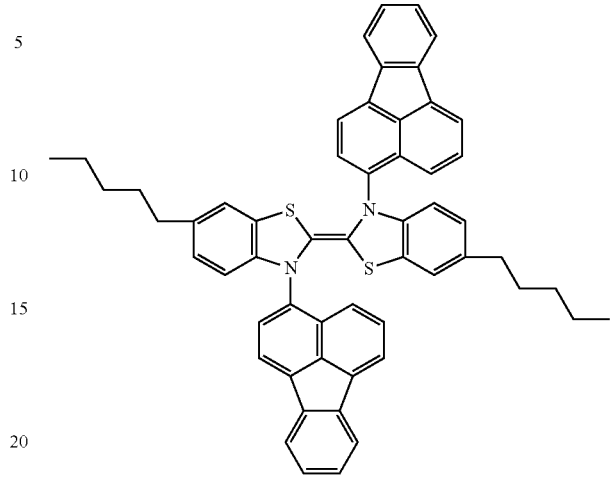
BB7 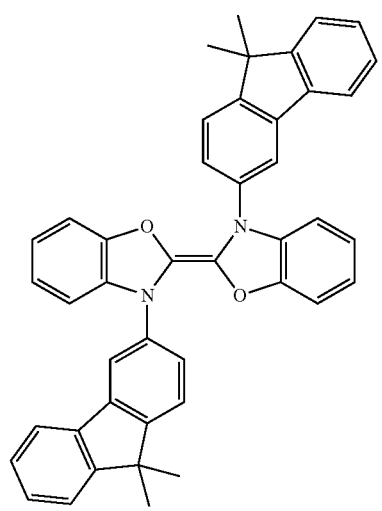
BB10 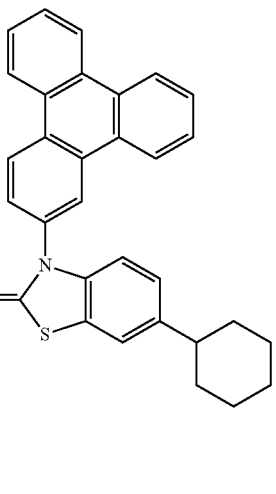
BB8 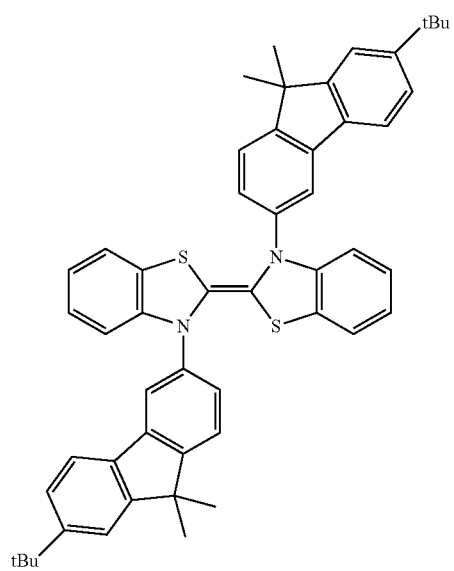
C1 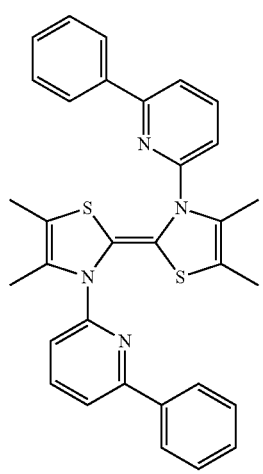

C2
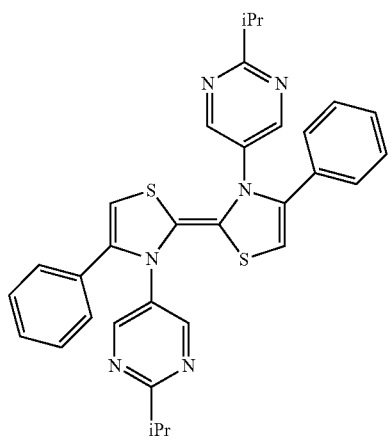
C3
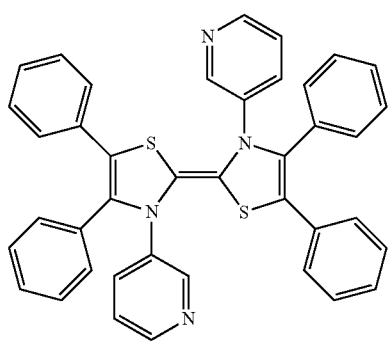
C4
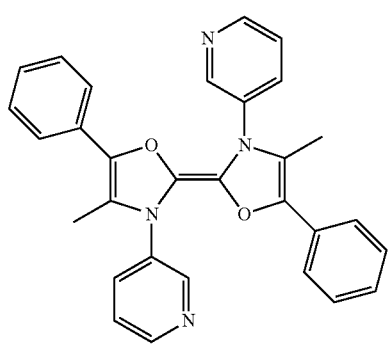
C5
C6
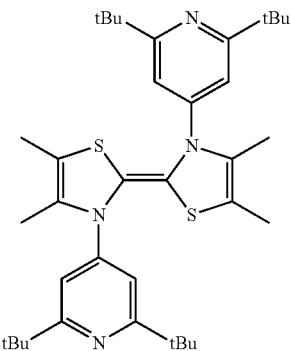
C7
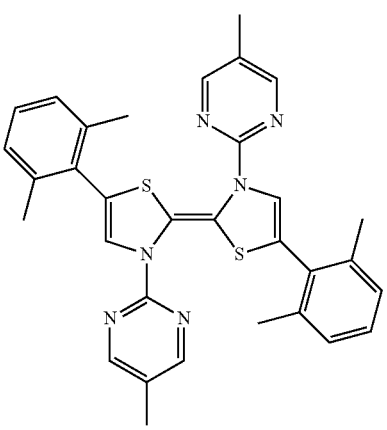
C8
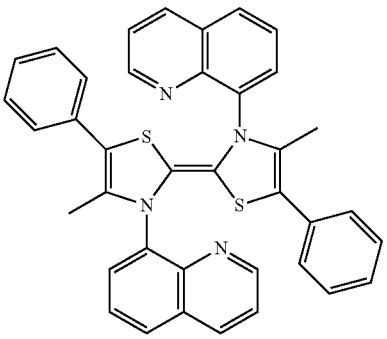
C9
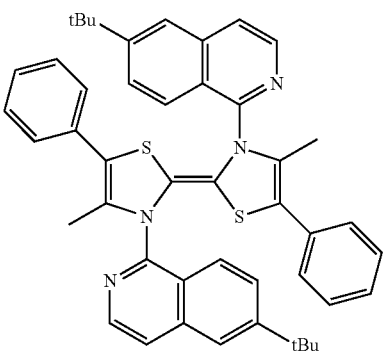

31
-continued
C10
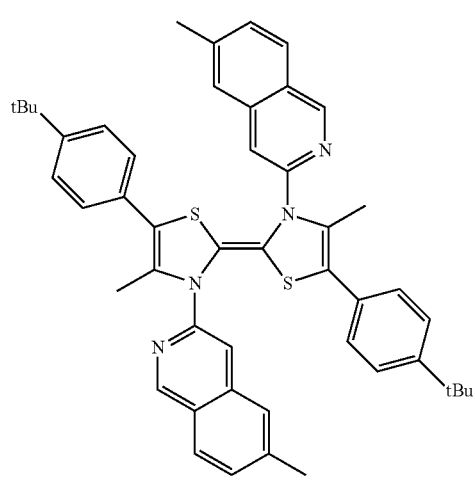
C11
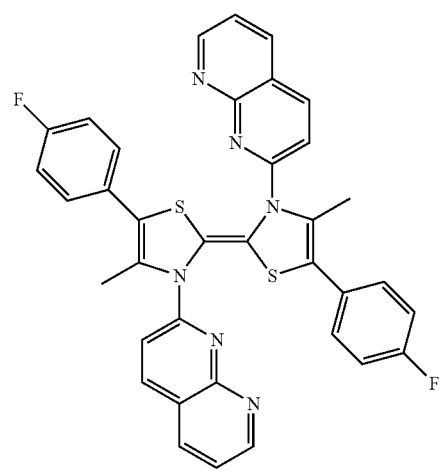
C12
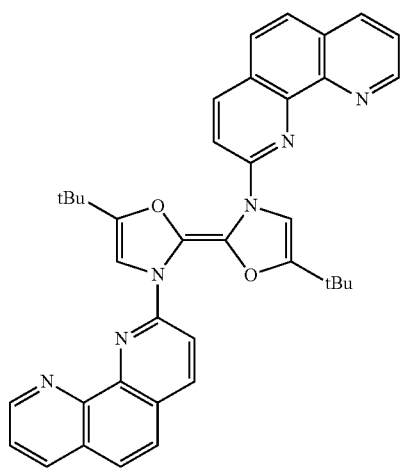
32
-continued
C13
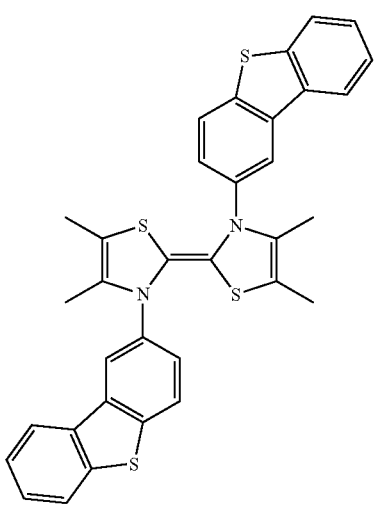
C14
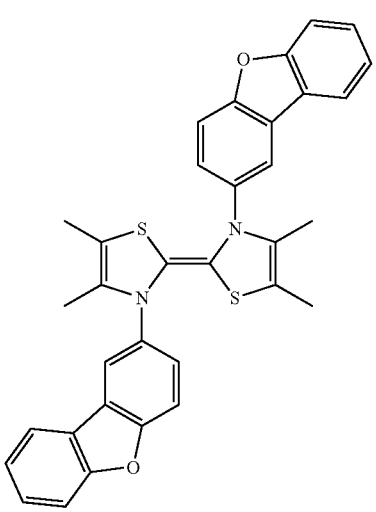
C15
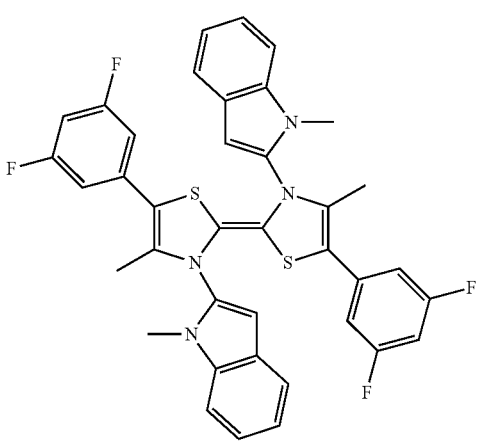

33
-continued
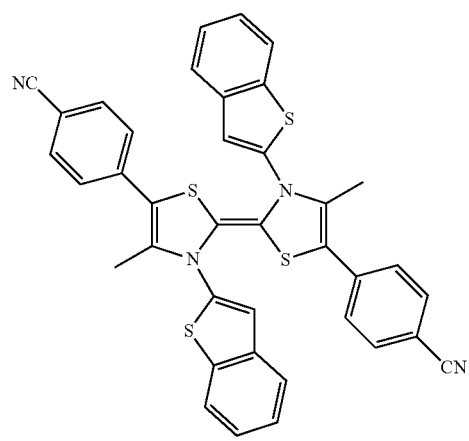
C16
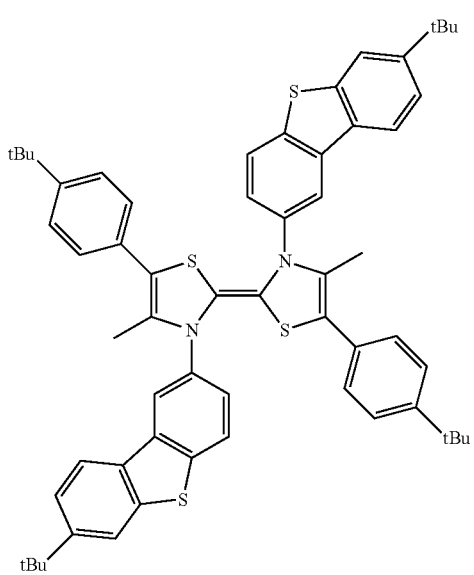
C17
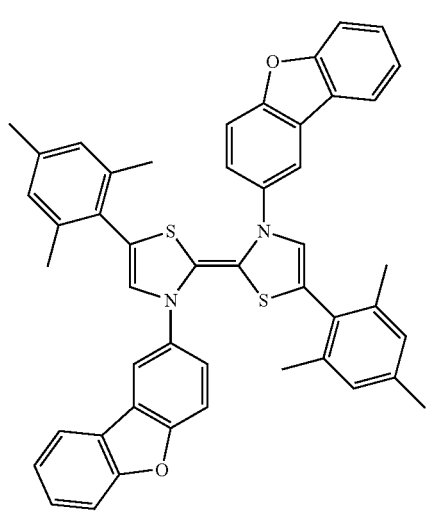
C18
34
-continued
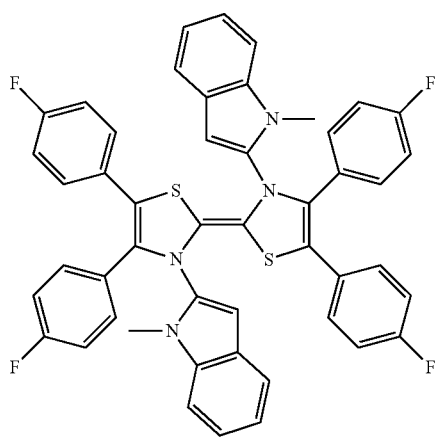
C19
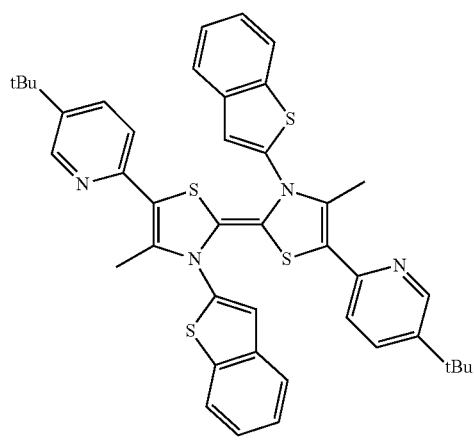
C20
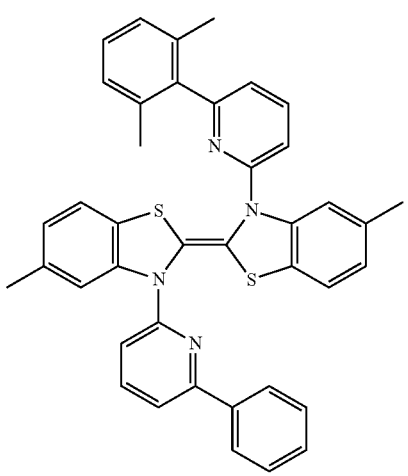
CC1

CC2
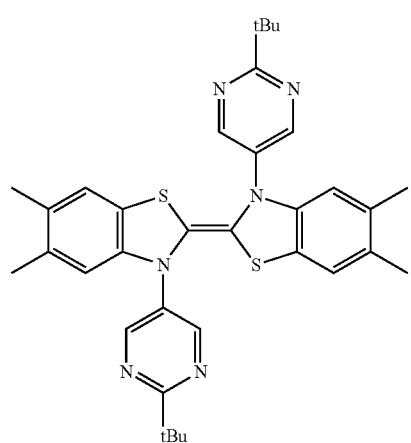
CC3
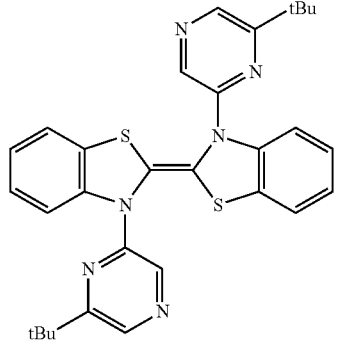
CC4
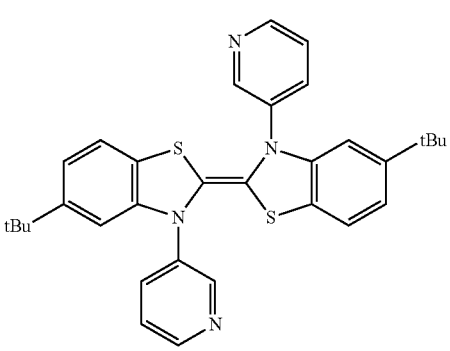
CC5
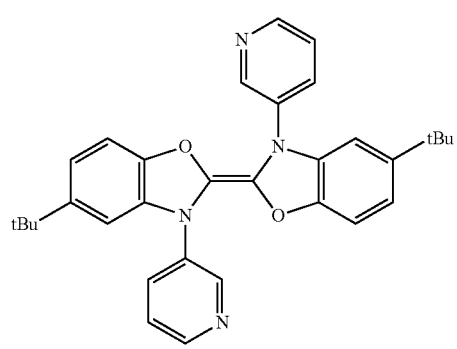
CC6
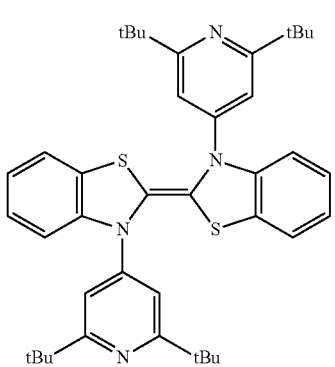
CC7
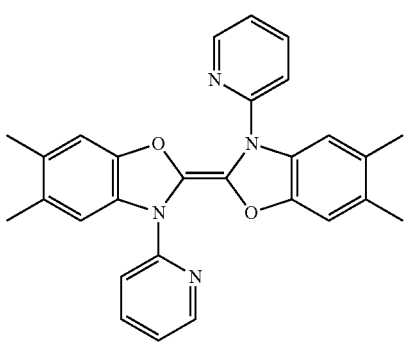
CC8
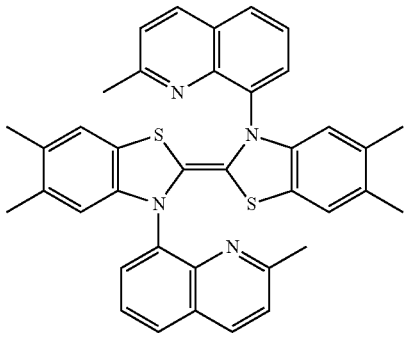
CC9
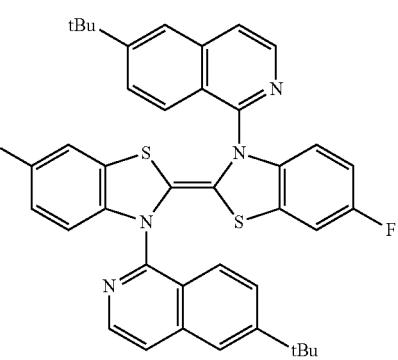

-continued
CC10
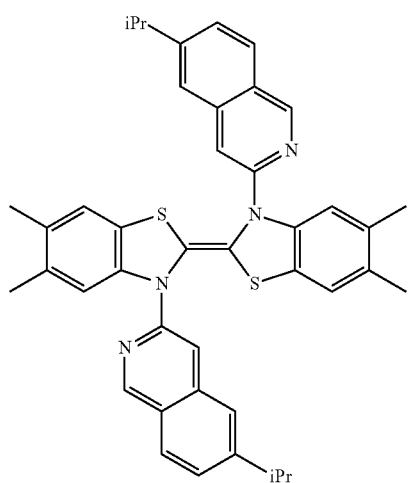
CC11
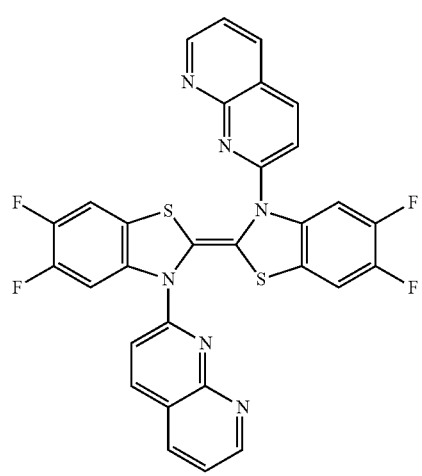
CC12
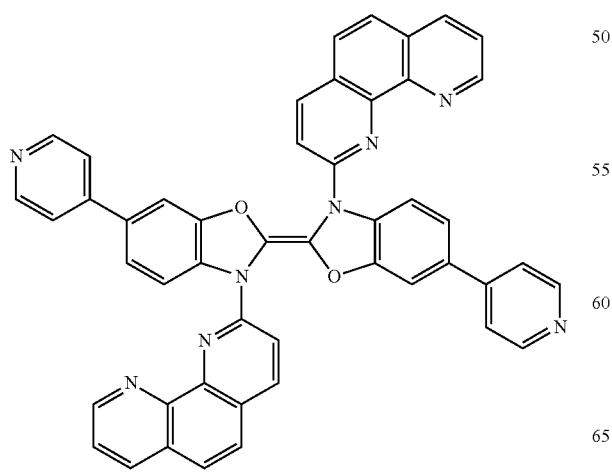
-continued
CC13
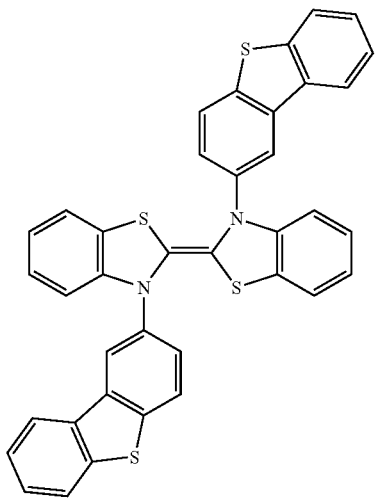
CC14
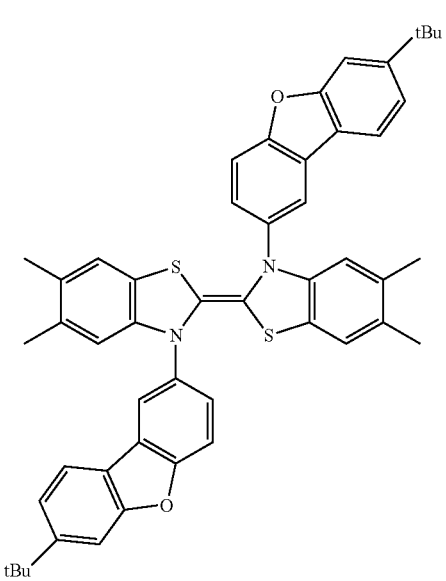
CC15
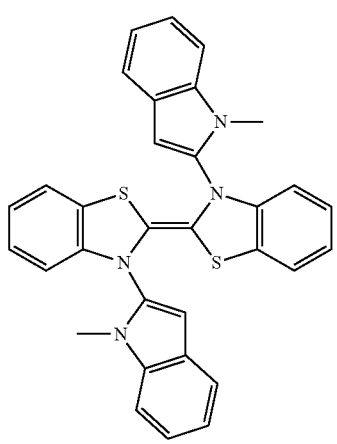

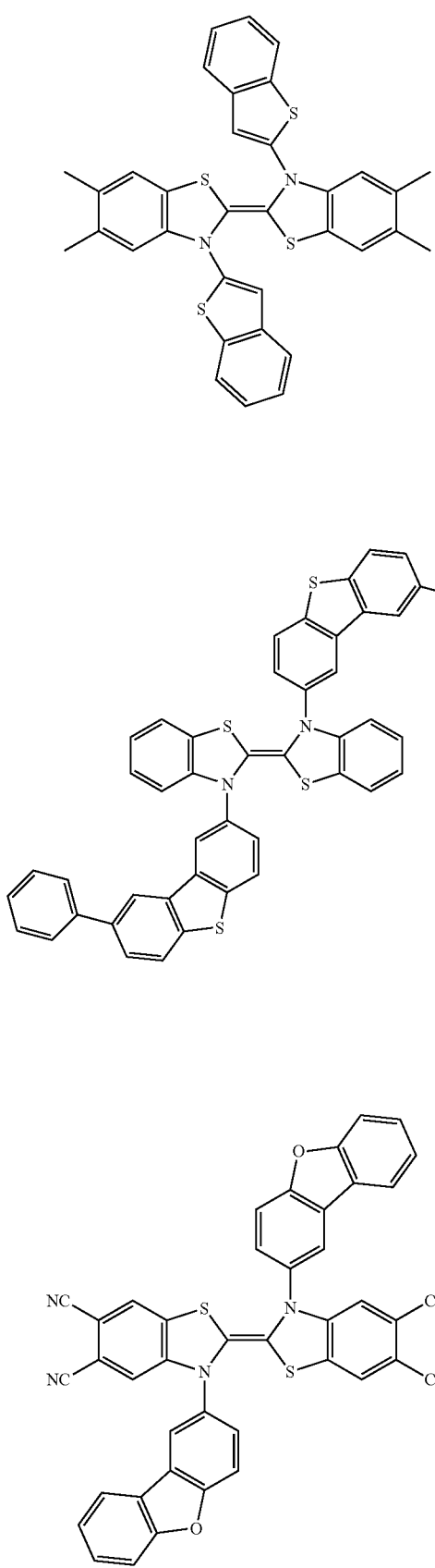
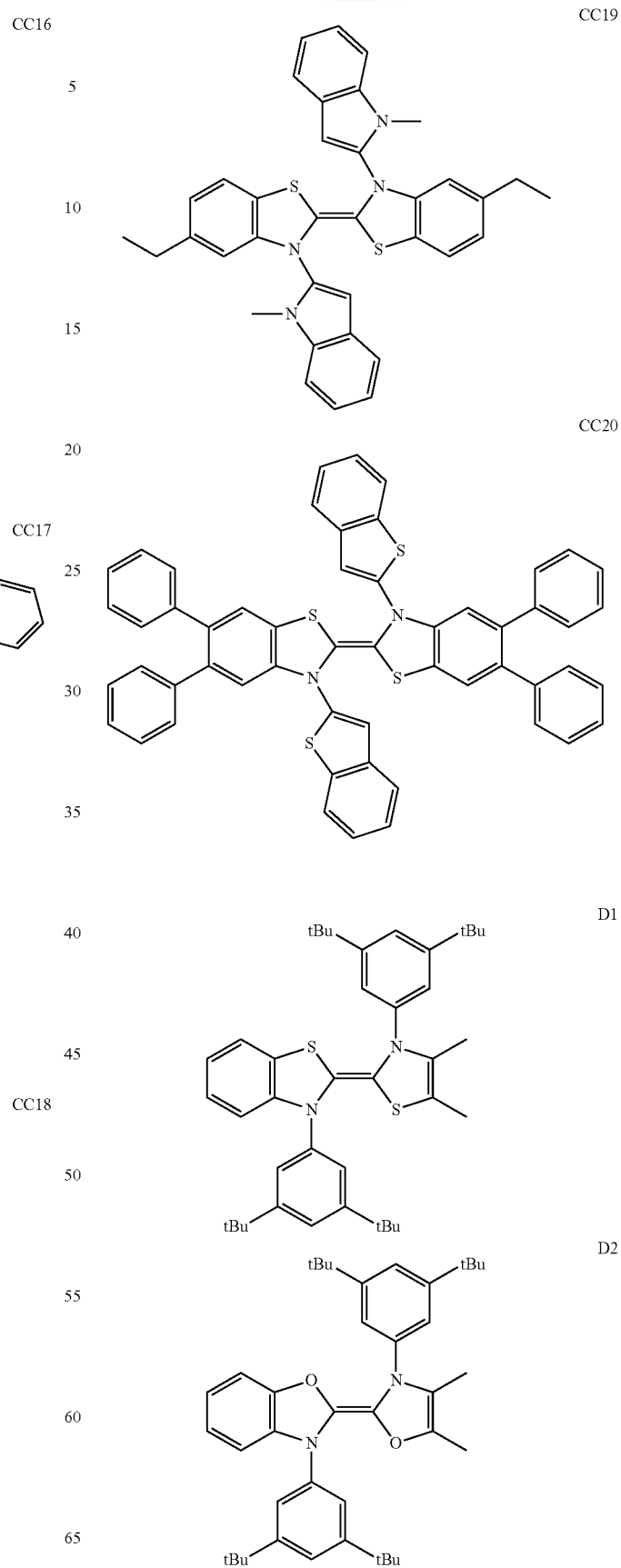

D3 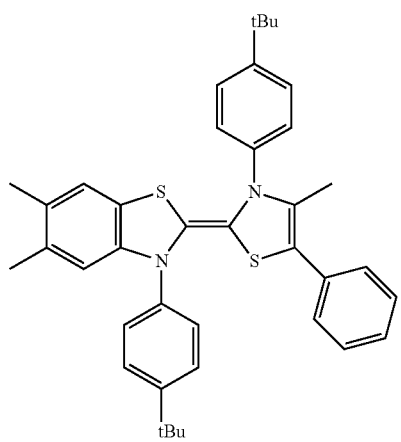

D4 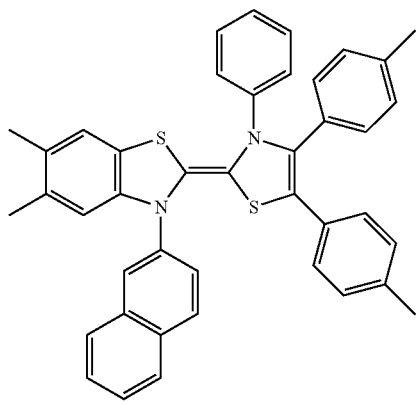

D5 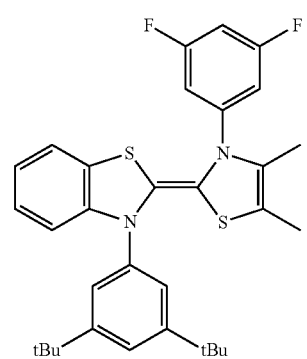

D6 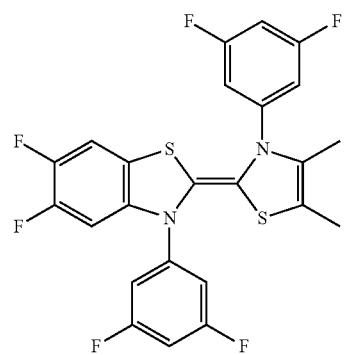

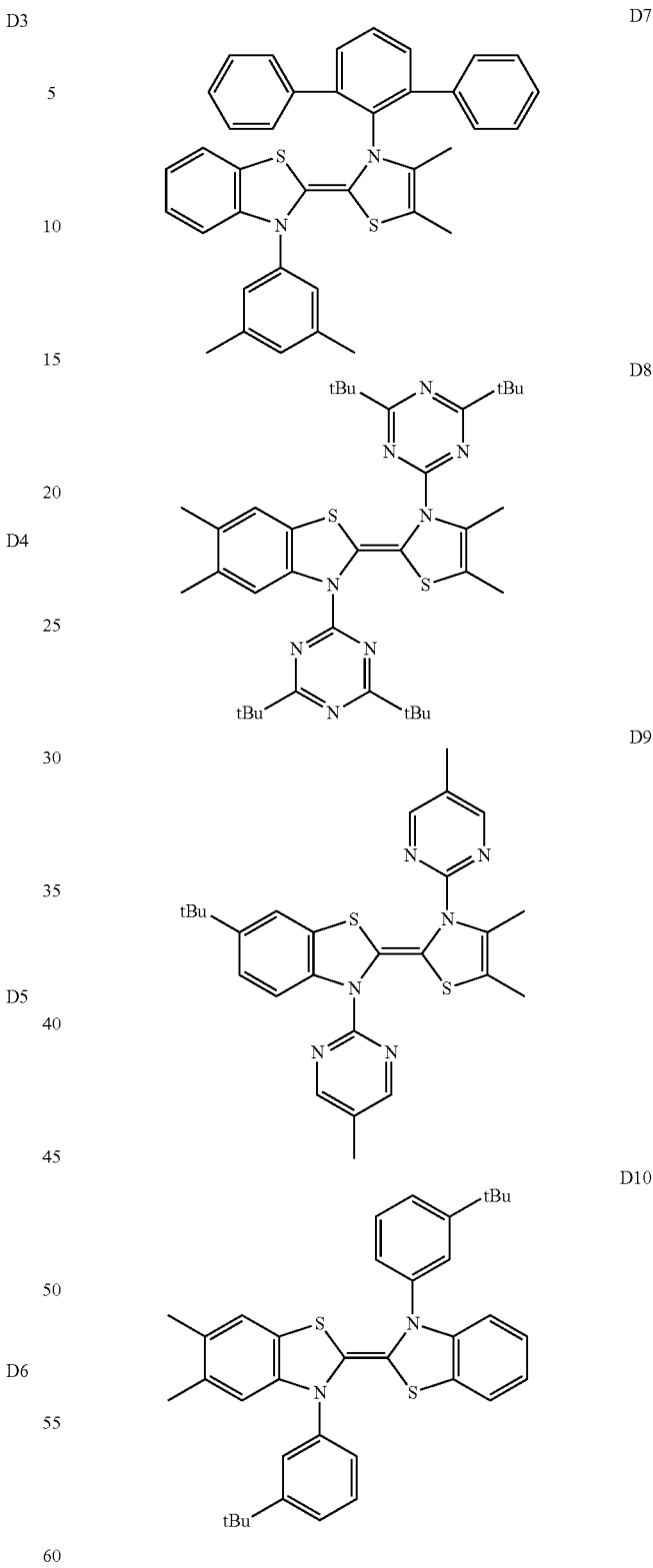

Among the compounds shown by way of example, the compounds shown in the group A and the group AA are compounds each of which has as $Ar_1$ to $Ar_4$ of the formulas [1] and [2], a phenyl group with or without at least one substituent or a naphthyl group with or without at least one substituent. Since a phenyl group or a naphthyl group is an aromatic hydrocarbon group having a relatively low molecular weight, in particular, the sublimation property is excellent. In addition, as shown in FIGS. 1A and 1B, when the group A and the group AA are compared to each other, since no carbon atom having a relatively large negative charge is present in the group AA, the group AA is superior in terms of the stability.

That is, the compounds shown in the group A and the group AA are compounds having stability against oxidation and an excellent sublimation property.

Among the compounds shown by way of example, the compounds shown in the group B and the group BB are compounds each of which has as $Ar_1$ to $Ar_4$ of the formulas [1] and [2], an aromatic hydrocarbon group having 12 to less than 24 carbon atoms with or without at least one substituent. Since the aromatic hydrocarbon group has a relatively high molecular weight, the vicinity of the nitrogen atom of the base skeleton is covered with a bulkier aromatic ring, and hence, in particular, the oxidation stability is excellent. In addition, as shown in FIGS. 1A and 1B, when the group B and the group BB are compared to each other, since no carbon atom having a relatively large negative charge is present in the group BB, the group BB is superior in terms of the stability.

That is, the compounds shown in the group B and the group BB are particularly superior compounds in terms of the oxidation stability due to the excluded volume effect.

Among the compounds shown by way of example, the compounds shown in the group C and the group CC are compounds each of which has as $Ar_1$ to $Ar_4$ of the formulas [1] and [2], a heteroaromatic ring group with or without at least one substituent. Since the heteroaromatic ring group is present, the nitrogen atom of the base skeleton has the stability not only by the excluded volume effect described above but also by the electronic influence. In addition, as shown in FIGS. 1A and 1B, when the group C and the group CC are compared to each other, since no carbon atom having a relatively large negative charge is present in the group CC, the group CC is superior in terms of the stability.

That is, the compounds shown in the group C and the group CC are particularly superior compounds in terms of the stability due to the electronic effect.

Figure 2:
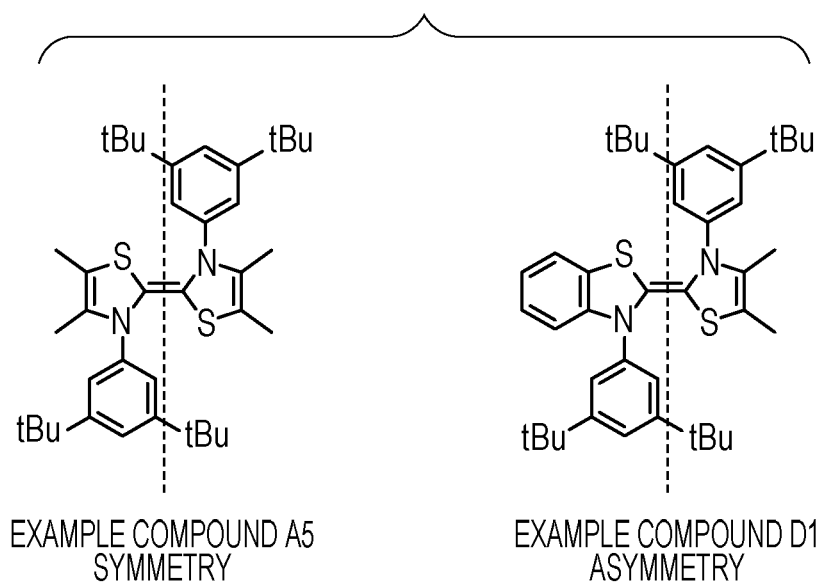
FIG. 2 is a view illustrating the symmetry of an organic compound using the fulvalene compound according to the present disclosure.

Among the compounds shown by way of example, the compounds shown in the group D are the compounds having an asymmetric structure. In this case, the symmetric structure indicates that as shown in FIG. 2, the symmetric planes are each present in a direction perpendicular to the molecular plane shown by a dotted line. On the other hand, in a molecule having an asymmetry structure and a low symmetric property as shown in the right side of FIG. 2, the molecular arrangement is liable to be disordered in thin film formation, and hence, the molecular packing is suppressed, and amorphous properties are enhanced.

That is, the compounds shown in the group D are compounds each of which imparts an excellent film quality in thin film formation.

Synthesis Method of Fulvalene Compound According to Present Disclosure

Next, a synthesis method of the fulvalene compound according to the present disclosure will be described.

As the organic compound according to the present disclosure, for example, a dithiadiazafulvalene compound may be synthesized in accordance with the following synthesis scheme. In this case, $P_1$ to $P_3$ each represent a substituent to be introduced.

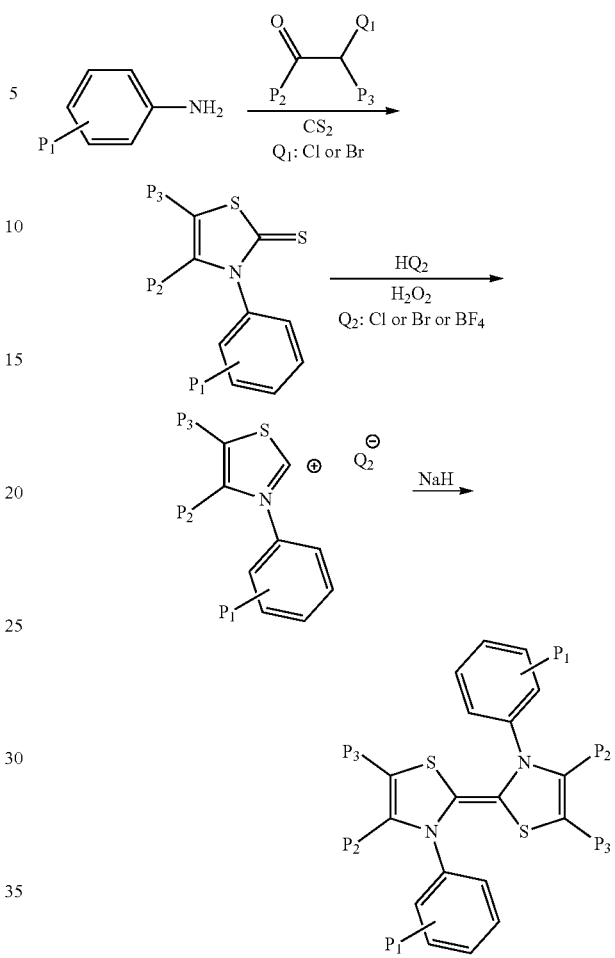

In particular, by sequentially performing the following reactions (1) to (3), the dithiadiazafulvalene compound is synthesized.

(1) A sulfide forming reaction by carbon disulfide and a cyclization reaction by an acid (2) An oxidation reaction by hydrogen peroxide and an acid (3) A reaction forming a carbene and an olefin by a strong base In addition, a dioxadiazafulvalene compound may be synthesized in accordance with the following synthesis scheme. In this case, $P_4$ to $P_6$ each represent a substituent to be introduced.

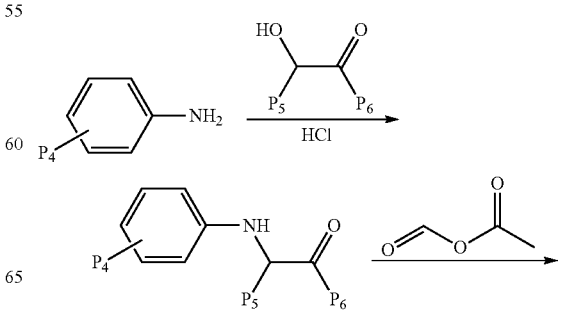

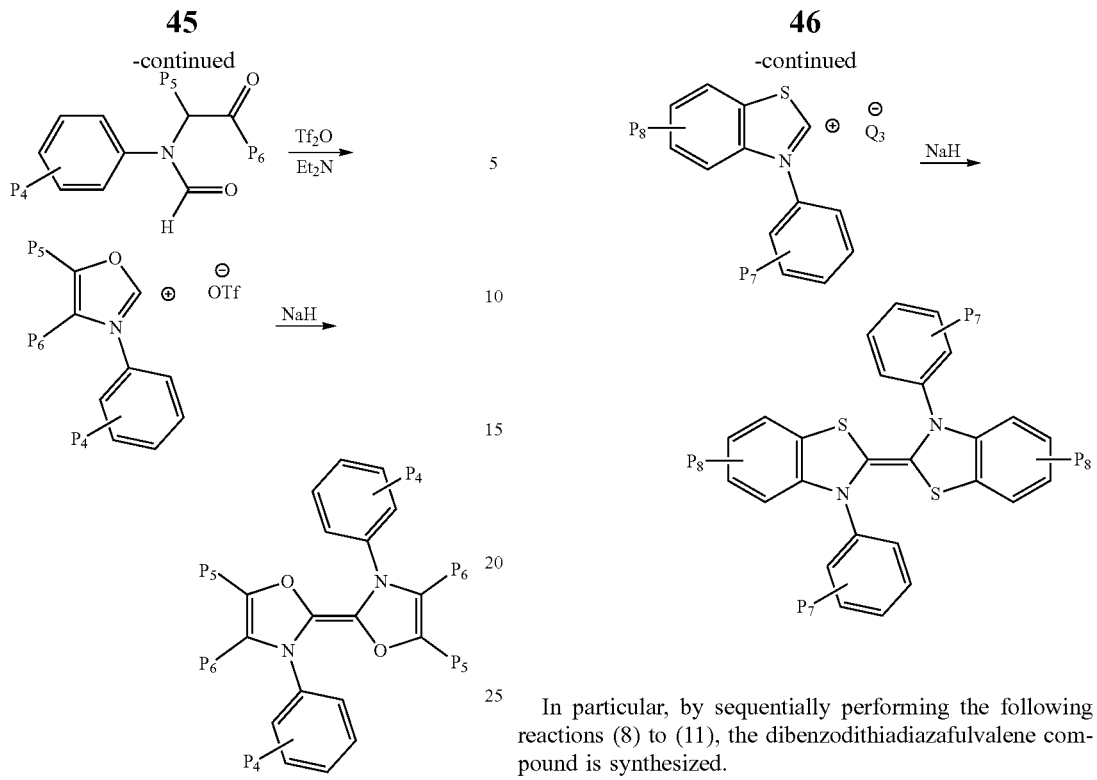

In particular, by sequentially performing the following reactions (4) to (7), the dioxadiazafulvalene compound is synthesized.
(4) A dehydration condensation reaction by an acid
(5) A formylation reaction by acetic formic anhydride
(6) A cyclization reaction by trifluoroacetic anhydride
(7) A reaction forming a carbene and an olefin by a strong base In addition, a dibenzodithiadiazafulvalene compound may be synthesized in accordance with the following synthesis scheme. In this case, $P_7$ and $P_8$ each represent a substituent to be introduced.

In particular, by sequentially performing the following reactions (8) to (11), the dibenzodithiadiazafulvalene compound is synthesized.
(8) A coupling reaction by a Pd catalyst
(9) A thiol formation reaction
(10) A cyclization reaction by an acid
(11) A reaction forming a carbene and an olefin by a strong base In addition, a dibenzodioxadiazafulvalene compound may be synthesized in accordance with the following synthesis scheme. In this case, $P_9$ and $P_{10}$ each represent a substituent to be introduced.

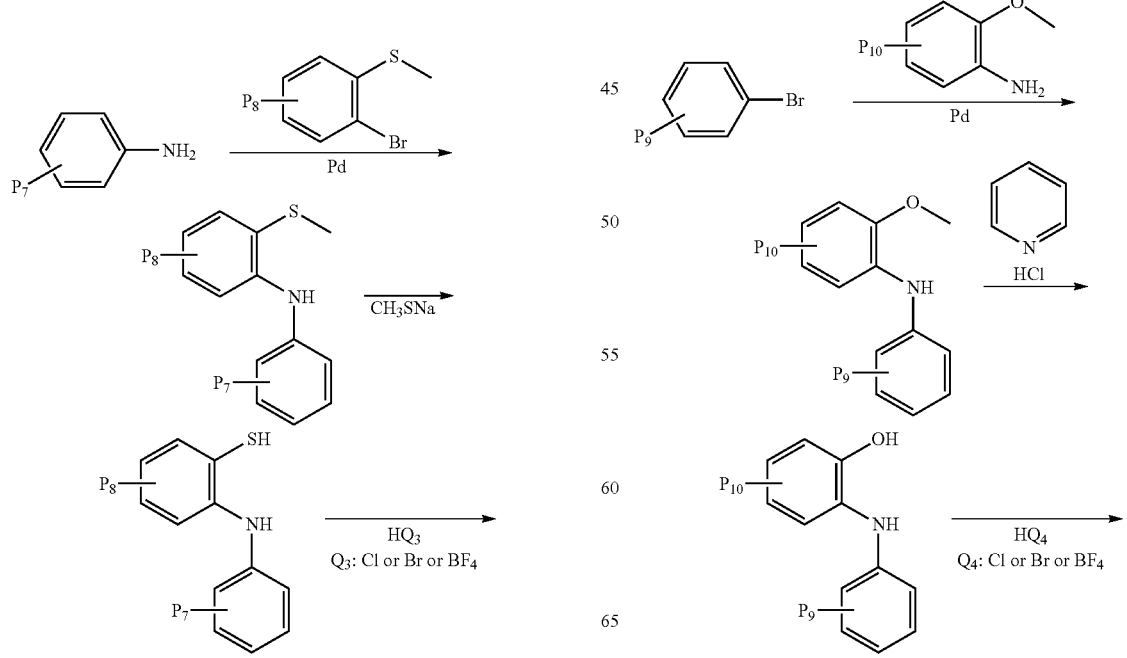

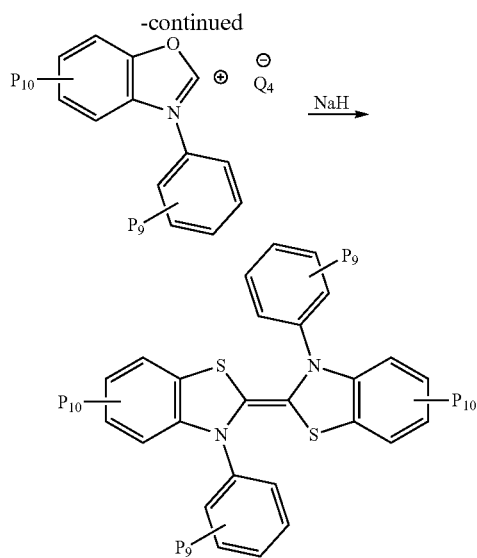
-continued

In particular, by sequentially performing the following reactions (12) to (15), the dibenzodioxadiazafulvalene compound is synthesized.
(12) A coupling reaction by a Pd catalyst
(13) A phenol formation reaction
(14) A cyclization reaction by an acid
(15) A reaction forming a carbene and an olefin by a strong base (Organic Electronic Element According to Embodiment)

An organic electronic element according to this embodiment is an organic electronic element having a pair of electrode and an organic compound layer disposed therebetween and is an organic electronic element characterized in that the organic compound layer is formed of the organic compound represented by the general formula [1].

As the organic electronic element according to this embodiment, for example, an organic light emitting element, an organic transistor, or an organic solar cell may be mentioned. The organic compound layer may be formed of a single layer or a plurality of layers, and the organic compound represented by the general formula [1] may be used for any layer of the organic compound layer.

The organic light emitting element according to this embodiment is an organic light emitting element having an anode, a cathode, and a light emitting layer disposed therebetween and has an organic compound layer between the cathode and the light emitting layer, and this organic compound layer is formed of the organic compound represented by the general formula [1]. The organic compound layer is preferably in contact with the cathode.

In the organic light emitting element of this embodiment, at least one layer disposed between the cathode and the light emitting layer contains the fulvalene compound according to the present disclosure.

In this case, the organic compound layer disposed between the cathode and the light emitting layer is also called an electron transport layer or an electron injection layer, and in particular, the organic compound layer in contact with the cathode is also called an electron injection layer.

As the element structure of the organic light emitting element according to this embodiment, an element structure having the following organic compound layers on a substrate may be mentioned. Among the organic compound layers, a layer containing a light emitting material is the light emitting layer. The organic compound layer may be formed of a single layer or a plurality of layers.

The organic light emitting element according to this embodiment may have, besides the light emitting layer, a hole injection layer, a hole transport layer, an electron blocking layer, a hole blocking layer, an electron transport layer, an electron injection layer, and the like. In addition, the light emitting layer may be either a single layer or a laminate formed of a plurality of layers.

As the structure of the organic light emitting element, for example, the following structures may be mentioned.
(1) anode/light emitting layer/cathode
(2) anode/hole transport layer/light emitting layer/electron transport layer/cathode
(3) anode/hole transport layer/light emitting layer/electron transport layer/electron injection layer/cathode (4) anode/hole injection layer/hole transport layer/light emitting layer/electron transport layer/cathode
(5) anode/hole injection layer/hole transport layer/light emitting layer/electron transport layer/electron injection layer/cathode
(6) anode/hole transport layer/electron blocking layer/light emitting layer/hole blocking layer/electron transport layer/cathode However, those examples of the element structure are quite basic element structures, and the structure of the organic light emitting element using the compound according to the present disclosure is not limited thereto.

In addition, among the above element structures, the structure (6) having both the electron blocking layer and the hole blocking layer is preferably used. In the structure (6), since both carriers, that is, holes and electrons, can be confined in the light emitting layer, a light emitting element having no carrier leakage and a high light emission efficiency can be obtained.

In addition, various layer structures may be formed, that is, for example, an insulating layer is provided on the interface between the electrode and the organic compound layer, an adhesive layer or an interference layer is provided, the electron transport layer or the hole transport layer is formed of two layers having different ionization potentials, and the light emitting layer is formed of two layer using different light emitting materials.

The organic light emitting element according to this embodiment may be either a bottom emission type in which light is extracted from an electrode at a substrate side or a top emission type in which light is extracted from a side opposite to the substrate, and may also be used as a double-side extraction structure.

In the organic light emitting element according to this embodiment, although the organic compound layer disposed between the cathode and the light emitting layer contains the organic compound represented by the general formula [1], the organic compound represented by the general formula [1] may also be used for another organic compound layer.

In particular, the fulvalene compound according to the present disclosure may be contained in any one of the hole injection layer, the hole transport layer, the electron blocking layer, the hole blocking layer, the electron transport layer, the electron injection layer, and the like. The organic compound according to this embodiment is preferably contained in the electron injection layer.

The organic compound according to the present disclosure may be used alone but is preferably used together with a different type compound different therefrom. The different type compound different from the organic compound according to the present disclosure is a compound different from the fulvalene compound represented by the general formula [1].

The weight rate of the different type compound is preferably more than 0 to 80 percent by weight when the total of the organic compound layer disposed between the cathode and the light emitting element layer is assumed to be 100 percent by weight. For example, the case in which the electron transport layer and the electron injection layer are provided between the cathode and the light emitting layer will be described by way of example. When the total of the electron injection layer is assumed to be 100 percent by weight, the weight rate of the different type compound different from the organic compound layer according to the present disclosure is more than 0 to 80 percent by weight. The electron transport layer is not included in the total. In addition, when the total of the organic compound according to the present disclosure and the different type compound is assumed to be 100 percent by weight, the weight rate of the different type compound may be more than 0 to 80 percent by weight.

When the organic compound layer of the organic light emitting element is analyzed using TOF-SIMS or the like, the weight rate of the compound can be obtained, and whether the organic light emitting element has the organic compound according to the present disclosure or not can be confirmed. The above analysis is described by way of example, and a method may also be used in which after the organic compound is extracted from the organic light emitting element, analysis is performed using IR, UV, NMR, or the like.

The different type compound is preferably a compound having a high oxidation potential as compared to that of the organic compound according to the present disclosure.

The different type compound is preferably one of an anthraquinone derivative, a fluorene derivative, a naphthalene derivative, an indene derivative, a terphenyl derivative, an acenaphthofluoranthene derivative, an indenoperylene derivative, and a phenanthroline derivative.

The light emitting layer of the organic light emitting element according to this embodiment may be formed of at least two types of components, and the components may be categorized into a primary component and an auxiliary component. The primary component is a compound having the maximum weight rate among all the compounds forming the light emitting layer and may be called a host material. The host material is a compound present as a matrix around a guest material in the light emitting layer and is a compound primarily responsible to transport carriers and to impart excited energy to the guest material.

The auxiliary component is a compound other than the primary component. The auxiliary component may be called a guest material, a light emitting assist material, or a charge injection material. The guest material may also be called a dopant material. The light emitting assist material and the charge injection material may be either organic compounds having the same structure or organic compounds having different structures. Although functioning as the auxiliary components, those organic compounds may also be called a host material 2 so as to be distinguished from the guest material.

In this case, the guest material is a compound primarily responsible for light emission in the light emitting layer.

When the total of the compounds forming the light emitting layer is assumed to be 100 percent by weight, the concentration of the guest material is 0.01 to less than 50 percent by weight and preferably 0.1 to 20 percent by weight. In order to suppress the concentration quenching, the concentration of the guest material is more preferably 10 percent by weight or less. In addition, the guest material may be uniformly contained in the whole layer formed of the host material, may be contained to have a concentration gradient, or may be contained partially in a specific region so as to form a region of the host material layer in which no guest material is contained.

This light emitting layer may be formed of either a single layer or a plurality of layers, and when light emitting materials having at least two types of light emission colors are contained, a mixed color may be emitted. In the case of using a plurality of layers, the light emitting layer may be laminated with a light emitting layer different therefrom. In this case, the light emission color of the organic light emitting element is from blue to green or red but is not particularly limited thereto.

In more particular, the light emission color may be either white or intermediate color. In the case of the white, by respective light emitting layers, red, blue, and green are emitted. In addition, the film formation may be performed by a deposition or a coating method.

In the organic light emitting element according to this embodiment, a light emitting portion may contain a plurality of types of light emitting materials. Any two out of the plurality of types of light emitting materials emit different types of light, and an element including those light emitting materials may be an element emitting white color.

In addition, the organic light emitting element according to this embodiment may be an organic light emitting element in which a plurality of light emitting layers is provided, at least one of the light emitting layers is a light emitting layer emitting light having a wavelength different from that of the rest of the light emitting layers, and those different types of light of the light emitting layer are mixed with each other to emit white light. In the case in which a plurality of light emitting layers is provided, the plurality of light emitting layers may be laminated to each other or arranged side by side. The "arranged side by side" indicates that the light emitting layers are each in contact with the hole transport layer, the electron transport layer, or the electrode adjacent thereto.

When the plurality of light emitting layers are laminated to each other, the light emitting layers may be in contact with each other, or another compound layer may be provided between the light emitting layers. The another compound layer may be a charge generation layer or the like.

Besides the organic compound according to this embodiment, if needed, for example, a low molecular weight-based or a high molecular weight-based light emitting material, a hole injection compound or a hole transport compound, a compound to be used as a host, a light emitting compound, and an electron injection compound or an electron transport compound, each of which has been known, may also be used together.

Hereinafter, examples of those compounds will be described.

As the hole injection/transport material, a material having a high hole mobility is preferable so that a hole from the anode can be easily injected and a hole thus injected is transported to the light emitting layer. In addition, in order to suppress the degradation in film quality, such as crystallization, in the organic light emitting element, a material having a high glass transition temperature is preferable. As a low molecular weight and a high molecular weight material having a hole injection/transport ability, for example, there may be mentioned a triarylamine derivative, an arylcarbazole derivative, a phenylenediamine derivative, a stilbene derivative, a phthalocyanine derivative, a porphyrin derivative, a polyvinylcarbazole, a polythiophene, and other electrically conductive polymers. Furthermore, the hole injection/transport material described above is also preferably used for the electron blocking layer.

Hereinafter, although concrete examples of the compounds to be used as the hole injection/transport material will be shown below, the compounds are not limited thereto.

HT1
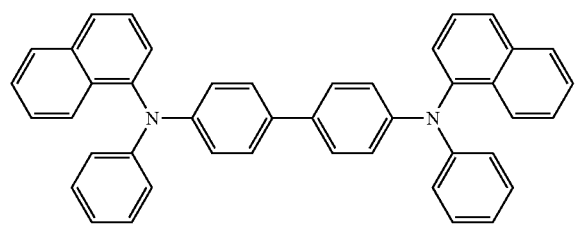
HT2
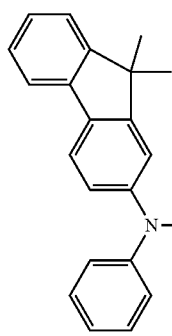
HT3
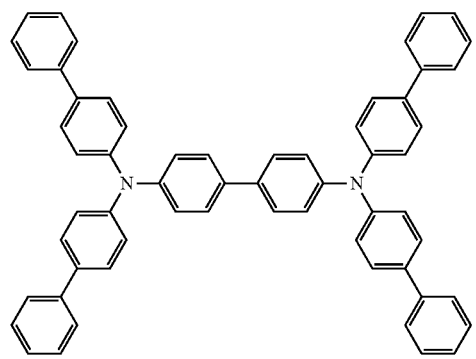
HT4
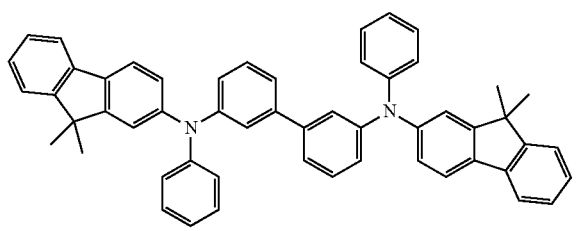
HT5
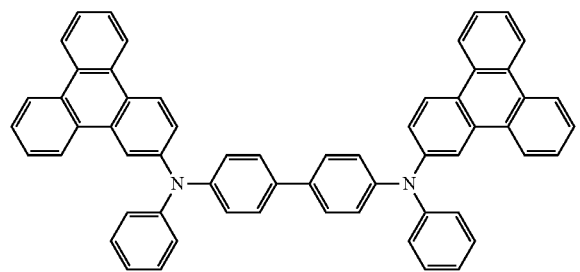
HT6
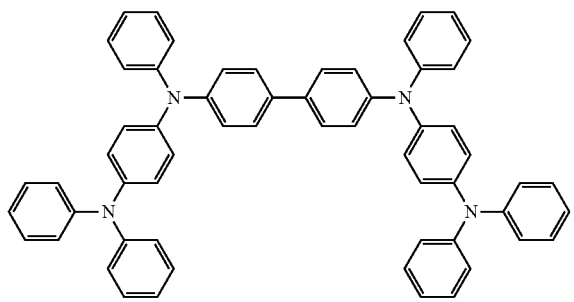
HT7
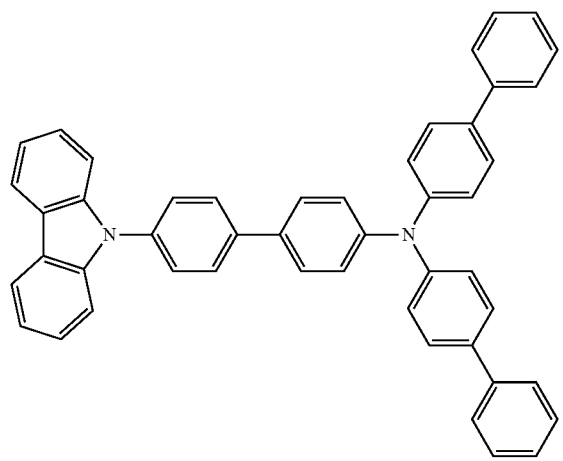
HT8
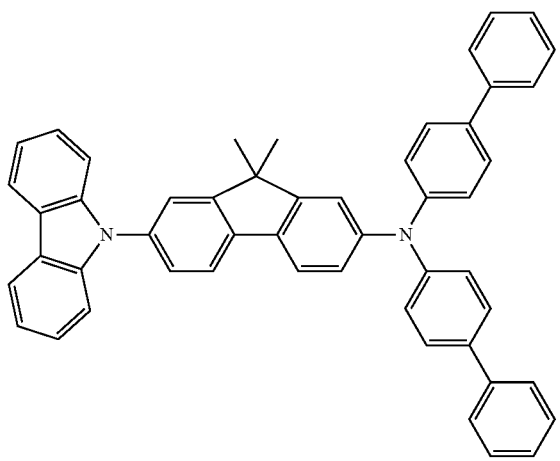

-continued
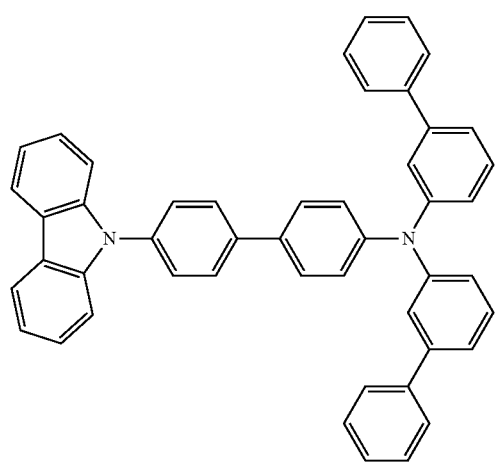
HT9
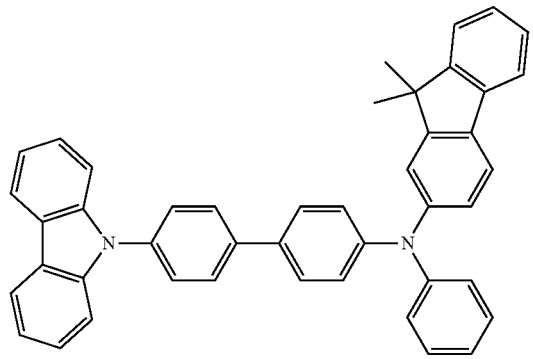
HT10
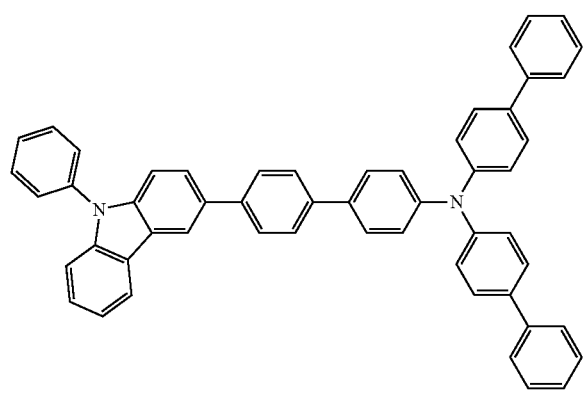
HT11
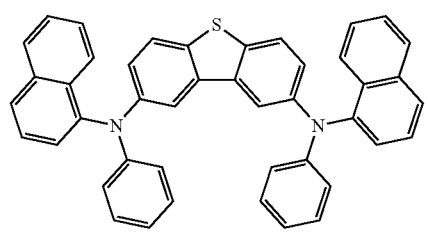
HT12
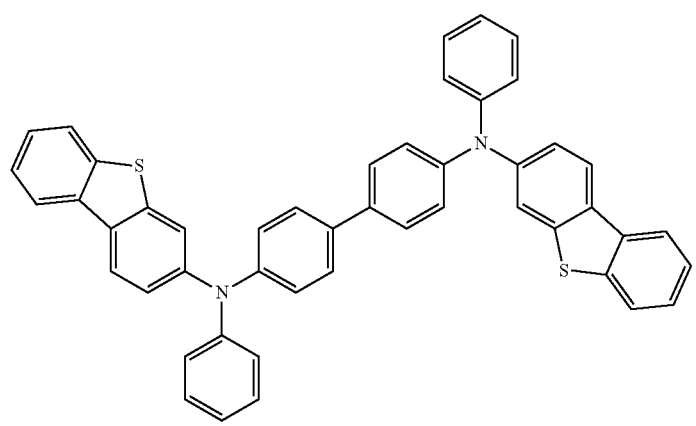
HT13

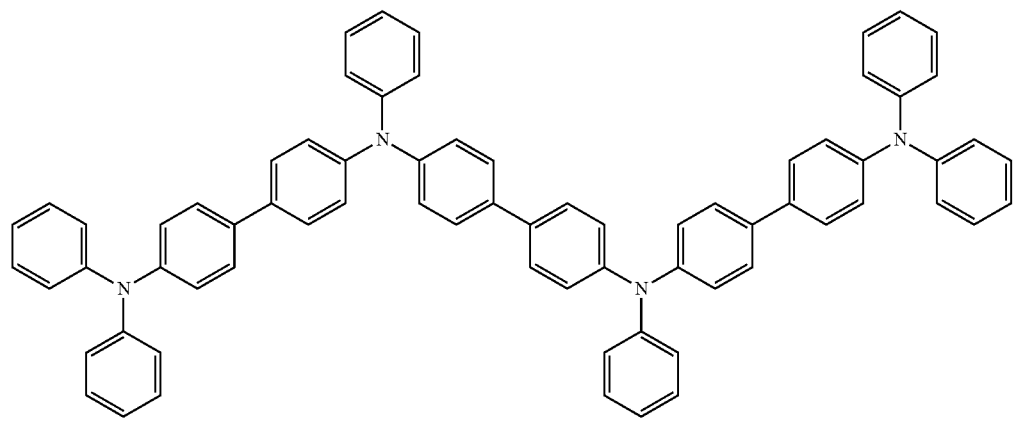

HT14

As a light emitting material primarily relating to the light emission function, for example, there may be mentioned a condensed ring compound (such as a fluorene derivative, a naphthalene derivative, a pyrene derivative, a perylene derivative, a tetracene derivative, an anthracene derivative, and a rubrene derivative), a quinacridone derivative, a cumarin derivative, a stilbene derivative; an organic aluminum complex, such as tris(8-quinolinolato) aluminum; an iridium complex, a platinum complex, a rhenium complex, a copper complex, an europium complex, a ruthenium complex, and a high molecular weight derivative, such as a poly(phenylene vinylene) derivative, a polyfluorene derivative, and a polyphenylene derivative.

Hereinafter, although concrete examples of the compounds to be used as the light emitting material will be shown below, the compounds are not limited thereto.

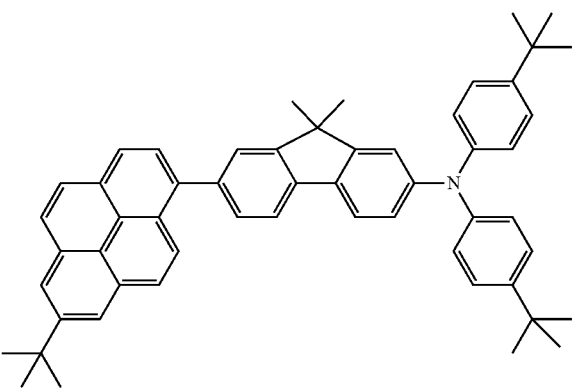

BD3

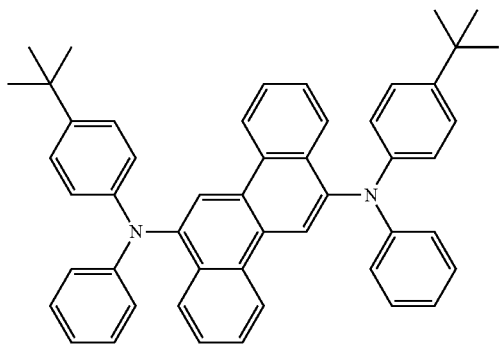

BD1

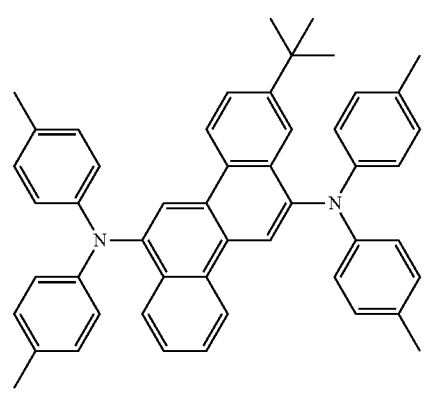

BD2

BD4

BD5

BD6 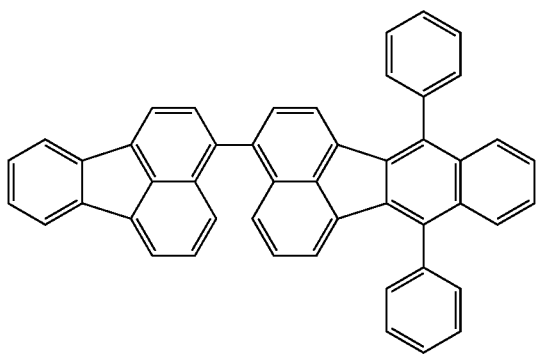
BD7 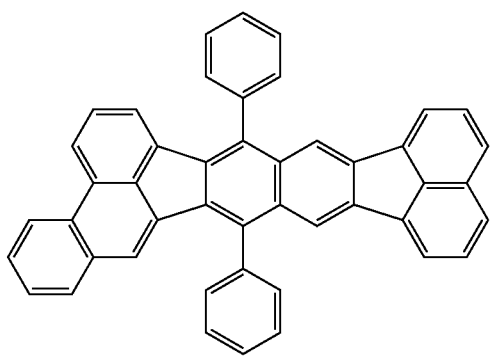
BD8 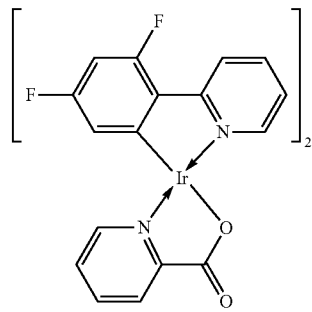
GD1 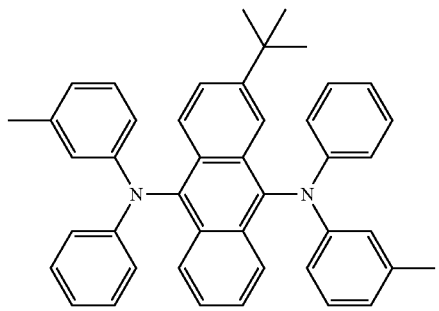
GD2 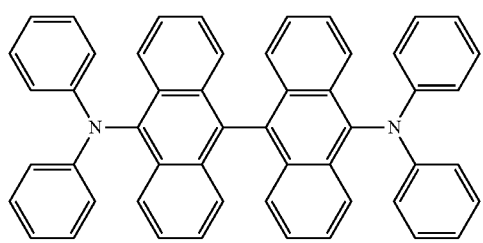
GD3 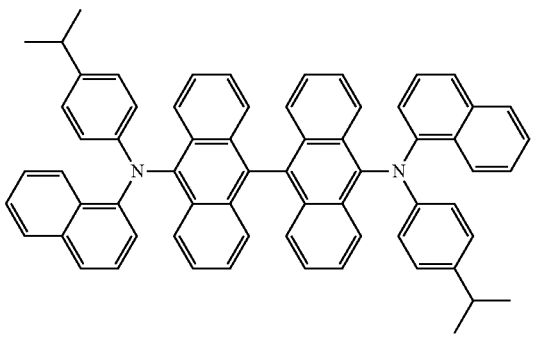
GD4 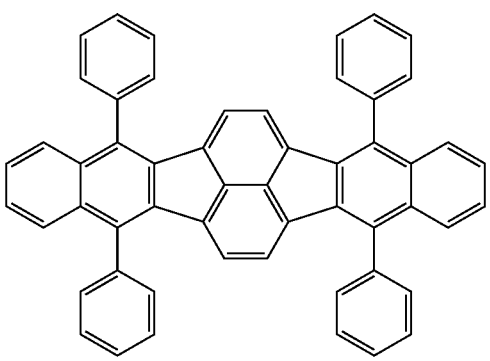
GD5 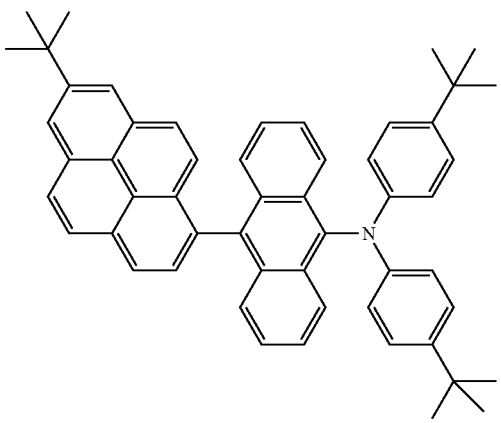
GD6 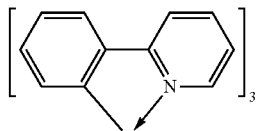
GD7 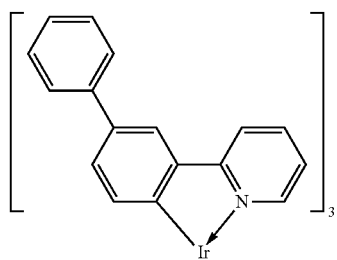

GD8
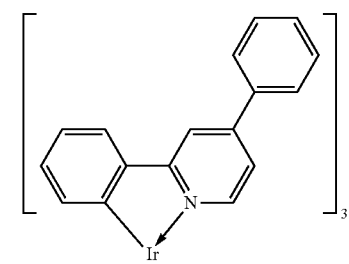

RD5
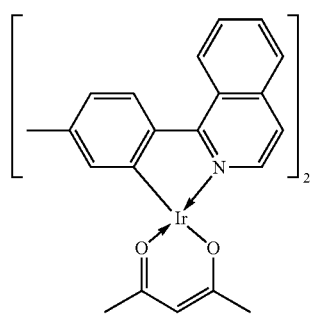

RD1
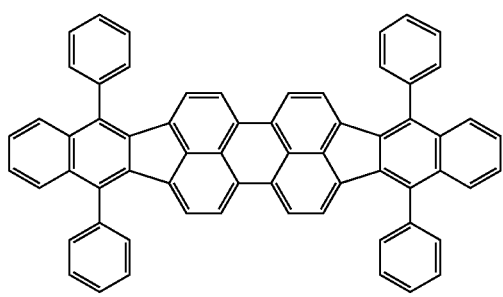

RD6
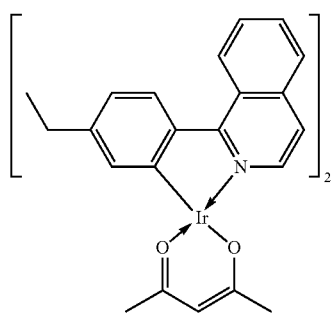

RD2
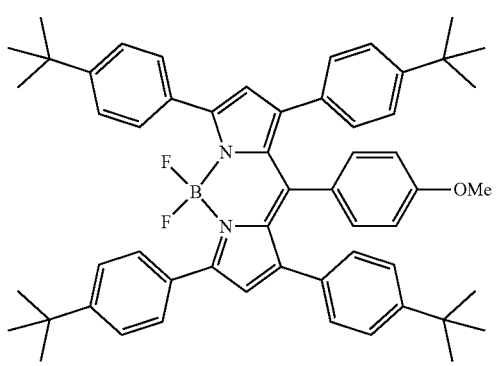

RD7
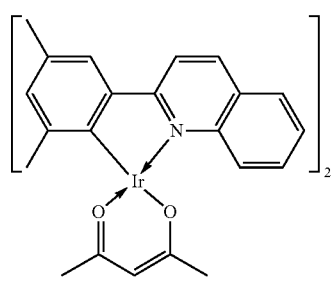

RD8
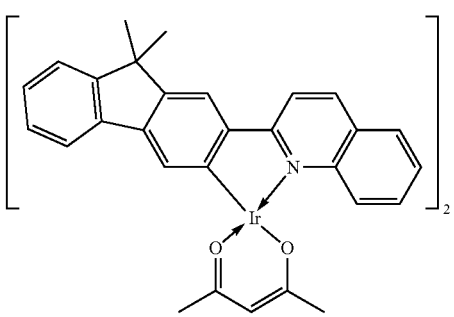

RD3
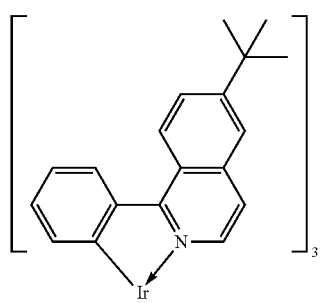

RD4

As a light emitting-layer host or a light emitting assist material contained in the light emitting layer, for example, besides an aromatic hydrocarbon compound and the derivatives thereof, a carbazole derivative, a dibenzofuran derivative, a dibenzothiophene derivative, an organic aluminum complex, such as tris(8-quinolinolato) aluminum, and an organic beryllium complex may be mentioned.

Hereinafter, although concrete examples of the compounds to be used as the light emitting-layer host or the light emitting assist material contained in the light emitting layer will be shown below, the compounds are not limited thereto.

EM1
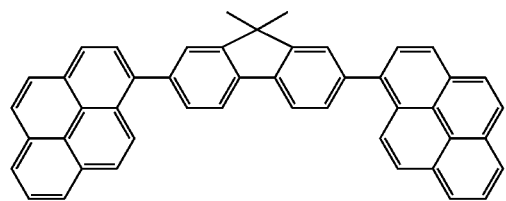
EM2
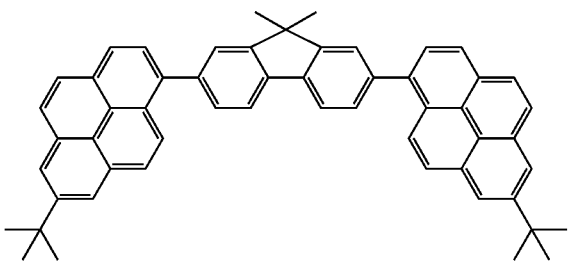
EM3
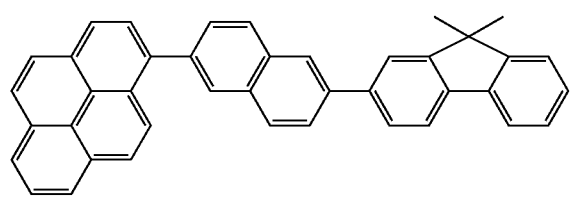
EM4
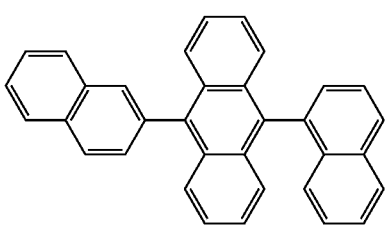
EM5
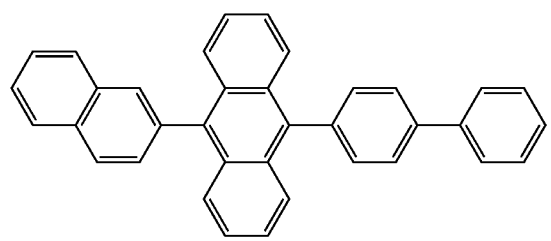
EM6
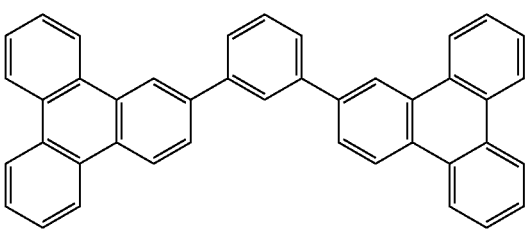
EM7
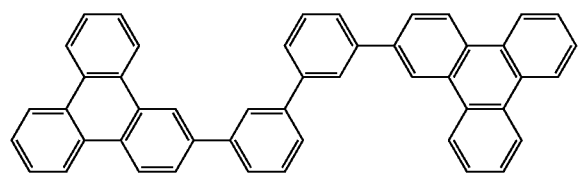
EM8
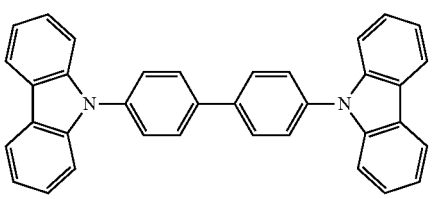
EM9
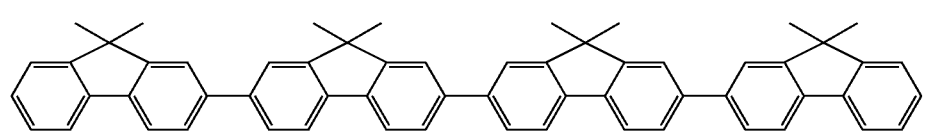
EM10
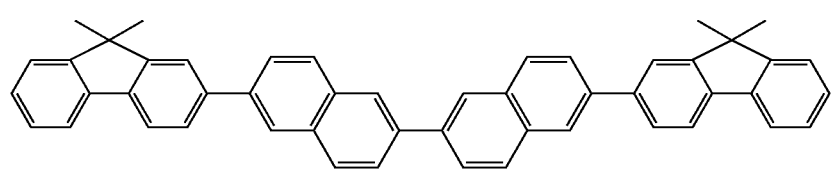

-continued

EM11

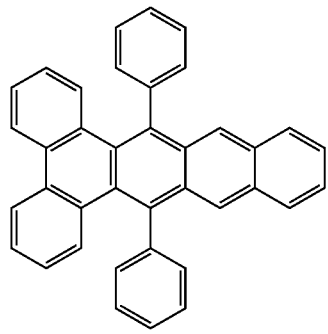

EM12

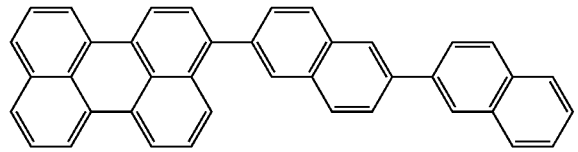

EM13

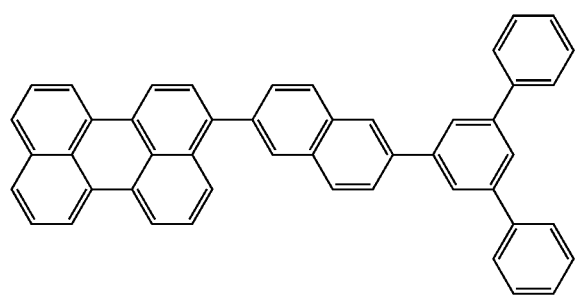

EM14

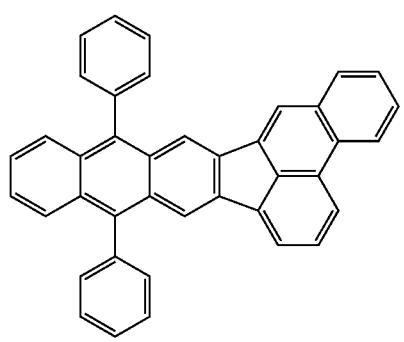

EM15

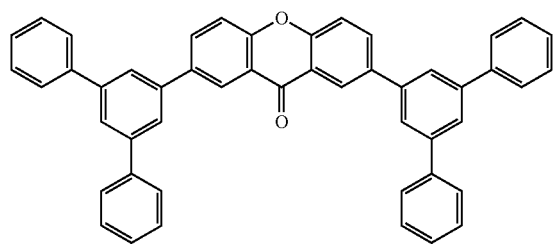

EM16

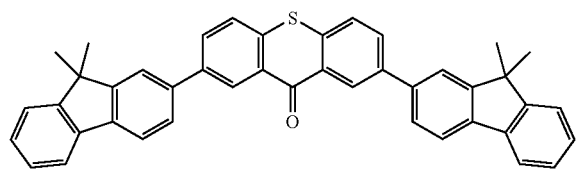

EM17

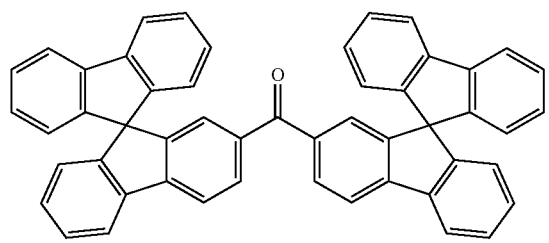

As the electron transport material, any material capable of transporting electrons injected from the cathode to the light emitting layer may be selected in consideration of, for example, the balance with the hole mobility of the hole transport material. As the material having an electron transport ability, for example, there may be mentioned an oxadiazole derivative, an oxazole derivative, a pyrazine derivative, a triazole derivative, a triazine derivative, a quinoline derivative, a quinoxaline derivative, a phenanthroline derivative, an organic aluminum complex, and a condensed ring compound (such as a fluorene derivative, a naphthalene derivative, a chrysene derivative, or an anthracene derivative). Furthermore, the above electron transport material is also preferably used for the hole blocking layer.

Hereinafter, concrete examples of the compounds to be used as the electron transport material will be shown below, but the compounds are not limited thereto.

ET1

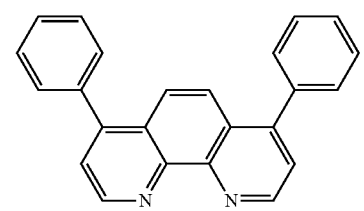

ET2
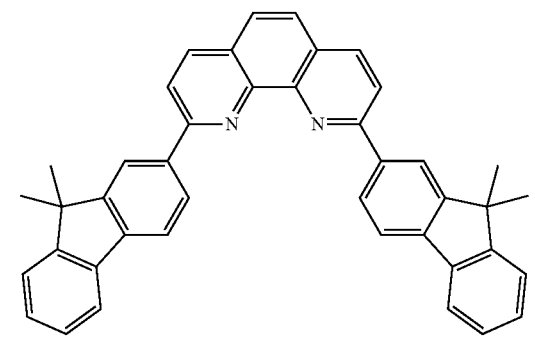
ET3
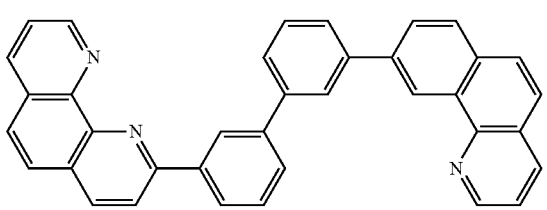
ET4
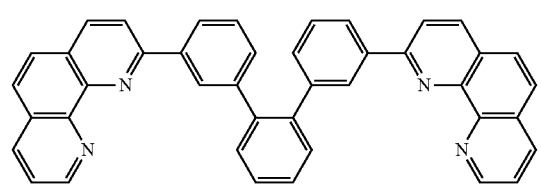
ET5
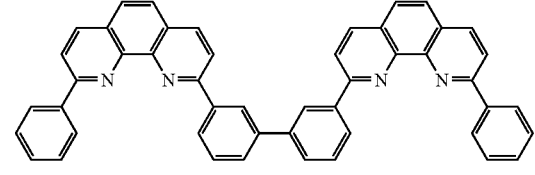
ET6
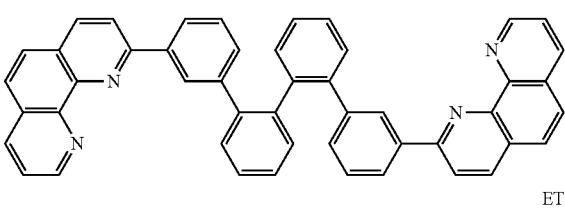
ET7
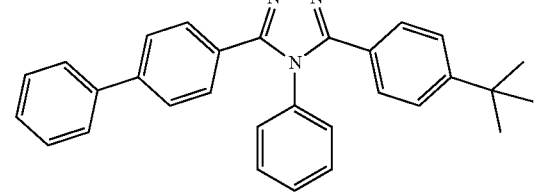
ET8
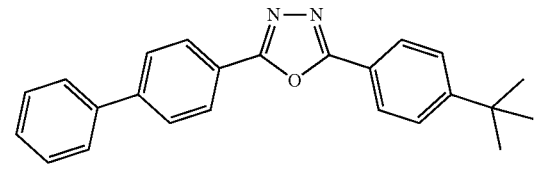
ET9
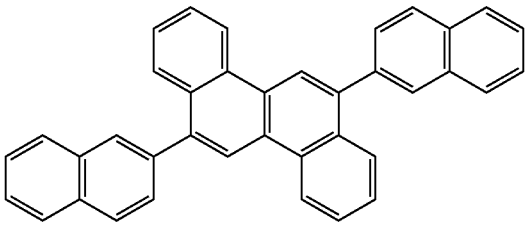
ET10
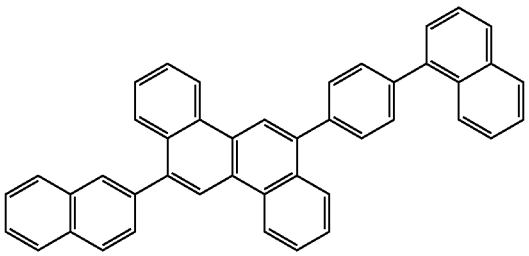
ET11
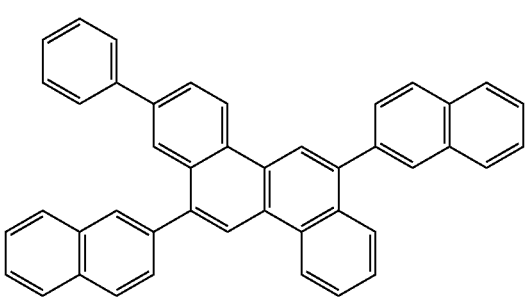
ET12
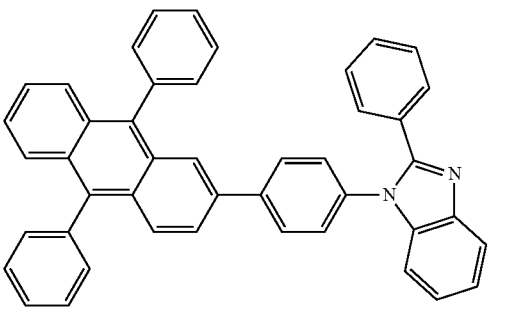
ET13
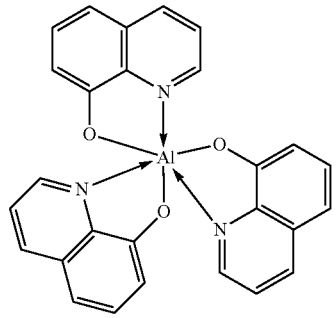

ET14

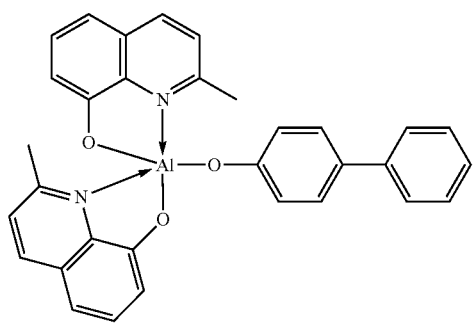

ET15

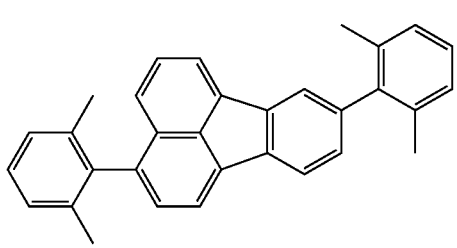

ET16

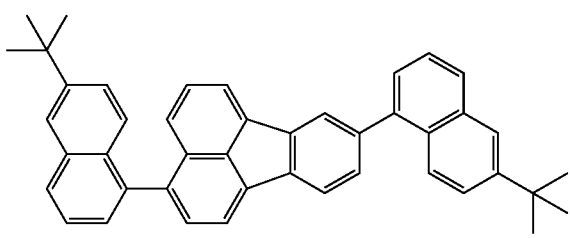

As the electron injection material, any material capable of easily performing electron injection from the cathode may be selected in consideration of, for example, the balance with the hole injection property. A bis(benzoimidazole-2-ilydene) compound having an alkyl cross-linking shown in this embodiment by way of example may also be used by mixing with the electron transport material. In addition, the compound described above may also be used by mixing with a material containing a cyano group, a fluorine atom, or a fluoranthene skeleton or a material containing a condensed ring structure. In this case, "material containing a fluoranthene skeleton" indicates a material having a fluoranthene structure in its chemical structure. Among the example compounds described in this embodiment, ET10, EI6, EI7, EI8, EI9, EI12, EI14, EI15, EI16, EI17, EI18, and EI19 may be mentioned.

EI1

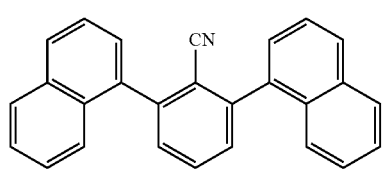

EI2

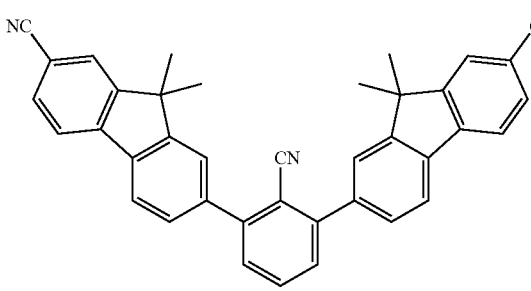

EI3

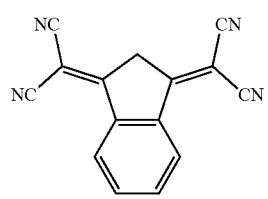

EI4

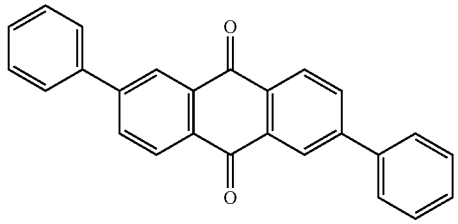

EI5

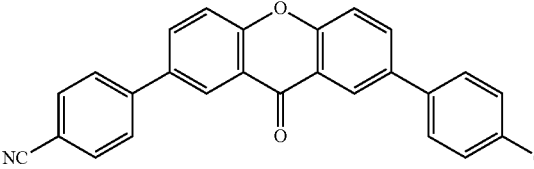

EI6

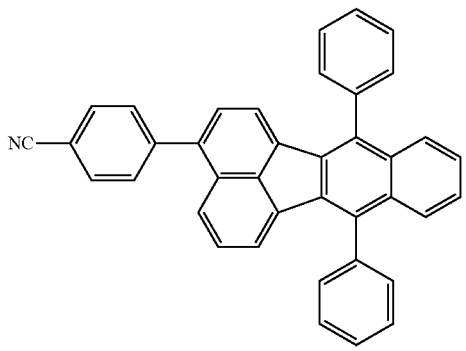

EI7

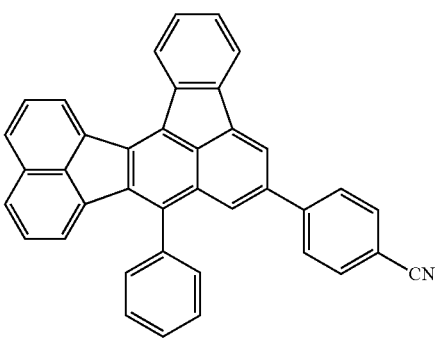

-continued
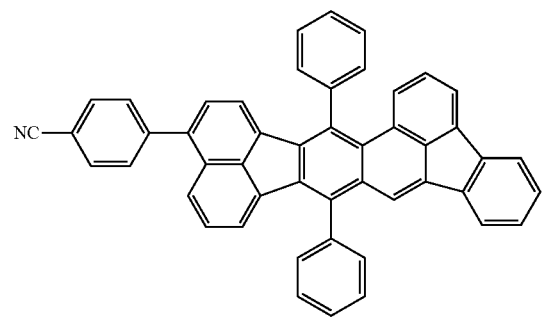
EI8
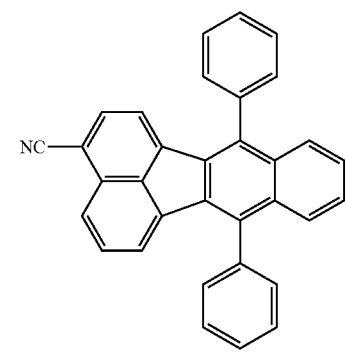
EI9
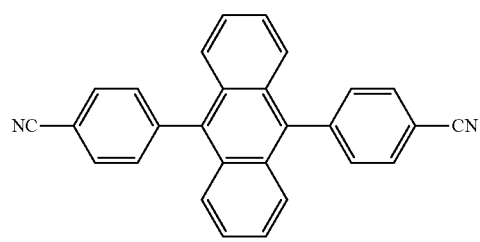
EI10
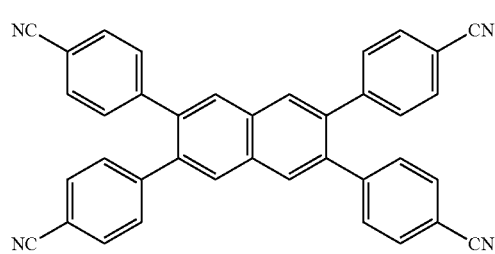
EI11
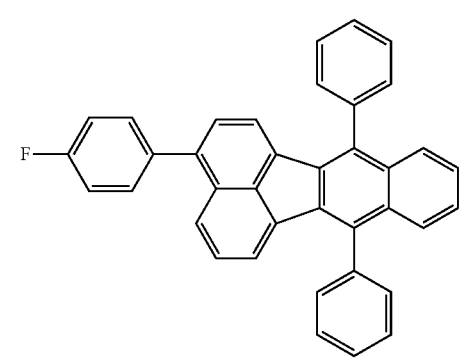
EI12
-continued
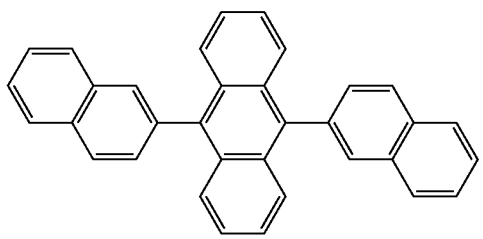
EI13
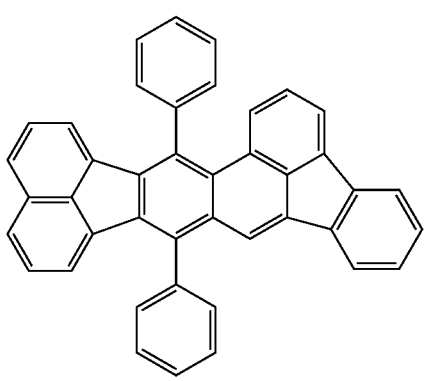
EI14
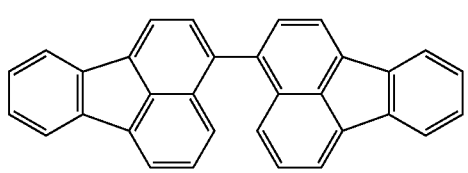
EI15
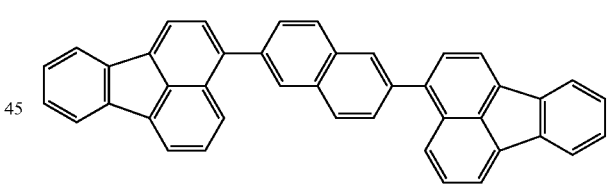
EI16
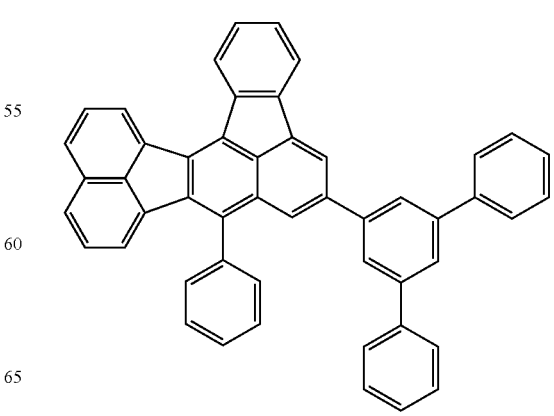
EI17

-continued

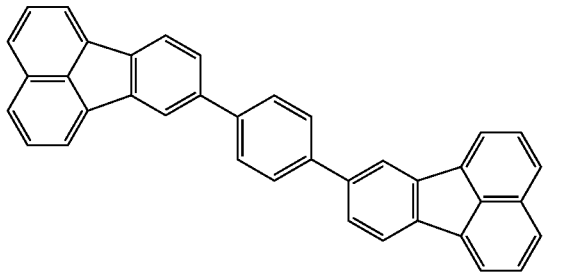

EI18

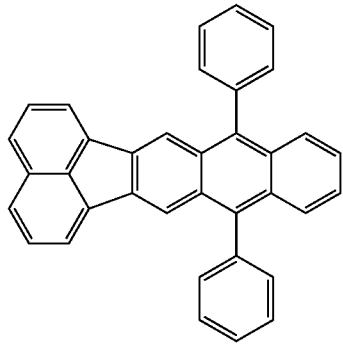

EI19

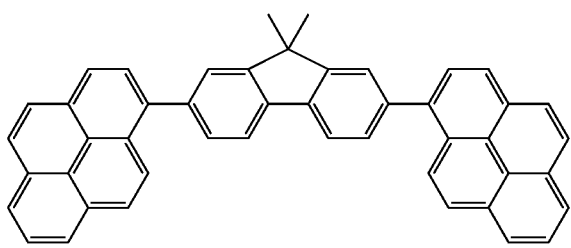

EI20

A material forming the anode preferably has a high work function as much as possible. For example, there may be used a metal element, such as gold, platinum, silver, copper, nickel, palladium, cobalt, selenium, vanadium, or tungsten; a mixture containing the metal mentioned above; an alloy formed from the metal mentioned above; or a metal oxide, such as tin oxide, zinc oxide, indium oxide, indium tin oxide (ITO), or indium zinc oxide. In addition, an electrically conductive polymer, such as a polyaniline, a polypyrrole, or a polythiophene, may also be used.

Those electrode materials may be used alone, or at least two types thereof may be used in combination. In addition, the anode may be formed of either a single layer or a plurality of layers.

On the other hand, as a material forming the cathode, a material having a low work function is preferable. For example, an alkali metal, such as lithium, an alkaline earth metal, such as calcium, a metal element, such as aluminum, titanium, manganese, silver, lead, or chromium, or a mixture containing the above metal may be mentioned. In addition, an alloy formed by combination of the metals mentioned above may also be used. For example, magnesium-silver, aluminum-lithium, aluminum-magnesium, silver-copper, or zinc-silver may be used. A metal oxide such as indium tin oxide (ITO) may also be used. Those electrode materials may be used alone, or at least two types thereof may be used in combination. In addition, the cathode may be formed of either a single layer or a plurality of layers.

The organic compound layers (such as the hole injection layer, the hole transport layer, the electron blocking layer, the light emitting layer, the hole blocking layer, the electron transport layer, and the electron injection layer) forming the organic light emitting element according to this embodiment are formed by the methods shown below.

The organic compound layers forming the organic light emitting element according to this embodiment may be formed by using a dry process, such as a vacuum deposition method, an ionization deposition method, sputtering, or plasma CVD. In addition, instead of using a dry process, a wet process may also be used which forms a layer by a known coating method (such as spin coating, dipping, a casting method, an LB method, or an inkjet method) using a solution containing an appropriate solvent and an organic compound.

In this case, when the layer is formed by a vacuum deposition method, a solution coating method, or the like, for example, crystallization is not likely to occur, and hence the aging stability is excellent. In addition, when the film is formed by a coating method, the film may be formed in combination with an appropriate binder resin.

As the binder resin mentioned above, although a polyvinyl carbazole) resin, a polycarbonate resin, a polyester resin, an ABS resin, an acrylic resin, a polyimide resin, a phenol resin, an epoxy resin, a silicone resin, or a urea resin may be mentioned, the binder resin is not limited thereto.

In addition, as the binder resin, homopolymers or copolymers may be used alone, or at least two types thereof may be used in combination. Furthermore, if needed, additives, such as a known plasticizer, antioxidant, and UV absorber, may also be used together therewith.

Application of Organic Light Emitting Element According to Embodiment

The organic light emitting element according to this embodiment may be used as a constituent member of a display device or a lighting device. Furthermore, the organic light emitting element described above may also be applied to, for example, an exposure light source of an electrophotographic image forming device, a backlight of a liquid crystal device, or a light emitting device having a color filter provided for a white light source. As the color filter, for example, a filter which allows one of three colors, red, green, and blue, to pass therethrough may be mentioned.

The display device according to this embodiment has a plurality of pixels, and at least one of those pixels has the organic light emitting element according to this embodiment. In addition, this pixel has the organic light emitting element according to this embodiment and an active element. As the active element, a switching element or an amplifier element may be mentioned, and in particular, a transistor may be mentioned. The anode or the cathode of this organic light emitting element is electrically connected to a drain electrode or a source electrode of the transistor. The transistor may have an oxide semiconductor in its active region. The oxide semiconductor may be either amorphous or crystalline or may be a mixture thereof. The crystal may be any one of a single crystal, a fine crystal, and a crystal in which a specific axis, such as the C axis, is oriented, or may be a mixture containing at least two crystals mentioned above.

The organic light emitting device having the switching element as described above may also be used as an image display device in which the organic light emitting elements are each provided as the pixel or may also be used as a lighting device. In addition, the organic light emitting device described above may also be used as an exposure light source exposing a photoreceptor of an electrophotographic type image forming device, such as a laser printer or a copying machine.

In this case, the display device may be used as an image display device of a personal computer (PC) or the like. As the transistor described above, for example, a thin film transistor (TFT) element may be mentioned, and this TFT element is provided, for example, on an insulating surface of a substrate.

The display device may be an image information processing device which has an image input portion inputting image information from an area charge coupled device (CCD), a linear CCD, a memory card, or the like, an information processing portion processing input information, and a display portion displaying an input image.

In addition, the display portion of an image taking device or an inkjet printer may have a touch panel function. A drive method of this touch panel function may be any one of an infrared method, an electrostatic capacitance method, a resistive membrane method, and an electromagnetic induction method but is not particularly limited.

In addition, the display device may be used for a display portion of a multifunctional printer.

The lighting device is a device lighting the inside of a room. The lighting device may be a device emitting any one of white color (color temperature: 4,200K), neutral white color (color temperature: 5,000K), and other colors from blue to red. Among organic light emitting elements of the lighting device, any one of the organic light emitting elements may be the organic light emitting element of the present disclosure.

The lighting device according to this embodiment has the organic light emitting element according to this embodiment and an AC/DC converter connected thereto. The AC/DC converter is a circuit converting an alternating current voltage to a direct current voltage. This converter is a circuit to supply a drive voltage to the organic light emitting element. In addition, this lighting device may further have a color filter.

In addition, the lighting device according to this embodiment may have a heat dissipation portion. The heat dissipation portion functions to dissipate heat in the device to the outside thereof and may be formed of a metal having a high specific heat, liquid silicon, or the like.

The image forming device according to this embodiment is an image forming device having a photoreceptor, an exposure portion exposing this photoreceptor, a charging portion charging this photoreceptor, and a developing portion imparting a developer to the photoreceptor. In this case, the exposure portion of the image forming device has a plurality of the organic light emitting elements of the present disclosure. As the developer, toner, ink, or the like may be mentioned. The toner may be either a dry toner or a liquid toner.

In addition, the organic light emitting element according to this embodiment may be used as a constituent member of an exposure device exposing a photoreceptor. An exposure device having the organic light emitting element according to this embodiment has a plurality of light emitting points, and at least any one of the light emitting points described above has the organic light emitting element according to this embodiment. Those light emitting points are aligned along a long axis direction of the photoreceptor.

Figure 3:
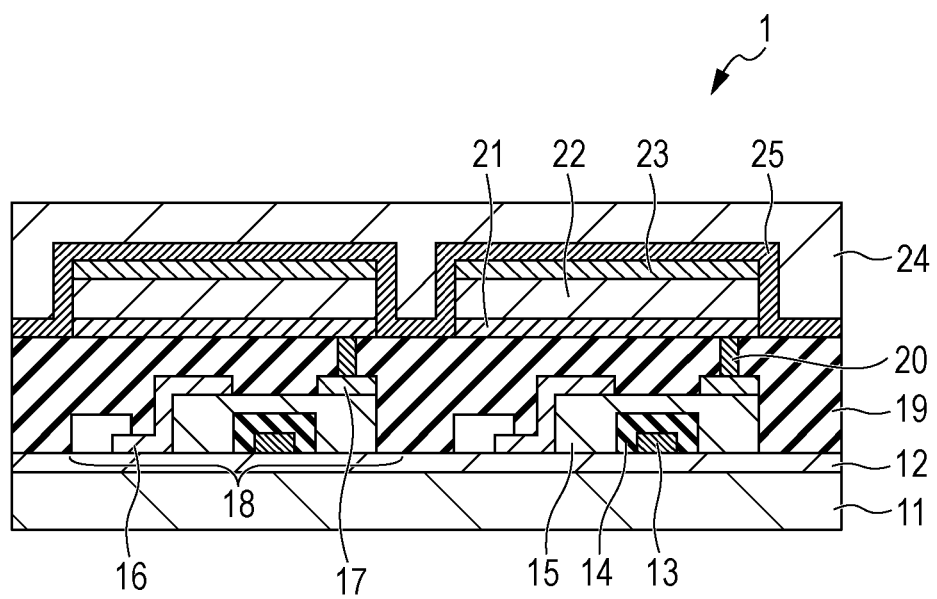
FIG. 3 is a schematic cross-sectional view showing an organic light emitting element according to the present disclosure and a switching element connected thereto.

Next, with reference to the drawings, the display device according to this embodiment will be described. FIG. 3 is a schematic cross-sectional view showing one example of a display device having an organic light emitting element and a TFT element connected thereto. The TFT element is one example of the active element.

A display device 1 shown in FIG. 3 includes a substrate 11 formed of glass or the like and a moistureproof film 12 provided thereon to protect the TFT element or the organic compound layer. In addition, reference numeral 13 indicates a gate electrode formed of a metal. Reference numeral 14 indicates a gate insulating film, and reference numeral 15 indicates a semiconductor layer.

A TFT element 18 has the semiconductor layer 15, a drain electrode 16, and a source electrode 17. On the TFT element 18, an insulating film 19 is provided. Through a contact hole 20, an anode 21 forming the organic light emitting element and the source electrode 17 are connected to each other.

In addition, the method for electrical connection between the electrodes (the anode and the cathode) of the organic light emitting element and the electrodes (the source electrode and the drain electrode) of the TFT is not limited to the mode shown in FIG. 3. That is, any one of the anode and the cathode and any one of the source electrode and the drain electrode of the TFT element may be electrically connected to each other.

In the display device 1 shown in FIG. 3, although the organic compound layer is shown as if formed of one layer, an organic compound layer 22 may be formed of a plurality of layers. On a cathode 23, a first protective layer 24 and a second protective layer 25, each of which suppresses the degradation of the organic light emitting element, are provided.

In the display device 1 shown in FIG. 3, although the transistor is used as a switching element, instead of using the transistor, a metal-insulator-metal (MIM element) may also be used as a switching element.

In addition, the transistor used in the display device 1 shown in FIG. 3 is not limited to a transistor using a single crystal silicon wafer but may be a thin film transistor having an active layer on an insulating surface of a substrate. As the active layer, for example, single crystal silicon, non-single crystal silicon, such as amorphous silicon or fine crystal silicon, or a non-single crystal oxide semiconductor, such as indium zinc oxide or indium gallium zinc oxide, may be mentioned. In addition, the thin film transistor is also called a TFT element.

The transistor included in the display device 1 shown in FIG. 3 may be formed in the substrate, such as a Si substrate. In this case, "being formed in the substrate" indicates the case in which the transistor is formed by machining the substrate itself, such as a Si substrate. That is, the transistor provided in the substrate may also be considered that the substrate and the transistor are integrally formed.

Whether the transistor is provided in the substrate or not may be selected in consideration of the definition. For example, the case in which the definition per inch is approximately equal to that of QVGA, the transistor is preferably provided in a Si substrate.

Figure 4:
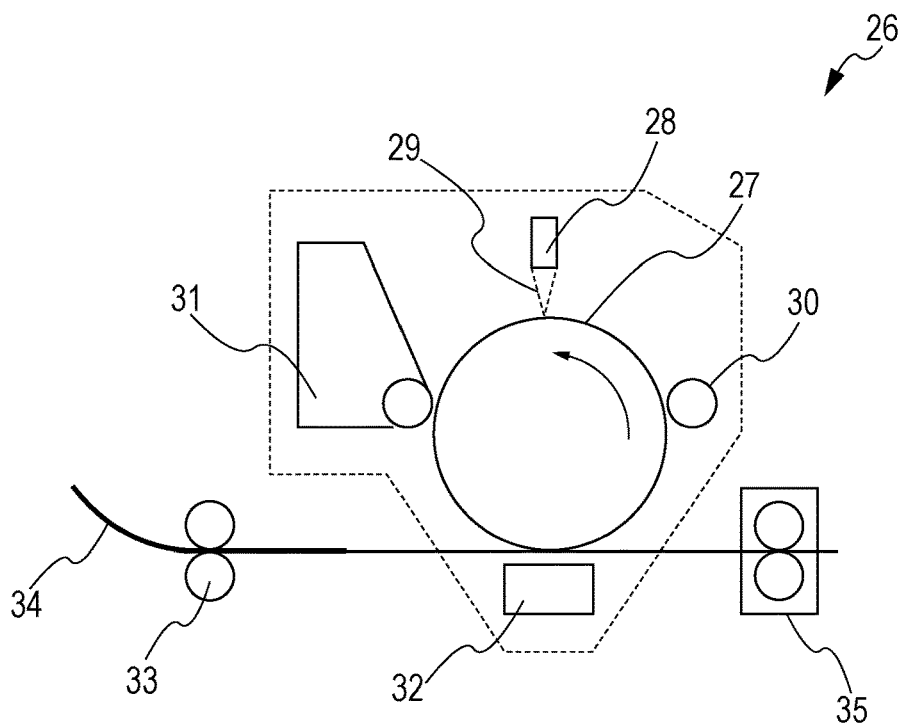
FIG. 4 is a schematic view showing one example of an image forming device according to the present disclosure.

FIG. 4 is a schematic view of an image forming device 26 according to the present disclosure. The image forming device has a photoreceptor, an exposure light source, a developing portion, a charging portion, a transfer unit, a transport roller, and a fixing unit.

Light 29 is emitted from an exposure light source 28, and an electrostatic latent image is formed on the surface of a photoreceptor 27. This exposure light source 28 has the organic light emitting element according to the present disclosure. A developing portion 30 has toner or the like. A charging portion 31 charges the photoreceptor 27. A transfer unit 32 transfers a developed image onto a recording medium 34. A transport roller 33 transports the recording medium 34. The recording medium 34 is for example, paper. A fixing unit 35 fixes an image formed on the recording medium 34.

Figure 5:
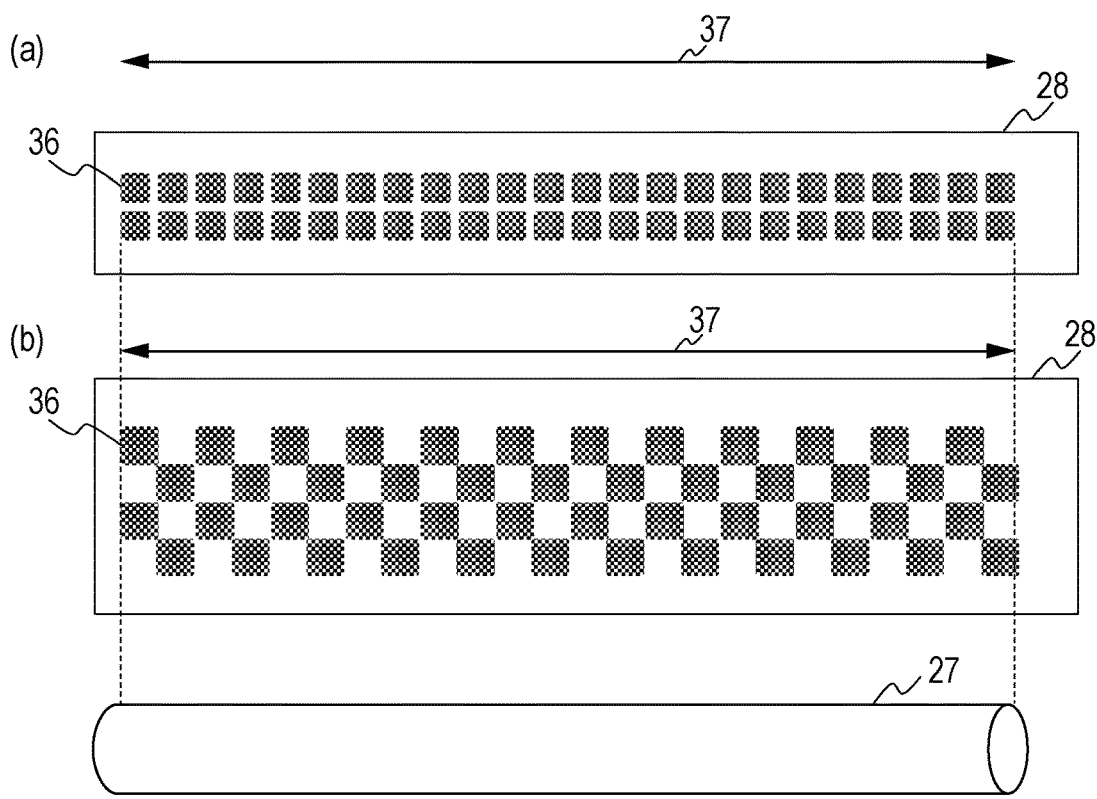
FIG. 5 is a schematic view showing one example of an exposure device according to the present disclosure.

FIG. 5 is a schematic view showing the exposure light source 28 in which a plurality of light emitting portions 36 is disposed on a long substrate. An arrow 37 indicates a column direction along which the organic light emitting elements are arranged. This column direction is the same direction as that of the axis around which the photoreceptor 27 is rotated. This direction may also be called the long axis direction of the photoreceptor.

A part (a) of FIG. 5 shows the state in which the light emitting portions are arranged along the long axis direction of the photoreceptor. A part (b) of FIG. 5 shows the state different from that of the part (a) and the state in which the light emitting portions of a first column and the light emitting portions of a second column are arranged intermittently along the column direction. The first column is arranged at a position different from that of the second column in the row direction.

In the first column, the light emitting portions are arranged with spaces provided therebetween. In the second column, the light emitting portions are arranged at positions corresponding to the spaces of the light emitting portions of the first column. That is, in the row direction, the light emitting portions are also arranged with spaces therebetween.

The arrangement of the part (b) of FIG. 5 may also be called a lattice arrangement, a stagger arrangement, or a checkered pattern arrangement.

Figure 6:
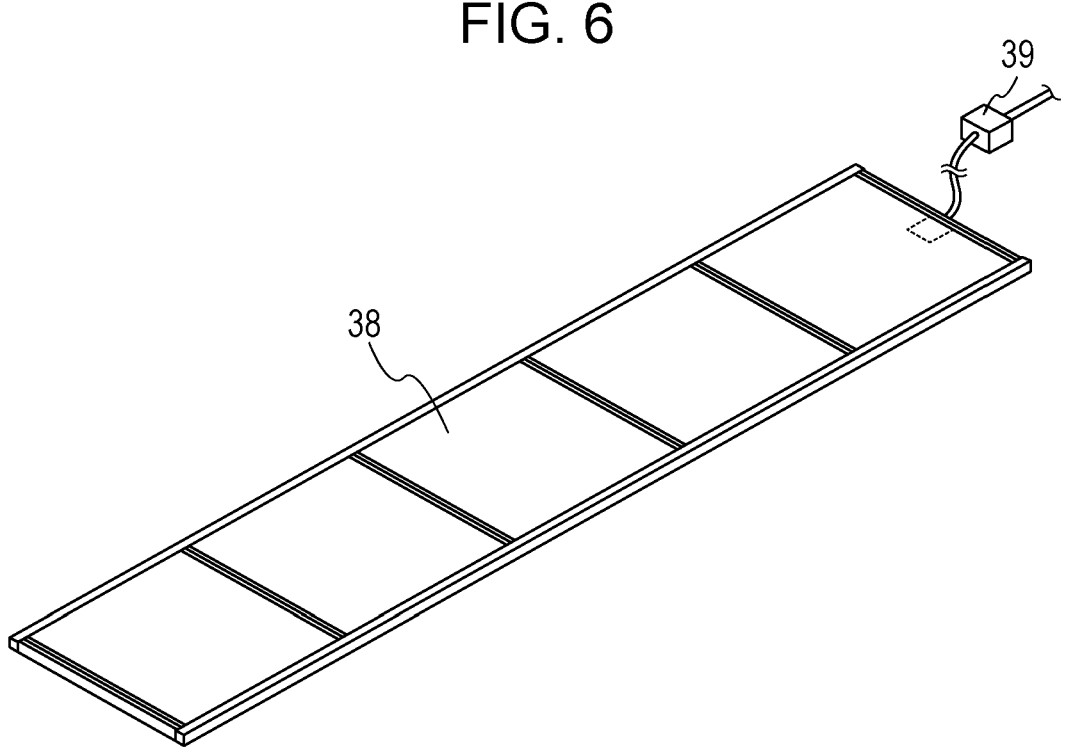
FIG. 6 is a schematic view showing one example of a lighting device according to the present disclosure.

FIG. 6 is a schematic view of the lighting device according to the present disclosure. The lighting device has a substrate, an organic light emitting element 38, and an AC/DC converter 39. The lighting device may also have a switching element connected to the organic light emitting element. In addition, a heat dissipation portion not shown in the drawing may also be provided, for example, at a rear surface side opposite to the substrate surface on which the organic light emitting element is provided.

As described above, when the display device, the lighting device, and the image forming device, each of which uses the organic light emitting element of the present disclosure, is driven, an excellent image quality can be obtained, and a long and stable operation can be performed.

Figure 7:
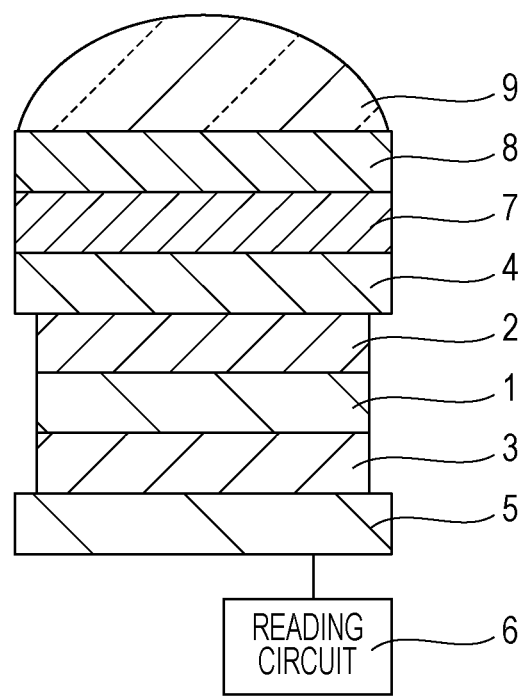
FIG. 7 is a schematic view showing one example of an organic photoelectric conversion element according to the present disclosure.

FIG. 7 is a schematic view showing one example of an organic photoelectric conversion element according to this embodiment.

The organic photoelectric conversion element according to this embodiment has an anode 44, a cathode 43, and an organic photoelectric conversion layer 40 provided therebetween. A second organic compound layer 41 may be provided between the cathode 43 and the organic photoelectric conversion layer 40, and the second organic compound layer may contain the organic compound according to the present disclosure. A third organic compound layer 42 may be provided between the anode 44 and the organic photoelectric conversion layer 40. The third organic compound layer may contain the organic compound according to the present disclosure. The anode 44 or the cathode 43 is connected to a reading circuit 45. The reading circuit 45 reads information based on the charge generated in the organic photoelectric conversion layer 40 and, for example, transmits the information to a signal processing circuit (not shown) provided at a latter stage. The reading circuit 45 includes, for example, a transistor which outputs a signal based on the charge generated in the organic photoelectric conversion layer.

An inorganic protective layer 46 is disposed on the cathode 43. The inorganic protective layer 46 may be formed by a sputtering method, a vacuum deposition method, an aluminum layer deposition (ALD) method, or the like using aluminum oxide, silicon oxide, silicon nitride, or the like.

On the inorganic protective layer 46, a color filter 47 is disposed. The color filter may form a Bayer arrangement in combination with color filters of adjacent organic photoelectric conversion elements.

On the color filter 47, a microlens 48 is disposed. The microlens condenses incident light on the organic photoelectric conversion layer.

The organic photoelectric conversion element according to this embodiment may be used for an image taking element. The image taking element has a plurality of pixels and a signal processing portion connected thereto.

In a pixel including the organic photoelectric conversion element, a different type of organic photoelectric conversion element performing photoelectric conversion of different color light may be further provided. The different type of organic photoelectric conversion element is laminated on the organic photoelectric conversion element. The different type of organic photoelectric conversion element is an element performing photoelectric conversion of light in a different wavelength region, and when those elements are used in combination, an image taking element may be formed without providing the color filter.

The organic photoelectric conversion element according to this embodiment may be used for an image taking element. The image taking element includes a plurality of pixels and a signal processing portion. At least one pixel includes the organic photoelectric conversion element according to this embodiment and a reading circuit connected thereto. The plurality of pixels are arranged in a matrix containing a plurality of rows and a plurality of columns. In the structure as described above, a signal is output from each pixel as one pixel signal, so that an image signal can be obtained.

The pixel may also have a color filter at a light incident side. As the color filter, a color filter which transmits specific light, such as red light, may be mentioned. One pixel may be provided for one color filter.

The pixel may have a microlens at a light incident side. The microlens is a lens condensing light on the photoelectric conversion layer.

When the organic photoelectric conversion element according to this embodiment is used for an image taking element, an optical filter may be provided at a light incident side of the image taking element. As the optical filter, for example, a low-pass filter, a UV-cut filter cutting light having a wavelength of UV rays or less, an IR-cut filter cutting infrared rays may be mentioned. By the use of those optical filters, noises are reduced, and hence an image having a high image quality can be obtained.

The organic photoelectric conversion element according to this embodiment may be used for an image taking device. The image taking device has an image taking optical system and an image taking element receiving light passing through the image taking optical system.

The image taking device may further have a receiving portion receiving a signal from the outside or a transmitting portion transmitting an obtained image to the outside. The signal received by the receiving portion may be a signal controlling at least one of an image taking range of the image taking device, the start of image taking, and the stop of image taking.

A method in which the image taking device communicates with the outside may be either a wired method or a wireless method.

As has thus been described, the organic compound according to the present disclosure may be used for the organic photoelectric conversion element. The organic photoelectric conversion element according to this embodiment is an organic photoelectric conversion element in which a dark current is suppressed, and when this element is used for an image taking element, an image taking element having a high resolution can be provided.

EXAMPLES

[Example 1] Synthesis of Example Compound A1

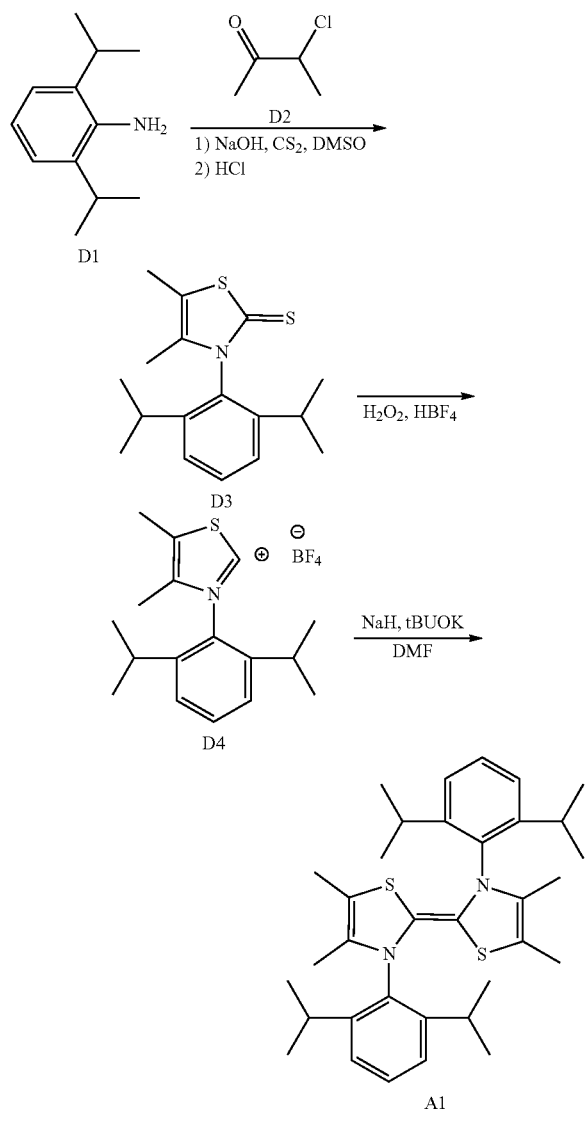

(1) Synthesis of Compound D3

The following reagent and solvents were charged into a 50-ml eggplant flask.
D1: 3.00 g (16.9 mmol)
DMSO: 10 ml
20 N NaOH aqueous solution: 0.8 ml Next, the reaction solution was cooled to 0° C. while being stirred in a nitrogen atmosphere. Subsequently, 1.0 ml (16.9 mmol) of carbon disulfide was slowly dripped and was then stirred at 0° C. for 30 minutes. Next, stirring was performed at room temperature for 1 hour. The solution was again cooled to 0° C., and 1.7 ml (16.9 mmol) of D2 was slowly dripped and was then stirred at 0° C. for 30 minutes. Subsequently, stirring was performed at room temperature for 1 hour. After the reaction was completed, water was added to the reaction solution and then stirred, and filtration thereof was performed using a membrane filter, so that a residue was obtained. After the residue thus obtained was dissolved in 20 ml of ethanol, 0.85 ml of a conc. hydrochloric acid was added, and heat reflux was performed for 1 hour while stirring was performed in a nitrogen atmosphere. After the reaction was completed, the reaction solution was cooled to room temperature, and a precipitated white solid was filtrated. A residue was re-crystallized using ethanol, so that 3.81 g (yield: 74%) of D3 was obtained.

(2) Synthesis of Compound D4

The following reagents and solvent were charged into a 50-ml eggplant flask.
D3: 1.00 g (3.27 mmol)
Acetic acid: 10 ml
Hydrogen peroxide solution: 1 ml Next, the reaction solution was stirred at room temperature in a nitrogen atmosphere for 2 hours. After the reaction was completed, the reaction solution was concentrated under a reduced-pressure condition, so that a residue was obtained. To this residue, 20 ml of water and 0.7 ml of $HBF_4$ were added, and stirring was performed at room temperature for 1 hour. A precipitated pale yellow solid was filtrated, so that a crude product was obtained. Next, this crude product was purified using a silica gel column chromatography (eluent: chloroform/ethanol=200/1 to 50/1) and was then processed by dispersion washing using a diethyl ether solvent, so that 0.90 g (yield: 76%) of D4 in the form of white solid was obtained.

(3) Synthesis of Example Compound A1

The following reagent and solvent were charged into a 50-ml eggplant flask in a nitrogen flow atmosphere.
D4: 470 mg (1.30 mmol)
Dehydrated DMF: 10 ml After this solution was deaerated using nitrogen, 187 mg (3.90 mmol) of sodium hydride (oil dispersion at 50% to 60%) was charged thereto, and stirring was then performed for 2 minutes. Subsequently, 145 mg (1.30 mmol) of potassium tert-butoxide was added, and stirring was performed at room temperature for 6 hours. After the reaction was completed, while stirring was performed, 30 ml of water which was deaerated using nitrogen was slowly added to precipitate a target product, and the solvent was then removed using a syringe. Next, after the operation of adding 20 ml of water deaerated using nitrogen and removing the solvent using a syringe was again performed twice, 10 ml of hexane deaerated using nitrogen was added, and dispersion washing was performed by an ultrasonic washing machine. Subsequently, after filtration was performed using a membrane filter, and a residue was washed with hexane deaerated using nitrogen, drying was performed at 50° C. under a reduced-pressure condition, so that 181 mg (yield: 51%) of the example compound A1 in the form of red powder was obtained.

The example compound A1 thus obtained was identified by the following method.
[Matrix Assisted Laser Desorption/Ionization-Time of Flight-Mass Spectroscopy (MALDI-TOF-MS) (Autoflex LRF Manufactured by Bruker)]
Measured value: m/z=546.50, calculated value: $C_{34}H_{46}N_2S_2$=546.87

By CV measurement under the following conditions, the first oxidation potential was −1.05 V.

The CV measurement was performed in an N,N-dimethylformamide solution of 0.1 M tetrabutylammonium perchlorate. The measurement was performed under the conditions in which Ag/Ag$^+$, Pt, and glassy carbon were used for the reference electrode, the counter electrode, and the working electrode, respectively, the oxidation reduction potential Fc/Fc$^+$ of ferrocene was used as the reference potential, and the sweeping rate of the voltage was set to 0.5 V/s. The measurement was performed using electrochemical analyzer Model1660C manufactured by ALS as the measurement device.

[Example 2] Synthesis of Example Compound A5

In Example 1(1), except that the compound D5 shown below was used instead of the compound D1, the example compound A5 was obtained by a method similar to that of Example 1.

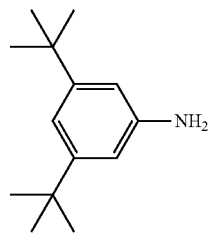

D5

The identification result of the compound thus obtained is shown below.
[MALDI-TOF-MS]
Measured value: m/z=602.88, calculated value: $C_{38}H_{54}N_2S_2$=602.98 [CV measurement]
First Oxidation Potential: −1.05 V

[Example 3] Synthesis of Example Compound A6

In Example 1(1), except that the compound D6 shown below was used instead of the compound D1, the example compound A6 was obtained by a method similar to that of Example 1.

D6

The identification result of the compound thus obtained is shown below.
[MALDI-TOF-MS]
Measured value: m/z=450.58, calculated value: $C_{22}H_{18}F_4N_4S_2$=450.52 [CV measurement]
First Oxidation Potential: −0.95 V

[Example 4] Synthesis of Example Compound A15

In Example 1(1), except that the compound D7 shown below was used instead of the compound D1, the example compound A15 was obtained by a method similar to that of Example 1.

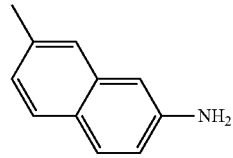

D7

The identification result of the compound thus obtained is shown below.
[MALDI-TOF-MS]
Measured value: m/z=506.43, calculated value: $C_{32}H_{54}N_2S_2$=506.72 [CV measurement]
First Oxidation Potential: −1.05 V

[Example 5] Synthesis of Example Compound B1

In Example 1(1), except that the compound D8 shown below was used instead of the compound D1, the example compound B1 was obtained by a method similar to that of Example 1.

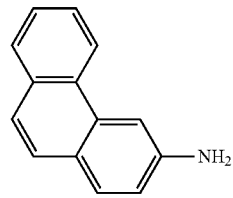

D8

The identification result of the compound thus obtained is shown below.
[MALDI-TOF-MS]
Measured value: m/z=578.72, calculated value: $C_{38}H_{30}N_2S_2$=578.79 [CV measurement]
First Oxidation Potential: −1.02 V

[Example 6] Synthesis of Example Compound C4

In Example 1(1), except that the compound D9 shown below was used instead of the compound D1, and the compound D10 shown below was used instead of the compound D2, the example compound C4 was obtained by a method similar to that of Example 1.

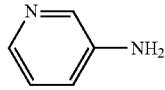

D9

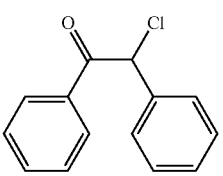

The identification result of the compound thus obtained is shown below.
[MALDI-TOF-MS]
Measured value: m/z=504.22, calculated value: $C_{30}H_{24}N_4S_2$=504.67 [CV measurement]
First Oxidation Potential: −0.90 V

[Example 7] Synthesis of Example Compound A2

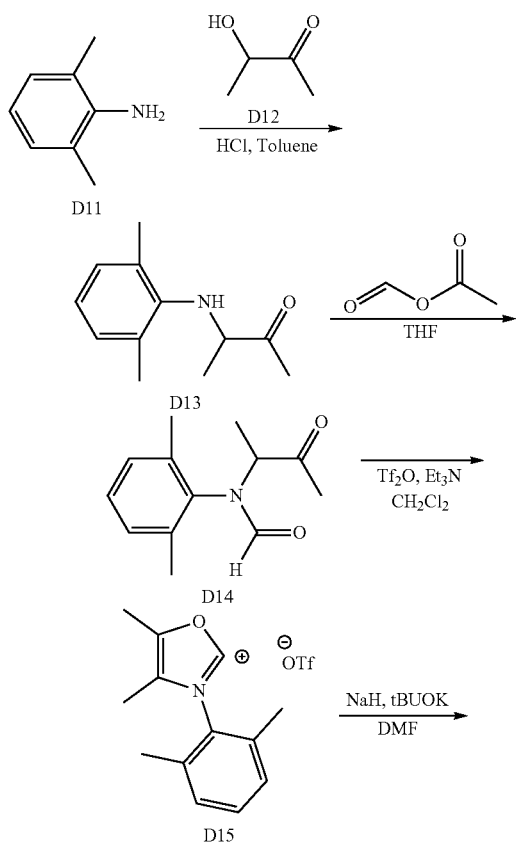

(1) Synthesis of Compound D13

The following reagents and solvents were charged into a 100-ml eggplant flask.
D11: 0.97 g (8.00 mmol)
D12: 1.41 g (16.0 mmol)
Conc. hydrochloric acid: 0.1 ml, dehydrated toluene: 30 ml Next, while water generated by the reaction was removed by the azeotropy, heating and stirring were performed for 3 hours. After the reaction was completed, the solution was concentrated under a reduced-pressure condition, so that a crude product was obtained. Subsequently, this crude product was purified using a silica gel column chromatography (eluent: heptane/ethyl acetate=50/1 to 10/1), so that 1.04 g (yield: 68%) of D13 was obtained.

(2) Synthesis of Compound D14

The following reagents and solvent were charged into a 50-ml eggplant flask.
D13: 1.04 g (5.44 mmol)
Acetic formic anhydride: 0.72 g (8.16 mmol)
THF: 5 ml The reaction solution was stirred at room temperature in a nitrogen atmosphere over one night. After the reaction was completed, the solution was concentrated under a reduced-pressure condition, so that a crude product was obtained. Subsequently, this crude product was purified using a silica gel column chromatography (eluent: heptane/ethyl acetate=50/1 to 10/1), so that 0.95 g (yield: 80%) of D14 was obtained.

(3) Synthesis of Compound D15

The following reagent and solvent were charged into a 50-ml eggplant flask.
D14: 329 mg (1.50 mmol)
Dichloromethane: 10 ml Next, the reaction solution was cooled to −40° C. while being stirred in a nitrogen atmosphere. Subsequently, 167 mg (1.65 mmol) of trimethylamine was slowly dripped. Furthermore, 465 mg (1.65 mmol) of trifluoromethane sulfonic acid anhydride was added. Next, the reaction solution was stirred at room temperature for 5 hours. After the reaction was completed, the solution was concentrated under a reduced-pressure condition, so that a crude product was obtained. Subsequently, this crude product was purified using a silica gel column chromatography (eluent: chloroform/ethanol=250/1 to 100/1), and dispersion washing was further performed using a heptane solvent, so that 242 mg (yield: 46%) of D15 was obtained.

(4) Synthesis of Example Compound A2

The following reagent and solvent were charged into a 50-ml eggplant flask in a nitrogen flow atmosphere.
D15: 242 mg (0.69 mmol)
Dehydrated DMF: 10 ml After this solution was deaerated using nitrogen, 132 mg (2.76 mmol) of sodium hydride (oil dispersion at 50% to 60%) was charged thereto, and stirring was then performed at room temperature for 2 minutes. Subsequently, 77 mg (0.69 mmol) of potassium tert-butoxide was added, and stirring was performed at room temperature for 6 hours. After the reaction was completed, while stirring was performed, 30 ml of water which was deaerated using nitrogen was slowly added to precipitate a target product, and the

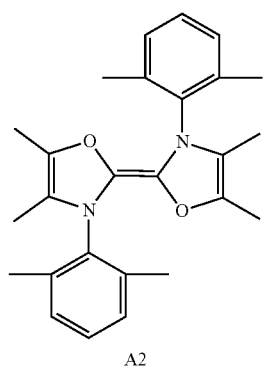

solvent was then removed using a syringe. Next, after the operation of adding 20 ml of water deaerated using nitrogen and removing the solvent using a syringe was again performed twice, 10 ml of hexane deaerated using nitrogen was added, and dispersion washing was performed by an ultrasonic washing machine. Subsequently, after filtration was performed using a membrane filter, and a residue was washed with hexane deaerated using nitrogen, drying was performed at 50° C. under a reduced-pressure condition, so that 76 mg (yield: 55%) of the example compound A2 in the form of yellow powder was obtained.

The identification result of the compound thus obtained is shown below.
[MALDI-TOF-MS]
Measured value: m/z=402.22, calculated value: $C_{26}H_{30}N_2O_2$=402.53 [CV measurement]
First oxidation potential: −1.06 V

[Example 8] Synthesis of Example Compound A16

In Example 7(1), except that the compound D16 shown below was used instead of the compound D12, the example compound A16 was obtained by a method similar to that of Example 7.

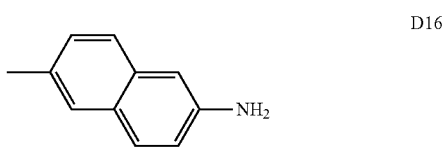

D16

The identification result of the compound thus obtained is shown below.
[MALDI-TOF-MS]
Measured value: m/z=474.42, calculated value: $C_{32}H_{30}N_2O_2$=474.59 [CV measurement]
First oxidation potential: −1.06 V

[Example 9] Synthesis of Example Compound AA9

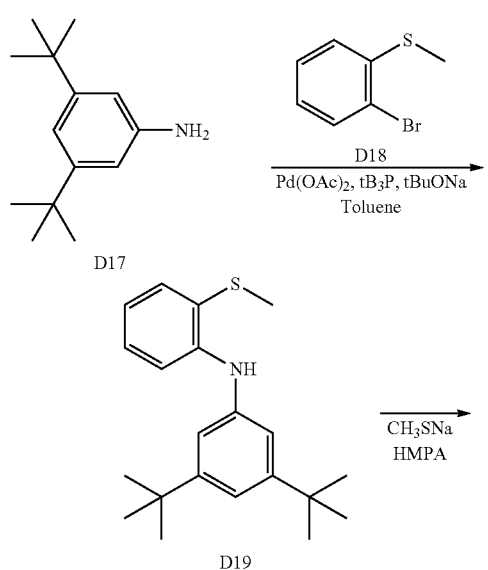

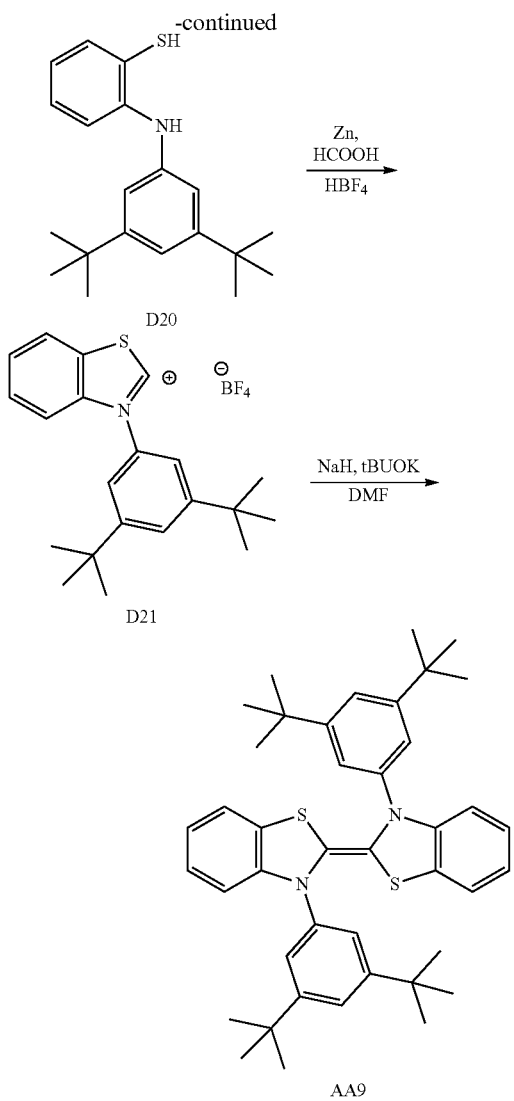

(1) Synthesis of Compound D19

The following reagents and solvents were charged into a 200-ml eggplant flask.
D17: 2,000 mg (9.74 mmol)
D18: 1,318 mg (6.49 mmol)
Palladium (0) Acetate: 85 mg (0.38 mmol)
t-butylphosphine: 262 mg (1.30 mmol)
sodium tert-butoxide: 1,247 mg (13.0 mmol)
dehydrated toluene: 50 ml Next, while being stirred in a nitrogen atmosphere, the reaction solution was heat-refluxed for 6 hours. After the reaction was completed, chloroform and water were added to the reaction solution and then stirred, and an organic layer was separated by liquid-liquid separation operation. Subsequently, after being washed using a saturated sodium chloride aqueous solution, the organic layer was dried with sodium sulfate. Next, the organic layer was concentrated under a reduced-pressure condition, so that a crude product was obtained. Subsequently, this crude product was purified using a silica gel column chromatography (eluent: chloroform/heptane=1/4 to 1/1) and was further processed by dispersion washing using a heptane solvent, so that 1,721 mg (yield: 81%) of D19 was obtained.

(2) Synthesis of Compound D20

The following reagents and solvent were charged into a 200-ml eggplant flask.
D19: 1,500 mg (4.58 mmol)
Sodium methyl mercaptan, 15% aqueous solution: 3,200 mg (6.87 mmol)
Hexamethylphosphoric triamide: 20 ml Next, while being stirred in a nitrogen atmosphere, the reaction solution was heat-refluxed for 6 hours. After the reaction was completed, 30 ml of 1 N hydrochloric acid was added to the reaction solution at room temperature and then stirred. Subsequently, water and ethyl acetate were added, and an organic layer was separated by liquid-liquid separation operation. Next, after being washed using a saturated sodium chloride aqueous solution, the organic layer was dried with sodium sulfate. The organic layer was then concentrated under a reduced-pressure condition, so that 1,140 mg (yield: 79%) of D20 was obtained.

(3) Synthesis of Compound D21

The following reagents and solvent were charged into a 100-ml eggplant flask.
D20: 1,000 mg (3.19 mmol)
Zinc powder: 333 mg (5.10 mmol)
Formic acid: 10 ml Next, while being stirred in a nitrogen atmosphere, the reaction solution was heat-refluxed for 6 hours. After the reaction was completed, the temperature was decreased to room temperature, and filtration was performed using a membrane filter, so that a residue was removed. Subsequently, 0.60 ml of hydrofluoroboric acid (42% aqueous solution) was added to the filtrate and was then stirred. Next, 20 ml of water was added, and a residue was filtrated, so that a crude product was obtained. To the crude product thus obtained, diethyl ether was added, and dispersion washing was performed using an ultrasonic washing machine, so that 852 mg (yield: 65%) of D21 was obtained.

(4) Synthesis of Example Compound AA9

The following reagent and solvent were charged into a 50-ml eggplant flask in a nitrogen flow atmosphere.
D21: 500 mg (1.21 mmol)
Dehydrated DMF: 15 ml After this solution was deaerated using nitrogen, 116 mg (2.42 mmol) of sodium hydride (oil dispersion at 50% to 60%) was charged thereto, and stirring was then performed for 2 minutes. Subsequently, 135 mg (1.21 mmol) of potassium tert-butoxide was added, and stirring was performed at room temperature for 6 hours. After the reaction was completed, while stirring was performed, 30 ml of water which was deaerated using nitrogen was slowly added to precipitate a target product, and the solvent was then removed using a syringe. Next, after the operation of adding 20 ml of water deaerated using nitrogen and removing the solvent using a syringe was again performed twice, 10 ml of hexane deaerated using nitrogen was added, and dispersion washing was performed by an ultrasonic washing machine. Subsequently, after filtration was performed using a membrane filter, and a residue was washed with hexane deaerated using nitrogen, drying was performed at 50° C. under a reduced-pressure condition, so that 250 mg (yield: 65%) of the example compound AA9 in the form of red powder was obtained.

The identification result of the compound thus obtained is shown below.
[MALDI-TOF-MS]
Measured value: m/z=646.72, calculated value: $C_{45}H_{50}N_4$=646.99 [CV measurement]
First oxidation potential: −1.01 V

[Example 10] Synthesis of Example Compound AA15

In Example 9(1), except that the compound D22 shown below was used instead of the compound D17, the example compound AA15 was obtained by a method similar to that of Example 9.

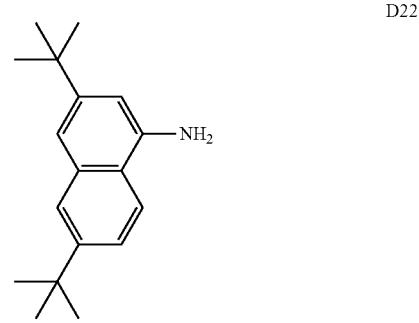 [SMILES: CC(C)(C)c1ccc2c(N)cc(C(C)(C)C)cc2c1]

D22

The identification result of the compound thus obtained is shown below.
[MALDI-TOF-MS]
Measured value: m/z=747.42, calculated value: $C_{50}H_{54}N_2S_2$=747.11 [CV measurement]
First oxidation potential: −1.00 V

[Example 11] Synthesis of Example Compound AA2

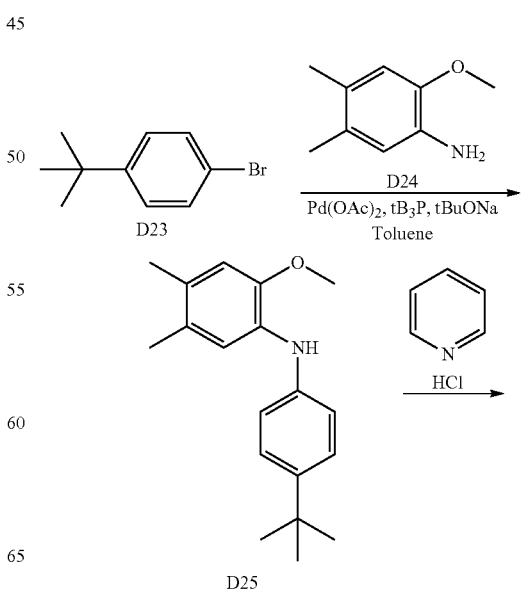

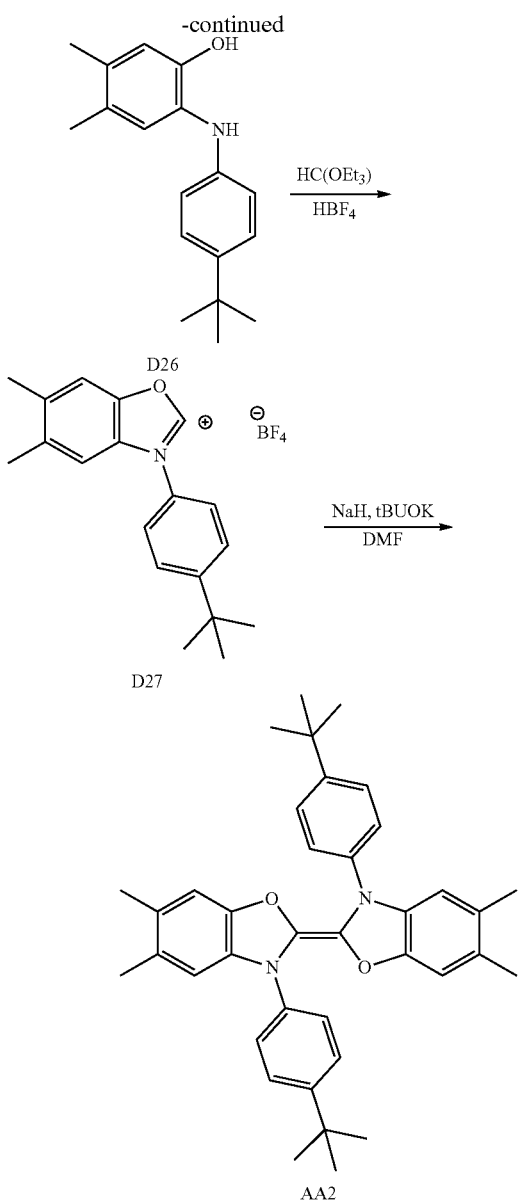

(1) Synthesis of Compound D25

The following reagents and solvent were charged into a 200-ml eggplant flask.
D23: 1,380 mg (6.49 mmol)
D24: 1,200 mg (9.74 mmol)
Palladium (0) Acetate: 85 mg (0.38 mmol)
t-butylphosphine: 262 mg (1.30 mmol)
sodium tert-butoxide: 1,247 mg (13.0 mmol)
dehydrated toluene: 50 ml Next, while being stirred in a nitrogen atmosphere, the reaction solution was heat-refluxed for 6 hours. After the reaction was completed, chloroform and water were added to the reaction solution and then stirred, and an organic layer was separated by liquid-liquid separation operation. Subsequently, after being washed using a saturated sodium chloride aqueous solution, the organic layer was dried with sodium sulfate. Next, the organic layer was concentrated under a reduced-pressure condition, so that a crude product was obtained. Subsequently, this crude product was purified using a silica gel column chromatography (eluent: chloroform/heptane=1/4 to 1/1) and was further processed by dispersion washing using a heptane solvent, so that 1,408 mg (yield: 85%) of D25 was obtained.

(2) Synthesis of Compound D26

The following reagents were charged into a 200-ml eggplant flask.
D25: 1,400 mg (5.49 mmol)
Pyridine hydrochloride: 6,344 mg (54.9 mmol)

Next, while being stirred, the reaction solution was heated at 200° C. in a nitrogen atmosphere for 6 hours. After the reaction was completed, ethyl acetate and 0.5 N hydrochloric acid were added to the reaction solution, and an organic layer was separated by liquid-liquid separation operation. Subsequently, after being washed using a saturated sodium chloride aqueous solution, the organic layer was dried with sodium sulfate. Next, the organic layer was concentrated under a reduced-pressure condition, so that a crude product was obtained. Subsequently, this crude product was purified using a silica gel column chromatography (eluent: chloroform/heptane=1/1 to 5/1) and was further processed by dispersion washing using a heptane solvent, so that 820 mg (yield: 62%) of D26 was obtained.

(3) Synthesis of Compound D27

The following reagents and solvent were charged into a 100-ml eggplant flask.
D26: 820 mg (3.40 mmol)
Trimethyl orthoformate: 10 ml
Hydrofluoroboric acid (42% aqueous solution): 0.7 ml Next, the reaction solution was stirred at room temperature in a nitrogen atmosphere for 24 hours. After the reaction was completed, a residue was filtrated using a membrane filter at room temperature, so that a crude product was obtained. To the crude product thus obtained, diethyl ether was added, and dispersion washing was performed using an ultrasonic washing machine, so that 725 mg (yield: 63%) of D27 was obtained.

(4) Synthesis of Example Compound AA2

The following reagent and solvent were charged into a 50-ml eggplant flask in a nitrogen flow atmosphere.
D27: 500 mg (1.47 mmol)
Dehydrated DMF: 15 ml After this solution was deaerated using nitrogen, 140 mg (2.94 mmol) of sodium hydride (oil dispersion at 50% to 60%) was charged thereto, and stirring was then performed at room temperature for 2 minutes. Subsequently, 164 mg (1.47 mmol) of potassium tert-butoxide was added, and stirring was performed at room temperature for 6 hours. After the reaction was completed, while stirring was performed, 30 ml of water which was deaerated using nitrogen was slowly added to precipitate a target product, and the solvent was then removed using a syringe. Next, after the operation of adding 20 ml of water deaerated using nitrogen and removing the solvent using a syringe was again performed twice, 10 ml of hexane deaerated using nitrogen was added, and dispersion washing was performed by an ultrasonic washing machine. Subsequently, after filtration was performed using a membrane filter, and a residue was washed with hexane deaerated using nitrogen, drying was performed at 50° C. under a reduced-pressure condition, so that 221 mg (yield: 60%) of the example compound AA2 in the form of yellowish brown powder was obtained.

The identification result of the compound thus obtained is shown below.
[MALDI-TOF-MS]
Measured value: m/z=502.98, calculated value: $C_{34}H_{34}N_2O_2$=502.65 [CV measurement]
First oxidation potential: −1.01 V

[Example 12] Synthesis of Example Compound CC7

In Example 11(1), except that the compound D28 shown below was used instead of the compound D23, the example compound CC7 was obtained by a method similar to that of Example 11.

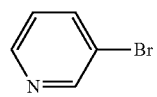

D28

The identification result of the compound thus obtained is shown below
[MALDI-TOF-MS]
Measured value: m/z=448.32, calculated value: $C_{28}H_{24}N_4O_2$=448.52 [CV measurement]
First oxidation potential: −0.91 V

[Comparative Example 1] Synthesis of Comparative Compound 3

(1) Synthesis of Compound D31

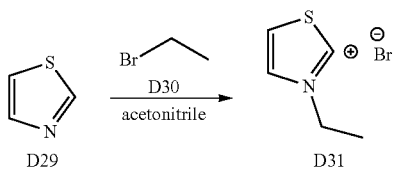

The following reagents and solvent were charged into a 50-ml eggplant flask
D29: 500 mg (5.88 mmol) (obtained from Tokyo Chemical Industry Co., Ltd.)
D30: 1,923 mg (17.6 mmol)
Dehydrated acetonitrile: 15 ml Next, while being stirred in a nitrogen atmosphere, the reaction solution was heat-refluxed for 24 hours. After the reaction was completed, the reaction solution was cooled, and a precipitated white sold was filtrated. After the residue was washed with diethyl ether, drying was performed at 100° C. under a reduced-pressure condition, so that 1,000 mg (yield: 88%) of D31 was obtained.

(2) Synthesis of Comparative Compound 3

In Example 1(3), except that the compound D31 described above was used instead of the compound D4, the comparative compound 3 was synthesized by a method similar to that of Example 1. It was confirmed that this compound partially deliquesced during the synthesis and purification operations. In addition, the comparative compound 3 is described in Non-Patent Literature 1 and has the structure in which the methyl group of the compound 1-A in this specification is substituted by a hydrogen atom.

[Comparative Example 2] Synthesis of Comparative Compound 4

In Example 1(3), except that the compound D32 (obtained from Tokyo Chemical Industry Co., Ltd.) shown below was used instead of the compound D4, the comparative compound 4 was synthesized by a method similar to that of Example 1. It was confirmed that this compound partially deliquesced during the synthesis and purification operations. In addition, the comparative compound 4 is described in Non-Patent Literature 1 and has the same structure as that of the compound 1-B of this specification.

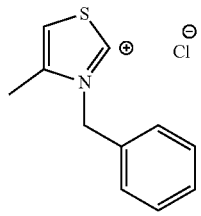

D32

[Comparative Example 3] Synthesis of Comparative Compound 5

In Example 1(3), except that the compound D33 (obtained from Tokyo Chemical Industry Co., Ltd.) shown below was used instead of the compound D4, the comparative compound 5 was synthesized by a method similar to that of Example 1. It was confirmed that this compound partially deliquesced during the synthesis and purification operations. In addition, the comparative compound 4 is described in Non-Patent Literature 2 and has the same structure as that of the compound 1-C of this specification.

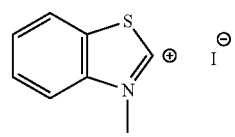

D33

Examples 13 to 20

In the following examples, an organic light emitting element was formed in which on a substrate, an anode, a hole transport layer, an electron blocking layer, a light emitting layer, an electron transport layer, and a cathode were sequentially formed.

First, an ITO film was formed on a glass substrate, and desired patterning was then performed, so that an ITO electrode (anode) was formed. In this case, the film thickness of the ITO electrode was set to 100 nm. The substrate on which the ITO electrode was formed as described above was used as an ITO substrate in the following steps.

On the ITO substrate described above, the organic compound layers and the electrode layer shown in the following Table 2 were continuously formed. In addition, the electrode area of the counter electrode (metal electrode layer, cathode) was set to 3 mm2.

TABLE 2

| | MATERIAL | FILM THICKNESS (nm) |
|---|---|---|
| HOLE TRANSPORT LAYER | G-1 | 30 |
| ELECTRON BLOCKING LAYER | G-2 | 10 |
| LIGHT EMITTING LAYER | G-3 (HOST) G-4 (GUEST) (G-3:G-4 = 98:2 (WEIGHT RATIO)) | 30 |
| ELECTRON TRANSPORT LAYER | G-5 | 25 |
| ELECTRON INJECTION LAYER | G-6 G-7 (G-6:G-7 = 50:50 (WEIGHT RATIO)) | 15 |
| METAL ELECTRODE LAYER | Al | 100 |

In this case, before the metal electrode layer was formed, the substrate was left in the air for 10 minutes, and subsequently, the metal electrode layer was formed. G1 to G6 represent the organic compounds shown in the following Table 3, and the organic compounds according to the present disclosure and the comparative compounds 3, 4, and 5 were each used for G7, so that the evaluation was performed.

TABLE 3

| | G1 | G2 | G3 | G4 | G5 | G6 | G7 | LIGHT EMISSION CONDITION |
|---|---|---|---|---|---|---|---|---|
| EXAMPLE 13 | HT1 | HT7 | EM 13 | RD1 | ET10 | EI6 | A6 | ○ |
| EXAMPLE 14 | HT1 | HT7 | EM 13 | RD1 | ET10 | EI6 | A15 | ○ |
| EXAMPLE 15 | HT1 | HT7 | EM 13 | RD1 | ET10 | EI6 | A16 | ○ |
| EXAMPLE 16 | HT1 | HT7 | EM 13 | RD1 | ET10 | EI6 | B1 | ○ |
| EXAMPLE 17 | HT1 | HT7 | EM 13 | RD1 | ET10 | EI6 | C4 | ○ |
| EXAMPLE 18 | HT1 | HT7 | EM 13 | RD1 | ET10 | EI6 | AA9 | ○ |
| EXAMPLE 19 | HT1 | HT7 | EM 13 | RD1 | ET10 | EI6 | AA2 | ○ |
| EXAMPLE 20 | HT1 | HT7 | EM 13 | RD1 | ET10 | EI6 | CC7 | ○ |
| COMPARATIVE EXAMPLE 4 | HT1 | HT7 | EM 13 | RD1 | ET10 | EI6 | COMPARATIVE COMPOUND 3 | x |
| COMPARATIVE EXAMPLE 5 | HT1 | HT7 | EM 13 | RD1 | ET10 | EI6 | COMPARATIVE COMPOUND 4 | x |
| COMPARATIVE EXAMPLE 6 | HT1 | HT7 | EM 13 | RD1 | ET10 | EI6 | COMPARATIVE COMPOUND 5 | x |

As a result, when light emission was confirmed by applying a voltage of 8 V, although the light emission of the organic compound according to the present disclosure was confirmed, the light emission of each of the comparative compounds 3, 4, and 5 was not confirmed. The reason for this is believed that when exposed to the air, the comparative compounds 3, 4, and 5 were denatured, and hence, the electron injection property thereof was lost.

Examples 21 to 29

By the use of the organic compound layers and the electrode layer shown in the following Table 4, elements were formed in a manner similar to that of Examples 13 to 20.

TABLE 4

| | MATERIAL | FILM THICKNESS (nm) |
|---|---|---|
| HOLE TRANSPORT LAYER | G-1 | 30 |
| ELECTRON BLOCKING LAYER | G-2 | 10 |
| LIGHT EMITTING LAYER | G-3 (HOST) G-4 (GUEST) (G-3:G-4 = 98:2 (WEIGHT RATIO)) | 30 |
| ELECTRON TRANSPORT LAYER | G-5 | 25 |
| ELECTRON INJECTION LAYER | G-6 G-7 (G-6:G-7 = 50:50 (WEIGHT RATIO)) | 15 |
| METAL ELECTRODE LAYER | G-8 | 100 |

In this case, after the organic compounds and the metals shown in the following Table 5 were used for G1 to G6 and G8, and the organic compound according to the present disclosure was used for G7, the evaluation was performed. In addition, when the metals were mixed together, the mixing ratio thereof was represented by the weight ratio shown in the table. By applying the voltage between the ITO electrode functioning as the anode and the counter electrode functioning as the cathode of the organic light emitting element thus obtained so as to obtain a current density of 100 mA/cm², the light emission efficiency and the application voltage were measured. The results are shown in Table 5.

As for the measurement devices, the current-voltage characteristics were measured using a micro-ammeter 4140B manufactured by Hewlett-Packard, and the light emission luminance was measured using BM7 manufactured by Topcon Corp.

TABLE 5

|  | G1 | G2 | G3 | G4 | G5 | G6 | G7 | G8 | LIGHT EMISSION EFFICIENCY (cd/A) | VOLTAGE (V) |
|---|---|---|---|---|---|---|---|---|---|---|
| EXAMPLE 21 | HT6 | HT7 | EM13 | RD1 | ET10 | EI6 | A1 | Ag | 4 | 8 |
| EXAMPLE 22 | HT2 | HT7 | EM3 | BD4 | ET10 | EI6 | A6 | Ag | 6 | 8 |
| EXAMPLE 23 | HT6 | HT7 | EM4 | GD4 | ET9 | EI6 | B1 | Au | 17 | 7 |
| EXAMPLE 24 | HT6 | HT8 | EM8 | RD4 | ET9 | EI6 | C1 | Ag:Mg = 1:1 | 7 | 7 |
| EXAMPLE 25 | HT2 | HT8 | EM14 | RD2 | ET10 | EI6 | C5 | Ag | 4 | 7 |
| EXAMPLE 26 | HT2 | HT7 | EM4 | BD1 | ET9 | EI6 | A2 | Ag:Cu = 5:1 | 5 | 8 |
| EXAMPLE 27 | HT6 | HT7 | EM13 | RD1 | ET10 | EI6 | AA9 | Ag | 4 | 8 |
| EXAMPLE 28 | HT2 | HT7 | EM3 | BD4 | ET10 | EI6 | AA12 | Ag | 6 | 8 |
| EXAMPLE 29 | HT2 | HT8 | EM14 | RD2 | ET10 | EI6 | AA15 | Ag | 4 | 7 |

Examples 30 to 37

In the following examples, an organic light emitting element was formed in which an anode, a hole transport layer, an electron blocking layer, a light emitting layer, a hole blocking layer, an electron transport layer, and a cathode were sequentially formed on a substrate. By the use of the organic compound layers and the electrode layer shown in the following Table 6, element formation and measurement were performed in a manner similar to that of Examples 13 to 20.

TABLE 6

|  | MATERIAL | FILM THICKNESS (nm) |
|---|---|---|
| HOLE TRANSPORT LAYER | G-1 | 30 |
| ELECTRON BLOCKING LAYER | G-2 | 10 |
| LIGHT EMITTING LAYER | G-3 (HOST) G-4 (GUEST) (G-3:G-4 = 98:2 (WEIGHT RATIO)) | 30 |
| HOLE BLOCKING LAYER | G-5 | 10 |
| ELECTRON TRANSPORT LAYER | G-6 | 26 |
| ELECTRON INJECTION LAYER | G-7 | 4 |
| METAL ELECTRODE LAYER | G-8 | 100 |

In this case, after the organic compounds and the metals shown in the following Table 7 were used for G1 to G6 and G8, and the organic compound according to the present disclosure was used for G7, evaluation was performed. In addition, when the metals were mixed together, the mixing ratio thereof was represented by the weight ratio shown in the table.

TABLE 7

|  | G1 | G2 | G3 | G4 | G5 | G6 | G7 | G8 | LIGHT EMISSION EFFICIENCY (cd/A) | VOLTAGE (V) |
|---|---|---|---|---|---|---|---|---|---|---|
| EXAMPLE 30 | HT6 | HT7 | EM13 | RD1 | ET10 | EI6 | A15 | Ag:Mg = 1:1 | 4 | 8 |
| EXAMPLE 31 | HT6 | HT7 | EM4 | BD6 | ET10 | EI9 | A16 | Ag | 5 | 9 |
| EXAMPLE 32 | HT2 | HT7 | EM7 | GD6 | ET9 | EI17 | A2 | Au | 20 | 8 |
| EXAMPLE 33 | HT1 | HT8 | EM14 | RD1 | ET9 | EI14 | A14 | Ag:Al = 1:1 | 5 | 8 |
| EXAMPLE 34 | HT2 | HT8 | EM8 | BD8 | ET10 | EI12 | C4 | Al | 4 | 9 |
| EXAMPLE 35 | HT6 | HT7 | EM4 | BD6 | ET10 | EI9 | AA17 | Ag | 5 | 9 |
| EXAMPLE 36 | HT2 | HT8 | EM8 | BD8 | ET10 | EI12 | AA12 | Al | 4 | 9 |
| EXAMPLE 37 | HT1 | HT8 | EM14 | RD1 | ET9 | EI14 | AA18 | Ag:Al = 1:1 | 5 | 8 |

As described above with reference to the examples, when the fulvalene compound according to this embodiment is used for the electron injection layer, an organic light emitting element stable in the air can be formed. Accordingly, a stable element having a long serviceable life can be obtained.

As has thus been described, the fulvalene compound according to the present disclosure is a compound having a high stability in the air. In addition, an organic light emitting element in which the fulvalene compound according to the present disclosure is used for the electron injection layer is stable against moisture and oxygen. Accordingly, an organic light emitting element having a high light emission efficiency and excellent life characteristics can be provided.

The present disclosure can provide a highly stable organic light emitting element containing a fulvalene compound which can be stably present due to its low reactivity with oxygen and moisture in the air.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A composition containing an organic compound represented by the following formula [1] and an organic compound selected from the group consisting of a compound having a polycyclic structure, a compound having a fluoranthene backbone, a compound having a cyano group, and a compound having a fluorine atom,

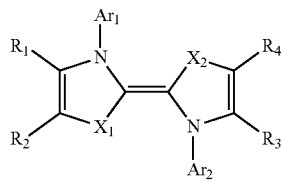

[1]

wherein, in the formula [1],
$Ar_1$ and $Ar_2$ are each independently selected from the group consisting of a substituted or unsubstituted aromatic hydrocarbon group and a substituted or unsubstituted heteroaromatic ring group,
$Ar_1$ and $Ar_2$ each may have a substituent selected from the group consisting of a halogen atom, a cyano group, an alkyl group, and a substituted or unsubstituted aryl group,
$R_1$ to $R_4$ are each independently selected from the group consisting of a halogen atom, a cyano group, an alkyl group, and a substituted or unsubstituted aryl group,
$R_1$ and $R_2$, and $R_3$ and $R_4$ each may form a ring, the ring may have a substituent selected from the group consisting of a halogen atom, a cyano group, an alkyl group, and a substituted or unsubstituted aryl group,
$X_1$ and $X_2$ each represent a sulfur atom or an oxygen atom, and $X_1$ and $X_2$ may be the same or different, and
wherein an oxidation potential of the organic compound represented by the formula [1] is between −1.20 to −0.80 Volts in a dimethylformamide solvent.

2. The composition according to claim 1, wherein the $Ar_1$ and $Ar_2$ are each substituted by a substituent selected from the group of a halogen atom, a cyano group, an alkyl group having 1 to 4 carbon atoms and an aromatic hydrocarbon group.

3. The composition according to claim 1, wherein the $Ar_1$ and $Ar_2$ are each substituted by a substituent selected from the group consisting of a tert-butyl group and a halogen atom.

4. The composition according to claim 1, wherein $R_1$ and $R_2$, $R_3$ and $R_4$ each may form the ring, the ring is a benzene ring.

5. An organic light-emitting element comprising:
a first electrode;
a second electrode; and
an organic compound layer disposed between the first electrode and the second electrode,
wherein the organic compound layer contains the composition according to claim 1.

6. An organic light-emitting element comprising:
a first electrode;
a second electrode;
a light emitting layer disposed between the first electrode and the second electrode; and
an organic compound layer disposed between the first electrode and the light emitting layer,
wherein the organic compound layer contains the composition according to claim 1.

7. The organic light-emitting element according to claim 6, wherein the first electrode is a cathode, and the second electrode is an anode.

8. The organic light-emitting element according to claim 7, wherein the first electrode is in contact with the organic compound layer.

9. A display device comprising:
a plurality of pixels, at least one of the pixels comprising the organic light-emitting element according to claim 6.

10. A lighting device comprising: the organic light-emitting element according to claim 6 and a switching element connected to the organic light-emitting element.

11. An organic compound represented by the following formula [2],

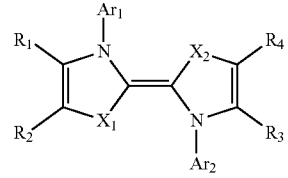

[2]

wherein, in the formula [2],
$Ar_1$ and $Ar_2$ are each independently selected from the group consisting of a substituted or unsubstituted aromatic hydrocarbon group and a substituted or unsubstituted heteroaromatic ring group,
at least one of $Ar_1$ and $Ar_2$ has a substituent selected from the group consisting of a halogen atom and a tert-butyl group,
$R_1$ to $R_4$ are each independently selected from the group consisting of a halogen atom, a cyano group, an alkyl group, and a substituted or unsubstituted aryl group,
$R_1$ and $R_2$, and $R_3$ and $R_4$ each may form a ring, the ring may have a substituent selected from the group consisting of a halogen atom, a cyano group, an alkyl group, and a substituted or unsubstituted aryl group, $X_1$ and $X_2$ each represent a sulfur atom or an oxygen atom, and $X_1$ and $X_2$ may be the same or different, and wherein an oxidation potential of the organic compound represented by the formula [2] is between −1.20 to −0.80 Volts in a dimethylformamide solvent.

12. The organic compound according to claim 11, wherein $R_1$ and $R_2$, $R_3$ and $R_4$ each may form the ring, the ring is a benzene ring.

13. An organic light-emitting element comprising:
a first electrode;
a second electrode; and
an organic compound layer disposed between the first electrode and the second electrode,
wherein the organic compound layer contains the organic compound represented by formula [2] according to claim 11.

14. An organic light-emitting element comprising:
a first electrode;
a second electrode;
a light emitting layer disposed between the first electrode and the second electrode; and
an organic compound layer disposed between the first electrode and the light emitting layer,
wherein the organic compound layer contains the organic compound represented by formula [2] according to claim 11.

15. The organic light-emitting element according to claim 14,
wherein the organic compound layer contains the organic compound represented by formula [2] an organic compound selected from the group consisting of a compound having a polycyclic structure, a compound having a fluoranthene backbone, a compound having a cyano group, and a compound having a fluorine atom.

16. A display device comprising:
a plurality of pixels, at least one of the pixels comprising the organic light-emitting element according to claim 13.

17. A lighting device comprising: the organic light-emitting element according to claim 13 and a switching element connected to the organic light-emitting element.

18. An organic compound represented by the following formula [3],

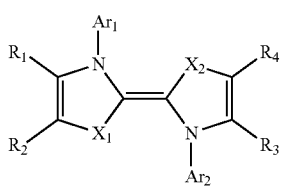

[3]

wherein, in the formula [3], $Ar_1$ and $Ar_2$ are each independently selected from the group consisting of a substituted or unsubstituted aromatic hydrocarbon group and a substituted or unsubstituted heteroaromatic ring group, $Ar_1$ and $Ar_2$ each may have a substituent selected from the group consisting of a halogen atom, a cyano group, an alkyl group, and a substituted or unsubstituted aryl group, $R_1$ to $R_4$ are each independently selected from the group consisting of a halogen atom, a cyano group, an alkyl group, and a substituted or unsubstituted aryl group, at least one of $R_1$ and $R_2$, and $R_3$ and $R_4$ are bonded to each other to form a ring, the ring may have a substituent selected from the group consisting of a halogen atom, a cyano group, an alkyl group, and a substituted or unsubstituted aryl group, $X_1$ and $X_2$ each represent a sulfur atom or an oxygen atom, and $X_1$ and $X_2$ may be the same or different, and wherein an oxidation potential of the organic compound represented by the formula [3] is between −1.20 to −0.80 Volts in a dimethylformamide solvent.

19. An organic light-emitting element comprising:
a first electrode;
a second electrode;
a light emitting layer disposed between the first electrode and the second electrode; and
an organic compound layer disposed between the first electrode and the light emitting layer,
wherein the organic compound layer contains the organic compound represented by formula [2] according to claim 18.

20. A display device comprising:
a plurality of pixels, at least one of the pixels comprising the organic light-emitting element according to claim 19.

21. The composition according to claim 1, wherein the $Ar_1$ and $Ar_2$ are substituted or unsubstituted phenyl groups.

22. The composition according to claim 11, wherein the $Ar_1$ and $Ar_2$ are substituted or unsubstituted phenyl groups.

23. The composition according to claim 18, wherein the $Ar_1$ and $Ar_2$ are substituted or unsubstituted phenyl groups.

* * * * *